(12) United States Patent
Uckun et al.

(10) Patent No.: US 6,294,575 B1
(45) Date of Patent: Sep. 25, 2001

(54) BTK INHIBITORS AND METHODS FOR THEIR IDENTIFICATION AND USE

(75) Inventors: Fatih M. Uckun, White Bear Lake; Yaguo Zheng, New Brighton; Sutapa Ghosh, Shoreview, all of MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/688,426

(22) Filed: Oct. 16, 2000

Related U.S. Application Data

(63) Continuation of application No. 09/273,191, filed on Mar. 19, 1999.
(60) Provisional application No. 60/097,360, filed on Aug. 21, 1998.

(51) Int. Cl.$^7$ .................................................. A01N 37/34
(52) U.S. Cl. .................. 514/521; 514/238.5; 514/331; 514/428; 514/548; 544/163; 546/230; 548/567; 558/392; 560/250
(58) Field of Search .................. 514/238.5, 331, 514/428, 521, 548; 544/163; 546/230; 548/567; 558/392; 560/250

(56) References Cited

U.S. PATENT DOCUMENTS

| | | | |
|---|---|---|---|
| 5,308,865 | 5/1994 | Bartlett et al. | 514/465 |
| 5,489,697 | 2/1996 | Boulanger et al. | 549/278 |
| 5,494,911 | 2/1996 | Bartlett et al. | 514/256 |
| 5,700,823 | 12/1997 | Hirth et al. | 514/380 |
| 5,747,664 | 5/1998 | Schleyerbach et al. | 558/392 |
| 5,780,592 | 7/1998 | Müllner et al. | 530/359 |

FOREIGN PATENT DOCUMENTS

| | | |
|---|---|---|
| 25 55 685 | 6/1977 | (DE) . |
| 0 537 742 A2 | 4/1993 | (EP) . |
| 0 551 230 A1 | 7/1993 | (EP) . |
| 0 652 214 A1 | 5/1995 | (EP) . |
| WO 91/17748 | 11/1991 | (WO) . |
| WO 94/14789 | 7/1994 | (WO) . |
| WO 96/26934 | 9/1996 | (WO) . |
| WO 96/31206 | 10/1996 | (WO) . |
| WO 98/25608 | 6/1998 | (WO) . |

OTHER PUBLICATIONS

Chemj. Abst. 96:34913 (1982).
Chem Abst. 86:105977 (1977).
Ahluwalia, V. et al., "Formation of 4–Ethylcoumarins from β–Diketones–Reaction Mechanism", *Indian Journal of Chemistry*, vol. 15B, pp. 240–241 (1977).
Crombie, L. et al., "Synthesis of Mammeins and Surangin A", *Tetrahedron Letters*, vol. 26, No. 24, pp. 2929–2932 (1985).
Ghosh, S. et al., "α–Cyano–β–hydroxy–β–methyl–N–[4–(trifluoromethoxy)phenyl]Propenamide: An Inhibitor of the Epidermal Growth Factor Receptor Tyrosine Kinase with Potent Cytotoxic Activity against Breast Cancer Cells", *Clinical Cancer Research*, vol. 4, pp. 2657–2668 (Nov. 1998).
Mahajan, S. et al., "Rational Design and Synthesis of a Novel Anti–leukemic Agent Targeting Bruton's Tyrosine Kinase (BTK), LFMA13 [α–Cyano–β–Hydroxy–β–Methyl–N–(2,5–Dibromophenyl)Propenamide]", *Journal of Biological Chemistry*, vol. 274, No. 14, pp. 9587–9599 (Apr. 2, 1999).
Rehse, K. et al., "Coumarin Derivatives Related to Calophylloid", *Arch. Pharm.*, vol. 311, No. 1, pp. 52–58, Abstract only (1978).

*Primary Examiner*—Peter O'Sullivan
(74) *Attorney, Agent, or Firm*—Merchant & Gould P.C.

(57) ABSTRACT

The invention provides BTK inhibitors, methods for their identification and use, and pharmaceutical compositions comprising BTK inhibitors.

6 Claims, 39 Drawing Sheets

FIG. 4A
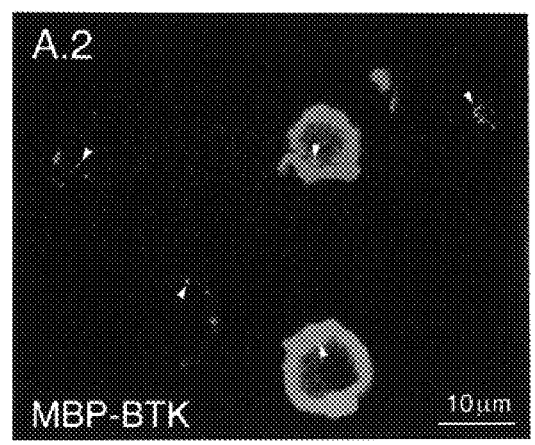

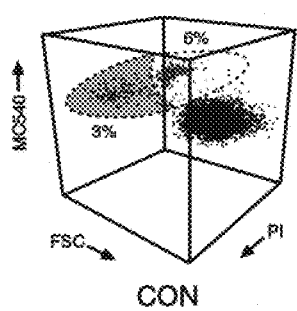
FIG. 17A  CON
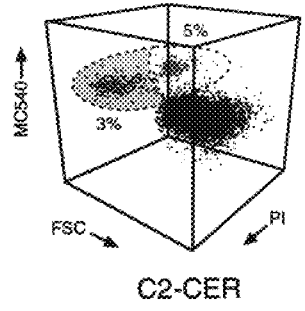
FIG. 17B  C2-CER
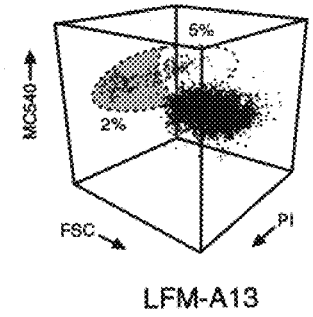
FIG. 17C  LFM-A13
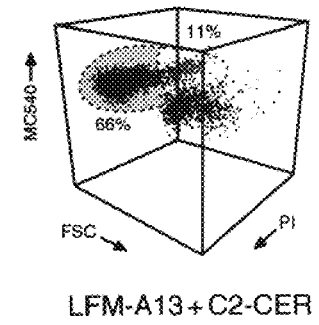
FIG. 17D  LFM-A13+C2-CER

FIG. 20A
BINDING MODE 1
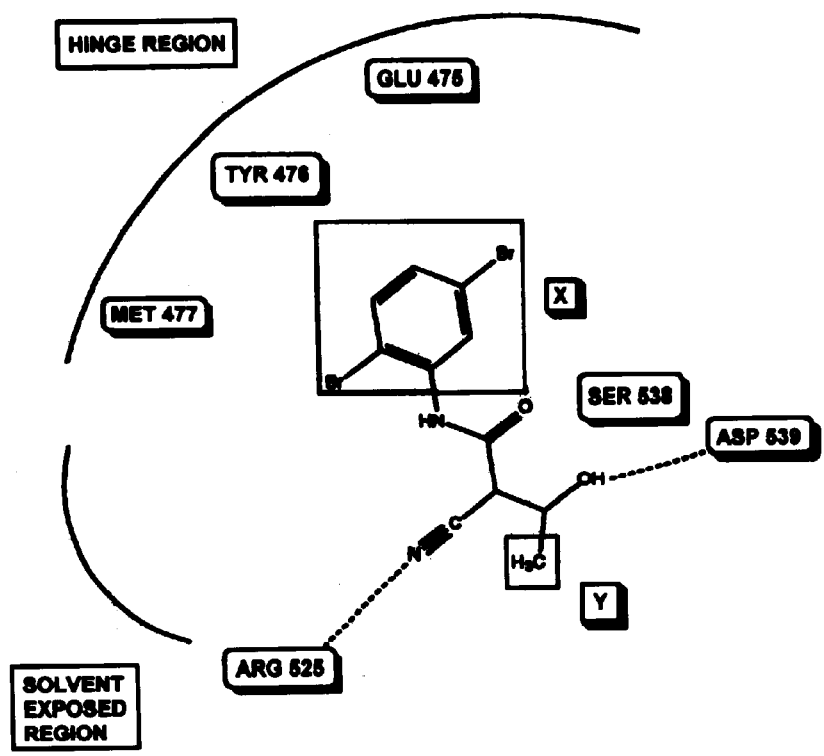
X = 1 - 6
(1) 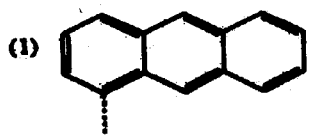  (2) 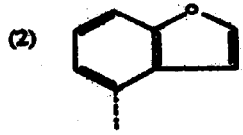
Y = Hydrophilic substitutions between one and three atoms
(3) 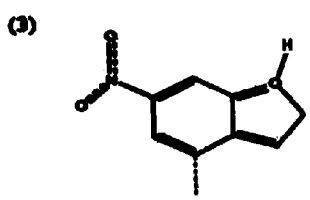  (4) 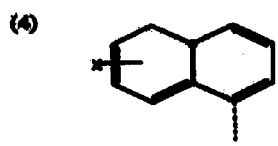
X = F, CL, Br, CF3
(5) 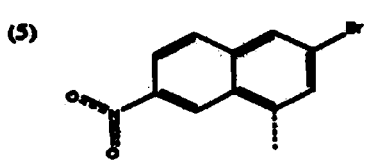  (6) 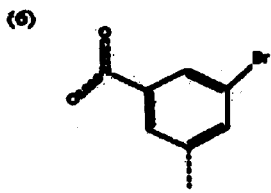

BINDING MODE 1

Binding MODE 1

FIG. 20C
BINDING MODE 2
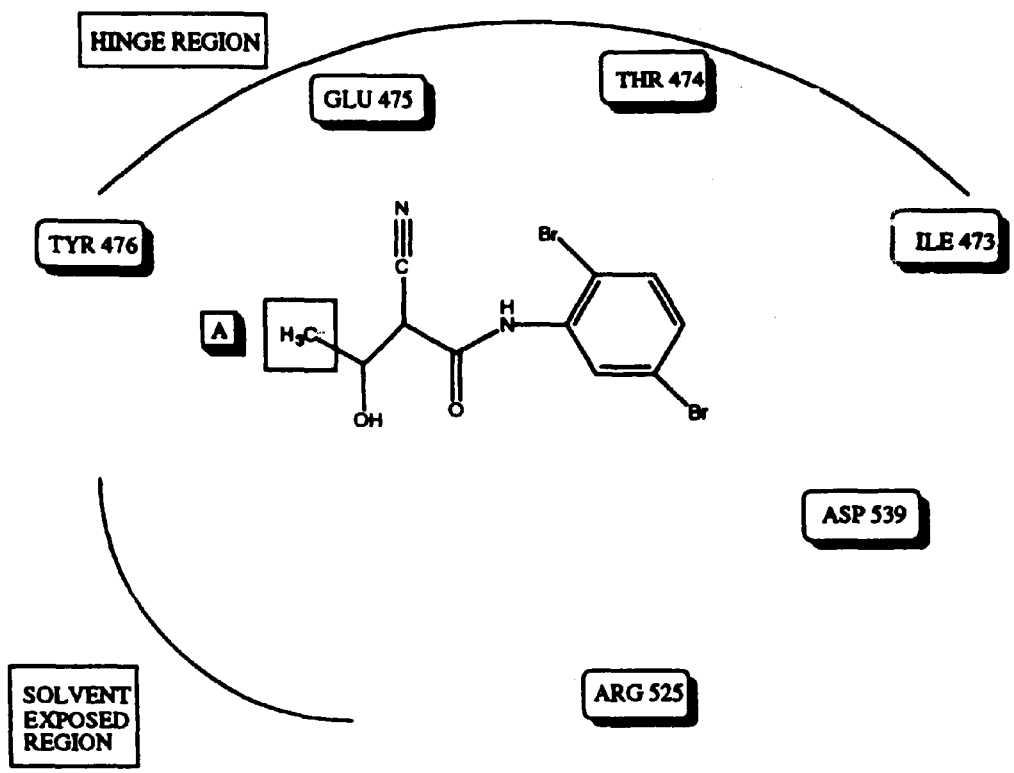
SUBSTITUTIONS AT A
  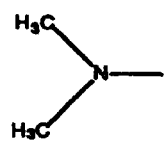
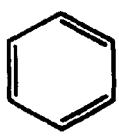  X = F, Cl, Br, CF3, OCF3

FIG. 21
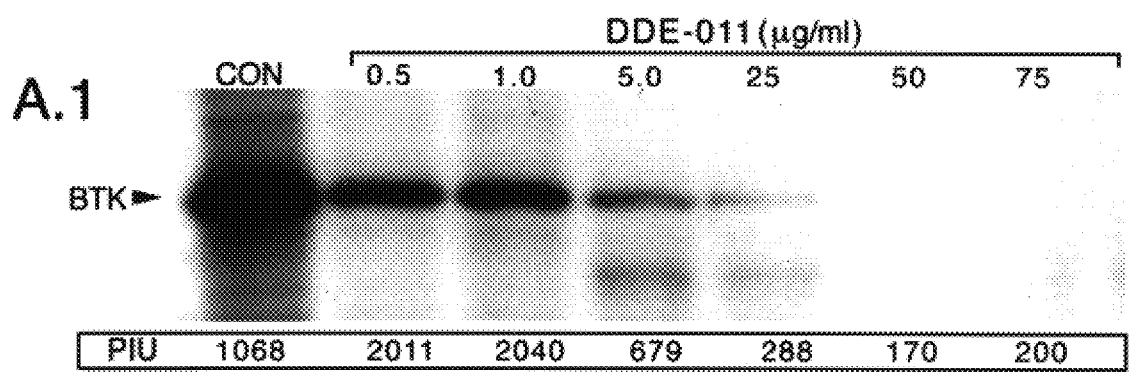
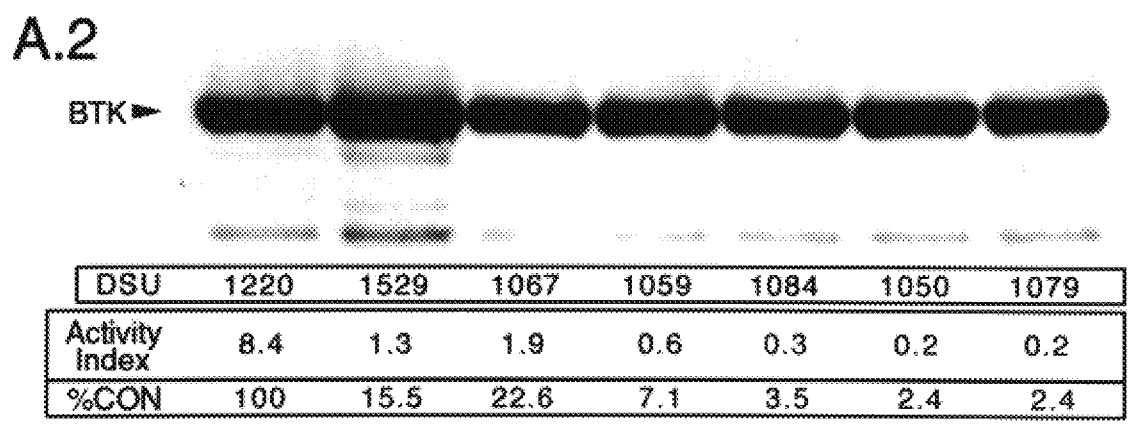

FIG. 22A
FIG. 22B
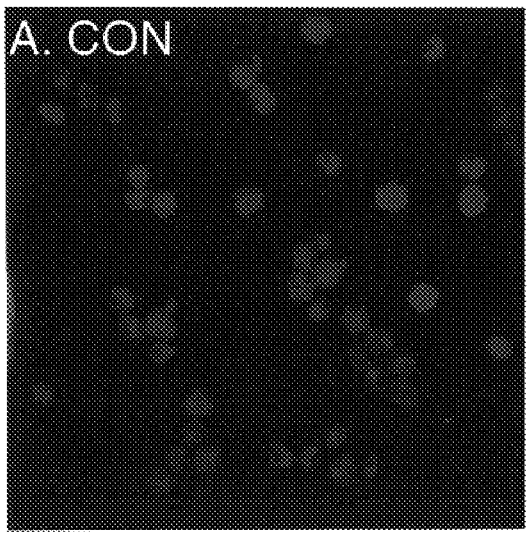
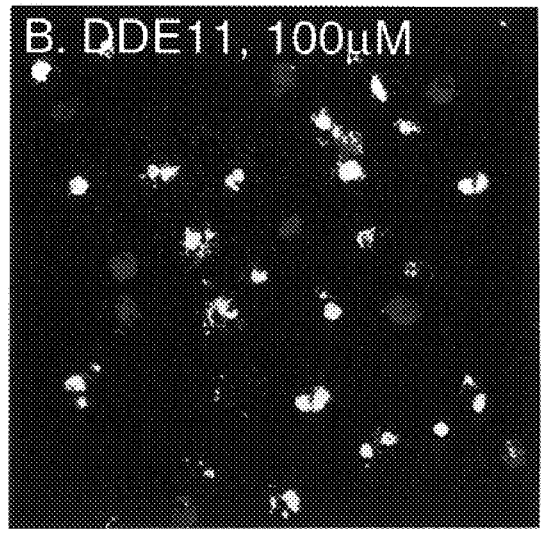

C. CON

D. DDE-11

CON

C2-CER

VCR

FIG. 23D
FIG. 23E
FIG. 23F
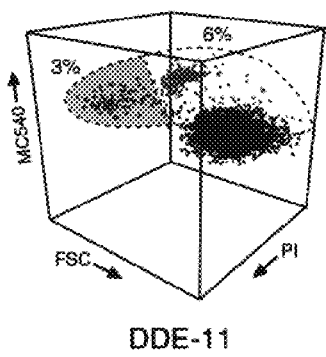
DDE-11
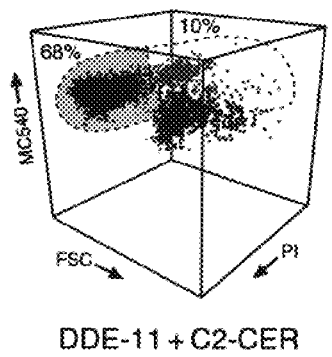
DDE-11+C2-CER
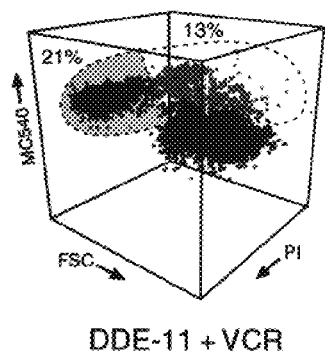
DDE-11+VCR

FIG. 25A
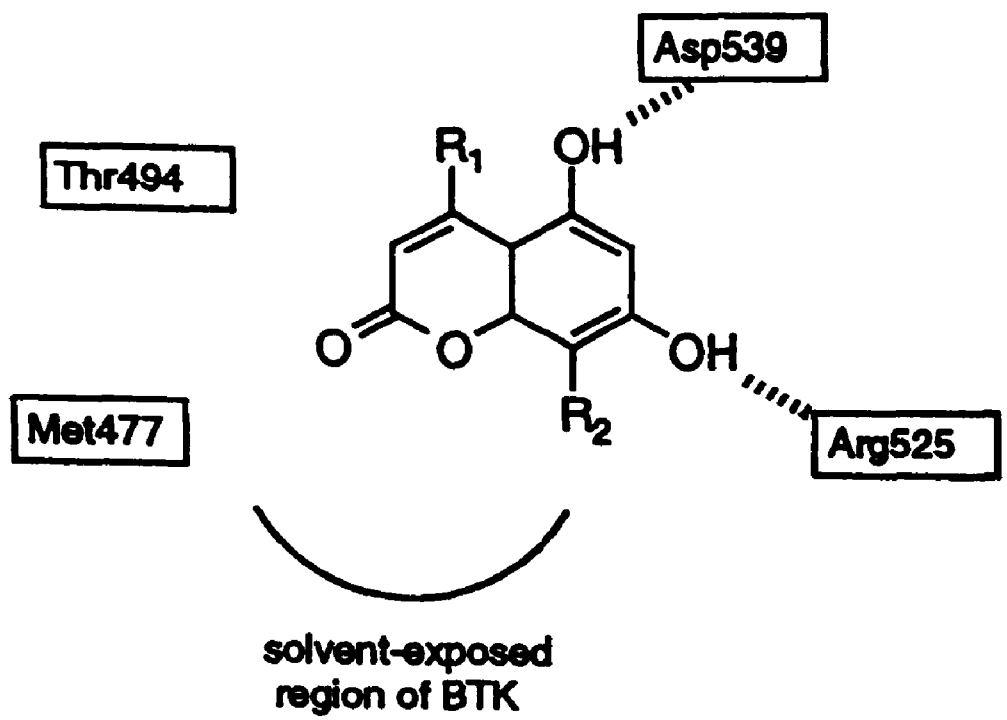
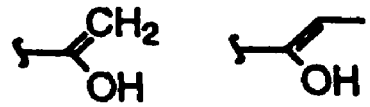
solvent-exposed region of BTK
R1 = ethyl, n-propyl, i-propyl, sec-butyl, $CH_2OH$, OH, phenyl, 3'-hydroxyphenyl,
R2 = H, $CH_2OH$,
A

B

FIG. 26A
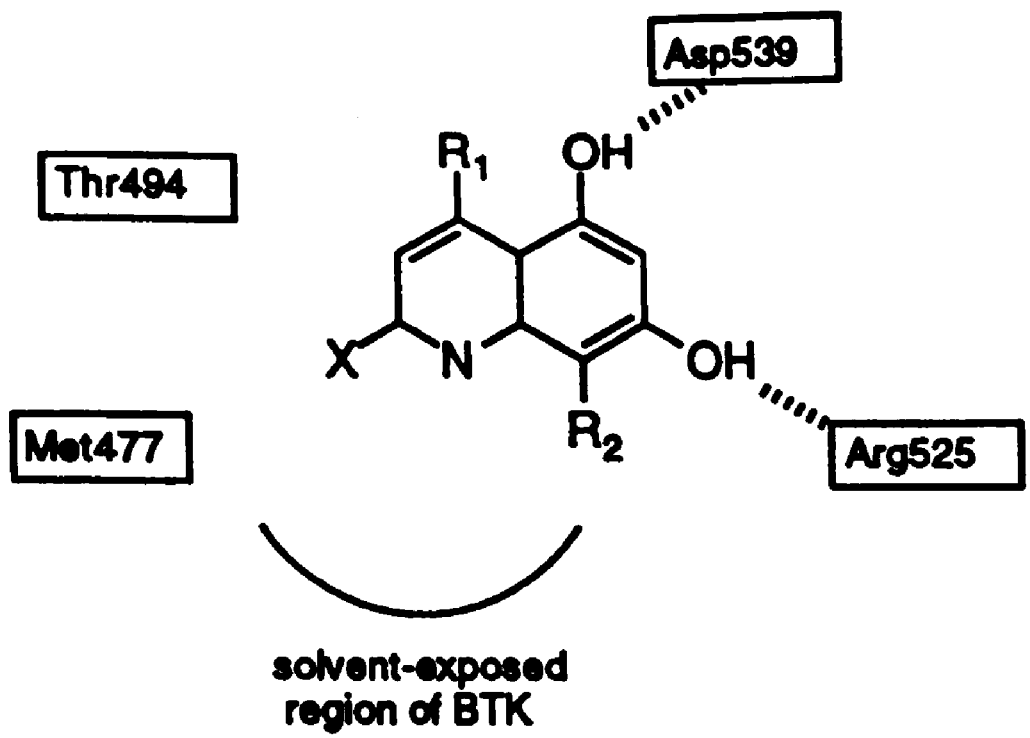
solvent-exposed region of BTK
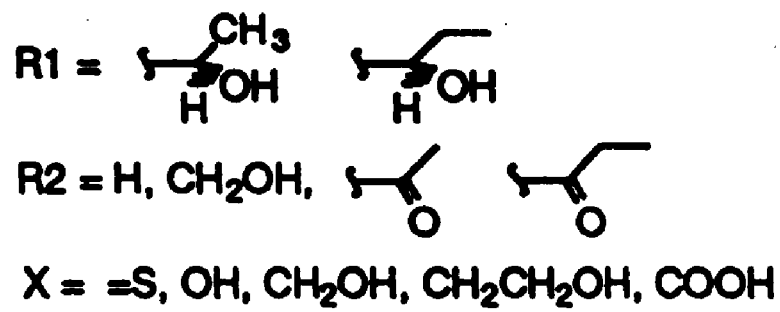
A

FIG. 26B
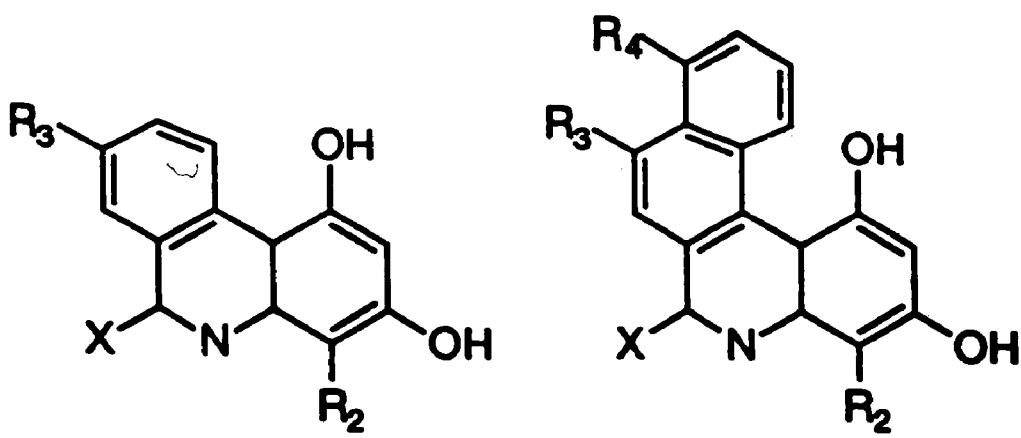
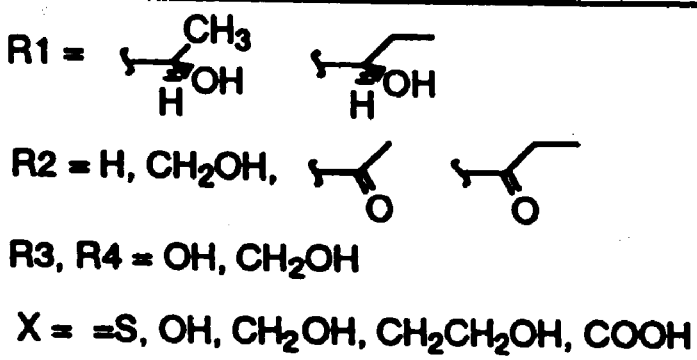
B

BTK INHIBITORS AND METHODS FOR THEIR IDENTIFICATION AND USE

This application is a Continuation of application Ser. No. 09/273,191 filed Mar. 19, 1999 which application(s) are incorporated herein by reference.

PRIORITY OF INVENTION

This application claims priority under 35 U.S.C. §119(e) from U.S. Provisional Patent Application No. 60/097,360, filed Aug. 21, 1998.

FIELD OF THE INVENTION

This invention relates to inhibitors of the family tyrosine kinase, and particularly, inhibitors of Bruton's Tyrosine Kinase (BTK).

BACKGROUND OF THE INVENTION

Apoptosis is a common mode of eukaryotic cell death which is triggered by an inducible cascade of biochemical events leading to activation of endonucleases that cleave the nuclear DNA into oligonucleosome-length fragments. Several of the biochemical events that contribute to apoptotic cell death as well as both positive and negative regulators of apoptosis have recently been identified (Whyllie A., et al. (1980) *Int. Rev. Cytol.* 68, 251–305; Steller H., (1995) *Science* 267, 1445–1449; Fraser, A., Evan, G. (1996) *Cell* 85, 781–784; and Korsmeyer, S. J. (1995). *Trends Genet.* 11, 101–105). Apoptosis plays a pivotal role in the development and maintenance of a functional immune system by ensuring the timely self-destruction of autoreactive immature and mature lymphocytes as well as any emerging target neoplastic cells by cytotoxic T cells.

In addition to the beneficial effects associated with apoptosis, inappropriate apoptosis contributes to the pathogenesis and drug resistance of human leukemias and lymphomas (Cohen. J. J., et al. (1992) *Annu. Rev. Immunol.* 10, 267–293; Linette, G. P., Korsmeyer, S. J. (1994) *Curr. Opin. Cell Biol.* 6, 809–815; and Thompson, C. B. (1995) *Science* 367, 1456–1462). Thus, agents that are useful to modulate apoptosis are potentially useful as therapeutic agents for treating diseases in which inappropriate apoptosis is implicated. As a result, there is a considerable amount of ongoing research devoted to the identification of molecular regulators of apoptosis, and there is currently a need for novel agents (e.g. chemical or biological), and novel therapeutic methods, that are useful for modulating apoptosis. Such agents and methods may be useful for treating cancer (e.g. leukemias and lymphomas) or immune disorders in mammals. They may also be useful as pharmacolocical tools for use in in vitro or in vivo studies to enhance the understanding of the molecular basis of apoptosis (e.g. the pro-apoptotic versus the anti-apoptotic regulatory signal), as well as the pathogenesis of human lymphoid malignancies.

SUMMARY OF THE INVENTION

The inventino provides inhibitors of Tec family tyrosine kinases, and particularly of BTK. The inhibitors of the invention are useful in the treatment of pathologic conditions involving cells expressing Tec family tyrosine kinaes, such as T cells (Tec, Itk) and B cells (BTK).

The invention provides compounds of formula I:

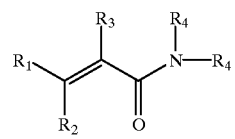

(I)

where:
R$_1$ is (C$_1$–C$_3$)alkyl, (C$_3$–C$_6$)cycloalkyl, phenyl, or NR$_a$R$_b$;
R$_2$ is hydroxy, (C$_1$–C$_6$)alkoxy, (C$_1$–C$_6$)alkanoyloxy amino (C$_2$–C$_5$)alkoxy; hydroxy (C$_2$–C$_5$)alkoxy amino (C$_2$–C$_5$)alkanoxy; or hydroxy (C$_2$–C$_5$) alkanoxy;
R$_3$ is cyano or (C$_1$–C$_3$)alkanoyl;
R$_4$ is hydrogen, (C$_1$–C$_3$)alkyl; hydroxy (C$_2$–C$_5$)alkyl; or amino (C$_2$–C$_5$)alkyl;
R$_5$ is aryl, or heteroaryl;
R$_a$ and R$_b$ are each independently hydrogen, or (C$_1$–C$_3$) alkyl; or R$_a$ and R$_b$ together with the nitrogen to which they are attached are pyrrolidino, piperidino, morpholino, or thiomorpholino;
wherein any aryl, or heteroaryl of R$_1$ and R$_5$ is optionally substituted with one or more (e.g. 1, 2, or 3) substituents independently selected from halo, nitro, cyano, hydroxy, trifluoromethyl, trifluoromethoxy, (C$_1$–C$_3$) alkoxy, (C$_1$–C$_3$)alkyl, (C$_1$–C$_3$)alkanoyl, —S(O)$_2$R$_c$, or NR$_a$R$_b$; wherein R$_c$ is (C$_1$–C$_3$)alkyl, or aryl or a pharmaceutically acceptable salt thereof;
provided that if R$_5$ is phenyl, the phenyl is substituted by —S(O)$_2$R$_c$, or is substituted by halo and at least one other substituent.

The invention also provides a compound of formula II:

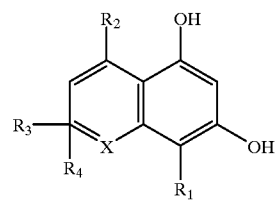

(II)

where:
X is O, N, or S;
R$_1$ is H, alkyl, carboxyl, preferably C$_1$–C$_3$ alkyl or C$_1$–C$_3$ carboxyl; and
R$_2$ is alkyl, preferably C$_1$–C$_6$ alkyl.

The compounds of the invention are designed to fit a composite binding pocket model of the BTK domain, having a molecular volume of less than the volumne of the binding pocket (e.g., less than about 600 Å$^3$) and preferably a volume that approaches ⅔ the volume of the pocket, e.g., approximately 400 Å$^3$. Most preferably, the inhibitors of the invention are designed to fille the space of the binding pocket and to interact with residues of the pocket for enhanced binding.

The invention also provides a pharmaceutical composition comprising an agent that inhibits or prevents the action of Bruton's tyrosine kinase; and a pharmaceutically acceptable carrier.

The invention also provides a method to promote or induce apoptosis in a BTK expressing cell comprising contacting the cell with an agent that inhibits or prevents the action of BTK.

The invention also provides a method to treat a disease (pathologic condition) wherein BTK is implicated and inhibition of its action is desired comprising administering to a mammal in need of such treatment an effective amount of an agent that inhibits or prevents the action of BTK.

The invention also provides a method to lower the resistance of a BTK expressing cell to drug therapy comprising contacting the cell with an agent that inhibits or prevents the action of BTK.

The invention provides a BTK inhibitor for use in medical therapy (preferably for use in treating cancer or other BTK mediated diseases), as well as the use of a compound of formula I for the manufacture of a medicament for the treatment of a pathological condition or symptom in a mammal, such as a human, which is associated with BTK (e.g. cancer, such as a leukemia or a lymphoma).

BRIEF DESCRIPTION OF THE FIGURES

FIG. 2A shows the expression levels of BTK and ACTIN in wild-type, BTK-deficient, and human btk gene-reconstituted BTK-deficient DT-40 cells were measured by Western blot analysis using appropriate monoclonal antibodies and the ECL chemiluminescence detection system (Amersham Life Sciences, used according to the manufacturer's recornmendations) (Dibirdik, I., et al. (1998) *J. of Biol. Chem.*, 273, 4035–4039; and Uckun, F. M., et al. (1997) *Blood*, 89, 3769–3777). FIG. 2B shows membranes immunoblotted with anti-BTK and anti-ACTIN antibodies that were stripped and reblotted with the monoclonal anti-Fas antibody to compare the Fas protein expression levels in the individual clones. FIG. 2C hows Fas expression levels of WT and BTK-deficient DT-40 cells examined by confocal microscopy. Green: anti-Fas labeling; Blue: Toto-3 stained DNA in nucleus; Scale Bar=10 mm.

FIG. 3A is a photograph showing wildtype cells (WT) and BTK-deficient (BTK-) DT-40 cells were treated for 24 hours with 1 μg/ml anti-Fas, co-stained with a rabbit polyclonal anti-tubulin antibody (green fluorescence) and the DNA specific dye toto-3 (blue fluorescence), and examined by laser scanning confocal microscopy, as described in the Examples. Unlike WT cells, the majority of BTK-cells show apoptotic changes including nuclear fragmentation (a,b,d) and shrinkage (c). Bar=10 mm. FIG. 3B is a DNA gel showing WT and BTK-DT-40 cells exposed to anti-Fas antibody as detailed in the Examples, harvested and DNA from Triton-X-100 lysates was analyzed for fragmentation, as described (Uckun, F. M., et al. (1996) *Science* 273, 1096–1100). FIGS. 3C and 3D show BTK-deficient DT-40 cells reconstituted with wild-type (rWT), kinase domain mutant (rK-), SH2-domain mutant (rmSH2), or PH-domain mutant (rmPH) forms of the human btk gene were examined for sensitivity to anti-Fas antibody-induced apoptosis as described in the Examples. Controls were treated with PBS in culture medium for 24 hours at 37° C. and 5% $CO_2$ prior to harvesting.

FIGS. 4A–4C: Anti-apoptotic properties of BTK confirmed by BTK protein reconstitution of BTK-DT40 cells. Maltose binding protein (MBP) or MBP-BTK were electroporated into BTK-DT-40 cells prior to treatment with anti-Fas antibody, as described in the Examples. FIG. 4A is a photograph showing MBP-BTK-electroporated BTK-deficient DT-40 cells and non-electroporated BTK-deficient DT-40 cells labeled with an antibody raised against MBP. The secondary antibody was a FITC-conjugated goat anti-rabbit antibody. Cells were analyzed using a Bio-Rad MRC-1024 Laser Scanning Confocal Microscope Digital images were processed using Adobe Photoshop software and printed using a Fuji Pictrography Printer. There was no significant staining above background in control non-electroporated cells (FIG. 4A.1). Arrowheads indicate MBP antibody reactive material in the cytoplasm of cells electroporated with the MBP-BTK fusion protein (FIG. 4A.2). Two populations were observed in the MBP-BTK electroporated cells. Some cells had very bright labelling at the periphery of the cell, while other cells had large punctate staining inside the cytoplasm. Green=MBP, Bar=10 mm. FIG. 4B shows a Western blot. Lysates as well as supernatants of BTK-deficient DT-40 cells electroporated with either MBP or MBP-BTK were subjected to Western blot analysis using anti-BTK and anti-MBP antibodies as described in Experimental Procedures. The 115 kDa MBP-BTK fusion protein reactive with both antibodies was detected only in lysates (but not supernatants) from MBP-BTK electroporated cells. FIG. 4C is a gel cells were harvested 24 hours after exposure to anti-Fas antibody and DNA from Triton-X-100 lysates was analyzed for fragmentation, as escribed by Uckun, F. M., et al. (1996) *Science* 273, 1096–1100; and Uckun, F. M., et al. (1995) *Science* 267, 886–91). Anti-Fas treatment induced apoptosis in BTK deficient cells but not in WT cells or BTK deficient cells into which MBP-BTK was electroporated. Electroporation of MBP (negative control) had no effect on apoptosis.

FIG. 7B shows anti-BTK (B. 1) and anti-Fas (B.2) Western blot analysis of Fas immune complexes from BTK-, rBTK[WT] cells with (Lane 1) or without (Lane 2) anti-Fas antibody pretreatment and from BTK-, rBTK[K-] cells with (Lane 3) or without (Lane 4) anti-Fas antibody pretreatment. The immune complexes immunoprecipitated from Nonidet P-40 whole cell lysates were collected, washed, boiled in 2×SDS sample buffer, fractionated on 12.5% polyacrylamide gels, transferred to an Immobilon-PVDF membrane, and examined for the presence of BTK and Fas proteins by immunoblotting, as described in the Methods.

FIG. 8A shows schematic diagrams of full-length and truncated MBP- and GST-fusion proteins corresponding to various domains of BTK. The inclusive amino acid (AA) sequence is indicated for each truncation mutant. BTK 1–659, BTK 408–659, BTK 2–137, as well as BTK 519–567 containing Y551 transphosphorylation site within the catalytic domain (used as a control) were fused to MBP. BTK 219–377, BTK 281–377 and BTK 219–268 were fused to GST. FIG. 8B shows MBP-BTK and GST-BTK fusion proteins (7.5 μg/lane) analyzed by SDS-PAGE using 12% polyacrylamide gels and visualized by staining of the gels with Coomassie R-250 Blue. FIG. 8C is a Western blot analysis of purified BTK from proteins corresponding to the kinase-(BTK 408–659), PH-(BTK 2–137) and $SH_2$–$SH_3$-domains (BTK 219–377) of BTK using domain-specific antibodies, as described in the Experimental Procedures. FIGS. 8D–8F demonstrate functional roles for the kinase and PH domains of BTK in BTK-Fas interactions. [FIG. 8D] BTK-deficient DT-40 chicken Iymphoma B-cells; [FIG. 8E] human NALM-6 pre-B leukemia cells; [FIG. 8F]: KL2 human EBV-transformed lymphoblastoid cells. MBP-BTK and GST-BTK fusion proteins were used in pull-down binding assays to examine their ability to interact with Fas in BTK deficient DT-40 cells, as described in the Examples. Fusion protein adsorbates and control samples $C_1$–$C_5$ (C1 (=CON): Cell lysate+amylose beads (no fusion protein added); $C_2$: Cell lysate+glutathione-agarose beads (no fusion protein added); $C_3$: MBP-BTK 1–659+amylose beads (no cell lysate); $C_4$: GST-BTK 219–268+glutathione-agarose beads (no cell lysate added); $C_5$: MBP-BTK 519–567+amylose beads+cell lysate) were resolved by SDS-PAGE, immunoblotted with the monoclonal anti-Fas antibody, and developed with ECL.

FIG. 10A is a ribbon representation of the homology model of the BTK kinase domain. The LFM-A13 molecule is shown as a space filling model in the catalytic site of BTK. Prepared using Molscript and Raster3D programs (Bacon, D. J., and Anderson, W. F. (1988) *J. Molec. Graphics* 6, 219–20; Kraulis, P. (1991) *J. Appl. Cryst.* 24, 946–50; and Merritt, E. A., and Murphy, M. E. P. (1994) *Acta Cryst.* D50, 869–73). FIG. 10B is a space filling representation of the backbone of the catalytic site residues of the BTK kinase domain. The C-alpha chain of BTK is represented as a blue ribbon. Shown in yellow, green, pink, and blue are the residues at the four corners of the rectangular shaped binding pocket. A ball and stick model of the BTK inhibitor LFM-A13 is shown in multicolor and represents the favorable orientation of this molecule in the kinase active site of BTK. Prepared using Insightll program ((1996), Molecular Simulations, Inc., San Diego, Calif.).

FIG. 17: Effects of LFM-A13 on Ceramide-Sensitivity of Human Leukemia Cells. FACS correlated three-parameter (FSC, forward scatter=size; fluorescence from PI, propidium iodide, and fluorescence from MC540 staining) displays of ALL-1 Ph/t(9;22)+ human ALL cells stained with MC540 and PI 24 hours after treatment with vehicle (0.1% DMSO in PBS), C2-Ceramide (C2-CER) (10 $\mu$M), LFM-A13 (200 $\mu$M) or LFM-A13+C2-CER. The percentages indicate the fraction of cells at an early stage of apoptosis, as measured by single MC540 fluorescence, and the fraction of cells at an advanced stage of apoptosis, as measured by dual MC540/PI fluorescence.

FIGS. 20A–20C: Illustrate the binding interactions of LFM-13 with the BTK binding pocket.

FIG. 21: Effects of DDE11 on the Tyrosine Kinase Activity of BTK. A highly purified (>90%) preparation of BTK produced in a baculovirus vector expression system was treated for 1 hour at room temperature with DDE11 at the indicated concentrations. The enzymatic activity of BTK was determined by measuring autophosphorylation in a 10 minute kinase assay, as described hereinbelow.

FIGS. 22A–22D: FIG. 22A shows data from TUNNEL assay control; FIG. 22B shows data for DDE11 at a concentration of 100 $\mu$M; FIG. 22C shows flow cytometric assay in NALM-6 cells; FIG. 22D shows flow cytometric assay data for DDE11 in NALM-6 cells showing that DDE11 induces apoptosis.

FIGS. 25A–25B: Show novel inhibitor designs based on docking the compounds into the ATP binding site of BTK. Residues shown in FIG. 25A are located in the AtP binding site and can interact with functional groups of an inhibitor. Representative compounds are shown in FIG. 25B.

FIGS. 26A–25B: Show additional novel compounds designed to better fit the BTK-1 ATP binding pocket. Suggested compounds are shown in FIG. 25B. These compounds are expected to have potent BTK inhibitory activity.

DETAILED DESCRIPTION OF THE INVENTION

Figure 1A:
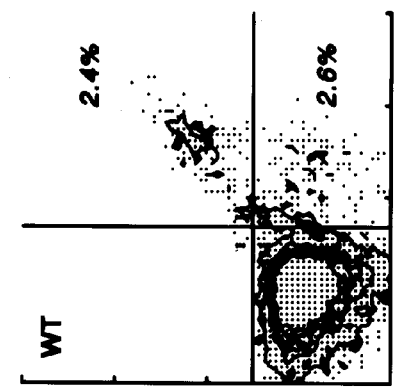
FIG. 1: BTK is an inhibitor of Fas-mediated apoptosis in DT-40 lymphoma B cells. FACS correlated two-parameter displays of wild-type (WT), BTK-deficient (BTK-), LYN-deficient (LYN-) DT-40 cells as well as BTK-deficient DT-40 cells reconstituted with wild-type human btk gene (BTK; rBTK[WT]) stained with MC540 and PI 24 hours after treatment with the control mouse IgG MsIgG (1 μg/mL) or anti-Fas (1 μg/mL). The percentages indicate the fraction of cells at an early stage of apoptosis, as measured by single MC540 fluorescence, and the fraction of cells at an advanced stage of apoptosis, as measured by dual MC540/PI fluorescence (Uckun, F. M., et al. (1996) *Science* 273, 1096–1100).
Figure 1B:
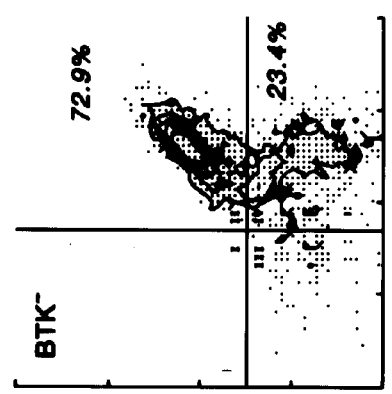
Figure 1C:
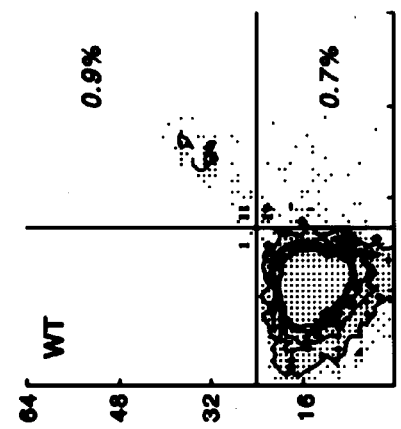
Figure 1D:
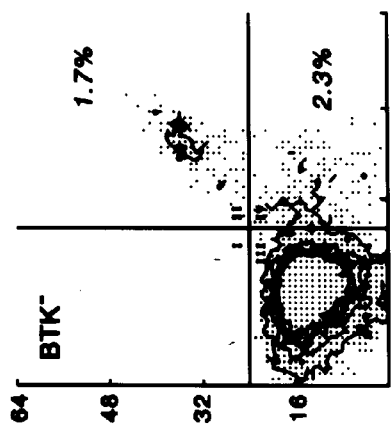
Figure 1F:
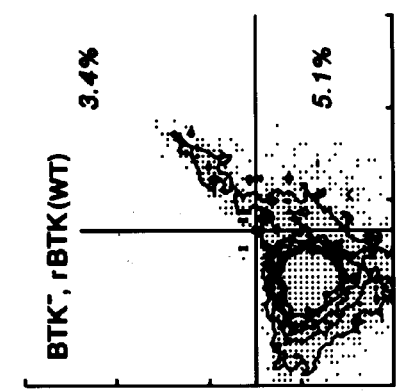
Figure 1H:
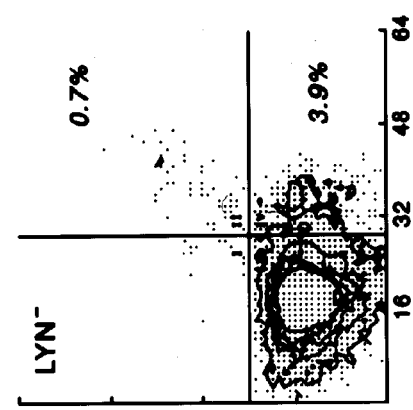
Figure 1E:
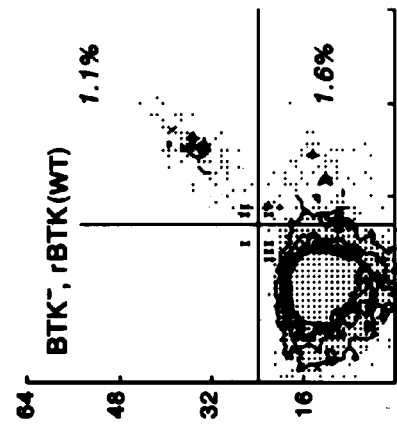
Figure 1G:
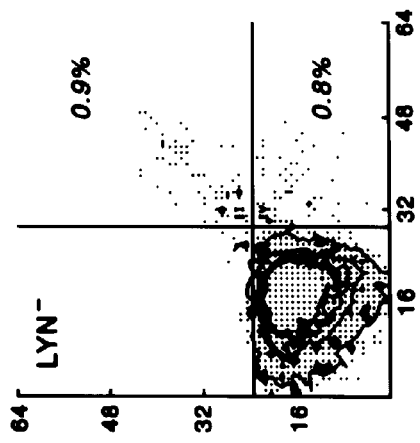

The Fas/APO-1 (CD95) cell surface receptor, a member of the tumor necrosis factor (TNF) receptor family, is one of the major regulators of apoptosis in a variety of cell types. Functional abnormalities of Fas have been associated with pathologic conditions of the immune system homeostas is, including lymphoproliferative disorders, immunodeficiencies and autoimmunity (Rieux-Laucat, et al. (1995) Science 268, 1347–1349; and Fischer, G. H. (1995) Cell 81, 935–946). Ligation of the cell surface Fas molecule rapidly and dramatically induces apoptosis in many but not all Fas positive cell types (Nagata, S. (1997) Cell 88, 355–365). DT-40 is a chicken lymphoma B-cell line that has been used to elucidate the molecular mechanism of radiation-induced apoptosis (Uckun, F. M., et al. (1996) Science 273, 1096–1100). Despite their abundant surface expression of Fas, DT-40 cells, similar to human B-cell precursor leukemia cells, are resistant to the cytotoxic effects of Fas-ligation, indicating the existence of potent negative regulators of Fas-mediated apoptosis. Bruton's tyrosine kinase (BTK), a member of the BTK/Tec family of protein tyrosine kinases (PTKs) is a cytoplasmic PTK involved in signal transduction pathways regulating growth and differentiation of B-lineage lymphoid cells (Rawlings, D. J., and Witte, O. N. (1994) Immunol. Rev. 138, 105–119; Kurosaki, T. (1997) Curr Opin. Immunol. 9, 309–318; and Uckun, F. M. (1998) Biochemical Pharmacology, et al., 56, 683–691). BTK participates in signal transduction pathways initiated by the binding of a variety of extracellular ligands to their cell surface receptors: following ligation of B cell antigen receptors (BCR), BTK activation by the concerted actions of the PTKs Lyn and Syk (Kurosaki, T. (1997) *Curr Opin. Immunol.* 9, 309–318) is required for induction of phospholipase C-γ2 mediated calcium mobilization (Kurosaki, T. (1997) *Curr Opin. Immunol.* 9, 309–318). Mutations in the human BTK gene are the cause of X-linked agammaglobulinemia (XLA), a male immune deficiency disorder characterized by a lack of mature, immunoglobulin producing, peripheral B cells (Tsukada, S., et al. (1993) *Cell* 72, 279–290; and Vetrie, D., et al. (1993) *Nature* 361, 226–233). In mice, mutations in the BTK gene have been identified as the cause of murine X-linked immune deficiency (Xid) (Rawlings, D. J., et al. (1993) *Science* 261, 358–361).

BTK has been shown to be an inhibitor of the Fas/APO-1 death inducing signaling complex (DISC) in B-lineage lymphoid cells (Vassilev, A., et al. (1998) *J. Biol. Chem.*, 274, 1646–1656). Additionally, it has presently been determined that BTK prevents ceramide- and vincristine-induced apoptosis (present study). The fate of leukemia/lymphoma cells may reside in the balance between the opposing proapoptotic effects of caspases activated by DISC and an upstream anti-apoptotic regulatory mechanism involving BTK and/or its substrates (Vassilev, A., et al. (1998) *J. Biol. Chem.*, 274, 1646–1656). Inhibitors of BTK are likely to enhance the drug sensitivity of B-lineage (e.g. leukemia/lymphoma) cells. Thus, pharmacological agents with BTK-modulatory activity can be used as chemosensitizing agents for treating BTK-expressing malignancies or diseases caused by proliferation and antibody production of BTK-expressing B-cells, and as B-cell reconstituting agents in humoral immunodeficiencies with decreased numbers or absence of B-cells. Further BTK modulating agents would be useful as immunosuppressive agents for prevention of hyperacute rejection of organs in transplantation, which is directed by B-cells, autoimmune diseases, and conversion of immunity to drugs (e.g. antibodies or biologicals) or blood products (e.g. coagulation factors such as Factor VIII) in patients who develop antibodies to such agents.

Identification of Inhibitors of BTK

The potent and selective BTK inhibitor LFM-13 and other BTK inhibitors were identified using the three-dimensional homology model of the kinase domain desribed in Example 2. Using this model and the size and contact information provided in Examples 1 and 3, additional BTK inhibitors were designed and tested. Using this model and method, other compounds that interact favorably with the binding pocket can be identified, as well as compounds that will bind selectively to BTK over other related kinases. Tight binding or a good fit in the binding pocket model correlates with potent BTK-inhibitory activity.

The ability of an agent to inhibit the anti-apoptotic effects of BTK can be measured using assays which are known in the art, or using the assays disclosed in the Examples hereinbelow. Thus, using the modeling information and the screens described herein, as well as other information known in the art, one can identify agents that possess BTK inhibiting properties.

Inhibitors of BTK also include those inhibitors produced by recombinant DNA methods, such as antisense molecules and transcription inhibitors. Initial studies on btk transcription have demonstrated that expression of the btk gene is regulated by the combined action of Sp1-and PU.1-family transcription factors (S. Muller et al. *Oncogene*, 1996, 13, 1955–1964; and A. Himmelmann et al. *Blood*, 1996, 87, 1036–1044). Transcriptional regulatory elements have been identified within the first and tenth introns of the btk gene, and recent studies indicate that regulation of btk gene expression involves multiple transcription factors (J. Rohrer, M. E. Conley, *Blood*, 1998, 91, 214–221). New agents affecting the activity of these transcription factors would also be useful as modulators of apoptotic signals in treatment programs. The feasibility of regulating btk gene expression in human hematopoietic cells has been already been demonstrated by the ability of retinoic acid to increase btk expression in myeloid cells, and by the ability of phorbol ester as well as TGF-1 to decrease btk expression in B-cells (C. I. E. Smith et al., *J. Immunol*, 1994, 152, 557–565).

Thus, one or more of the recombinant DNA methods can be used to inhibit BTK expression and induce the therapeutic effects discussed herein. Such methods include, for example, antisence sequences of transcription inhibitors. For example, BTK antisense constructs may be directed against BTK expression directly. Alternatively, the antisense construct may be directed against BTK egulatory sequences, e.g., antisense sequences to the Sp1 and PU.1 family of transcription factors. Preferably, the antisense constructs are targeted to tumor cells.

Compounds of the Invention:

Compounds of the invention are specific BTK inhibitors which bind favorably to the BTK model pocket described in the examples, and have potent BTK inhibitory activity. Compounds of the invention include compounds of formulae I and II.

The invention provides compounds of formula I:

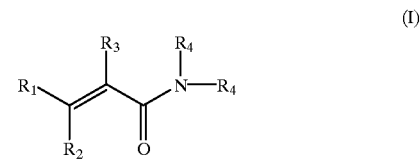

where:

$R_1$ is $(C_1–C_3)$alkyl, $(C_3–C_6)$cycloalkyl, phenyl, or $NR_aR_b$;

$R_2$ is hydroxy, $(C_1–C_6)$alkoxy, $(C_1–C_6)$alkanoyloxy amino $(C_2–C_5)$alkoxy; hydroxy $(C_2–C_5)$alkoxy amino $(C_2–C_5)$alkanoxy; or hydroxy $(C_2–C_5)$ alkanoxy;

$R_3$ is cyano or $(C_1–C_3)$alkanoyl;

$R_4$ is hydrogen, $(C_1–C_3)$alkyl; hydroxy $(C_2–C_5)$alkyl; or amino $(C_2–C_5)$alkyl;

$R_5$ is aryl, or heteroaryl;

$R_a$ and $R_b$ are each independently hydrogen, or $(C_1–C_3)$ alkyl; or $R_a$ and $R_b$ together with the nitrogen to which they are attached are pyrrolidino, piperidino, morpholino, or thiomorpholino;

wherein any aryl, or heteroaryl of $R_1$ and $R_5$ is optionally substituted with one or more (e.g. 1, 2, or 3) substituents independently selected from halo, nitro, cyano, hydroxy, trifluoromethyl, trifluoromethoxy, $(C_1–C_3)$ alkoxy, $(C_1–C_3)$alkyl, $(C_1–C_3)$alkanoyl, $—S(O)_2R_c$, or $NR_aR_b$; wherein $R_c$ is $(C_1–C_3)$alkyl, or aryl or a pharmaceutically acceptable salt thereof;

provided that if $R_5$ is phenyl, the phenyl is substituted by $—S(O)_2R_c$, or is substituted by halo and at least one other substituent.

The invention also provides a compound of formula II:

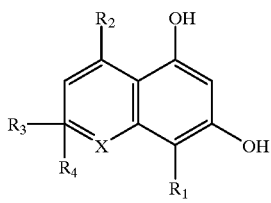

(II)

where:
X is O, N, or S;
R$_1$ is H, alkyl, carboxyl,
preferably C$_1$–C$_3$ alkyl or C$_1$–C$_3$ carboxyl; and
R$_2$ is alkyl, preferably C$_1$–C$_6$ alkyl.

Particularly useful compounds of formula I are shown on page 58:
- α-Cyano-β-hydroxy-β-methyl-N-(2,5-dibromophenyl)-propenamide;
- α-Cyano-β-hydroxy-β-methyl-N-[4-(methylsulfonyl)phenyl]-propenamide;
- α-Cyano-β-hydroxy-β-methyl-N-[3-methylsulfonyl)phenyl]-propenamide;
- α-Cyano-β-hydroxy-β-methyl-N-[3-bromo-4-(trifluoromethoxy)-phenyl]propenamide;
- α-Cyano-β-hydroxy-β-methyl-N-(2,4-dibromophenyl)-propenamide;
- α-Cyano-β-hydroxy-β-methyl-N-(2,4-dichlorophenyl)-propenamide;
- α-Cyano-β-hydroxy-β-methyl-N-(2,5-dichlorophenyl)-propenamide; or
- α-Cyano-β-hydroxy-β-methyl-N-(3,4-didichlorophenyl)-propenamide; or
- pharmaceutically acceptable salts thereof.

Particularly useful compounds of formula II are shown below on page 63.

Definitions:

The following definitions are used herein, unless otherwise described: halo is fluoro, chloro, bromo, or iodo. Alkyl, alkoxy, alkenyl, alkynyl, etc. denote both straight and branched groups; but reference to an individual isomer such as "propyl" embraces only the straight chain isomer, a branched chain isomer such as "isopropyl" being specifically referred to. Aryl denotes a phenyl group or a bicyclic or tri-cyclic carbocyclic group having about nine to twelve ring atoms in which at least one ring is aromatic. Heteroaryl encompasses a group attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, (C$_1$–C$_4$) alkyl, phenyl or benzyl, as well as a group of an ortho-fused bicyclic heterocycle of about eight to ten ring atoms derived therefrom, particularly a benz-derivative or one derived by fusing a propylene, trimethylene, or tetramethylene group thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine BTK inhibiting activity using the standard assays described herein, or using other similar assays which are well known in the art.

Specific and preferred values listed below for substituents and ranges, are for illustration only; they do not exclude other defined values or other values within defined ranges for the radicals and substituents Specifically, (C$_1$–C$_3$)alkyl can be methyl, ethyl, propyl, or isopropyl; (C$_1$–C$_4$)alkyl can be methyl, ethyl, propyl, isopropyl, butyl, iso-butyl, or sec-butyl; (C$_3$–C$_6$)cycloalkyl can be cyclopropyl, cyclobutyl, cyclopentyl, or cyclohexyl; (C$_3$–C$_6$)cycloalkyl(C$_1$–C$_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C$_1$–C$_3$)alkoxy can be methoxy, ethoxy, propoxy, isopropoxy; (C$_1$–C$_6$)alkoxy can be methoxy, ethoxy, propoxy, isopropoxy, butoxy, iso-butoxy, sec-butoxy, pentoxy, 3-pentoxy, or hexyloxy; (C$_2$–C$_6$) alkanoyloxy can be acetoxy, propanoyloxy, butanoyloxy, isobutanoyloxy, pentanoyloxy, or hexanoyloxy; (C$_2$–C$_4$) alkenyl can be vinyl, allyl, 1-propenyl, 2-propenyl, 1-butenyl, 2-butenyl, or 3-butenyl; (C$_2$–C$_4$)alkynyl can be ethynyl, 1-propynyl, 2-propynyl, 1-butynyl, 2-butynyl, or 3-butynyl; hydroxy(C$_1$–C$_4$)alkyl can be hydroxymethyl, 1-hydroxyethyl, 2-hydroxyethyl, 1-hydroxypropyl, 2-hydroxypropyl, 3-hydroxypropyl, 1-hydroxybutyl, or 4-hydroxybutyl; hydroxy(C$_2$–C$_4$)alkenyl can be 3-hydroxy-1-propenyl, 4-hydroxy-1-butenyl, or 4-hydroxy-2-butenyl; hydroxy(C$_2$–C$_4$)alkynyl can be 3-hydroxy-1-propynyl, 1-hydroxy-2-propynyl, 3-hydroxy-1-butynyl, 4-hydroxy-1-butynyl, 1-hydroxy-2-butynyl, 4-hydroxy-2-butynyl, 1-hydroxy-3-butynyl, or 2-hydroxy-3-butynyl; (C$_1$–C$_4$) alkylthio can be methylthio, ethylthio, propylthio, isopropylthio, butylthio, or isobutylthio; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specific and Preferred Values

A specific value for R$_1$ is (C$_1$–C$_3$)alkyl, or (C$_3$–C$_6$) cycloalkyl. A specific value for R$_2$ is hydroxy.

A specific value for R$_3$ is cyano.

A specific value for R$_4$ is hydrogen.

A specific value for R$_5$ is phenyl substituted with halo, and substituted with 1, 2, or 3 other substituents independently selected from halo, nitro, cyano, trifluoromethyl, trifluoromethoxy, (C$_1$–C$_3$)alkoxy, (C$_1$–C$_3$)alkyl, (C$_1$–C$_3$) alkanoyl and NR$_a$R$_b$.

A specific value for R$_6$ is methyl, trifluoromethyl, methoxymethyl, ethyl, isopropyl, tert-butyl, or propyl.

A specific value for R$_7$ is hydrogen, methyl, or ethyl.

A specific value for R$_9$ is acetyl, trifluoroacetyl, propanoyl, crclopropylcarbonyl, vinylcarbonyl, 2-propenoyl, methoxycarbonyl, methylthiocarbonyl, ethoxycarbonyl, or ethylthiocarbonyl.

A more specific value for R$_1$ is (C$_1$–C$_3$)alkyl.

A more specific value for R$_5$ is phenyl substituted with halo, and substituted with 1, 2, or 3 other substituents independently selected from halo, trifluoromethyl, trifluoromethoxy, and (C$_1$–C$_3$)alkoxy.

A more specific value for $R_5$ is phenyl substituted with 2 or 3 halo.

A more specific value for $R_5$ is phenyl substituted with two bromo.

A preferred compound of formula I is α-cyano-β-hydroxy-β-methyl-N-(2,5-dibromophenyl)propenamide; or a pharmaceutically acceptable salt thereof.

Therapeutic Use

B-cells and B-cell precursors expressing BTK have been implicated in the pathology of a number of diseases and conditions including B-cell malignancies (e.g. acute lymphoblastic leukemia, chronic lymphocitic leukemia, non-Hodgkin's lymphoma, EBV lymphomia, and myeloma), other cancers, B-cell lymphoproliferative disorders/autoimmune diseases (e.g. lupus, Crohn's disease, and chronic or graft-versus-host disease), mast cell disorders (e.g. allergies, and anaphylactic shock), conditions that relate to improper platelet aggregation, and rejection of xenotransplants (e.g. pig to human heart transplants).

Additionally, the selective BTK inhibitors of the invention can be used to identify other diseases wherein BTK plays a role, and particularly to identify gene expression that is modulated by BTK. This can be done using techniques that are known in the art, for example, using gene profiling techniques similar to those described by A. Sehgal et al. *Journal of Surgical Oncology*, 1998, 67, 234–241. Incubating cells in the presence or absence of a BTK inhibitor followed by profiling of gene expression in the cells is useful to identify BTK-regulated gene expression. Materials useful for profiling gene expression using Atlas cDNA membranes can be obtained from CLONTECH Laboratories, Inc. 1020 East Meadow Circle, Palo Alto, Calif. 94303. cDNA microarrays can also be ordered from commercial sources or be custom made.

Using such materials according to the manufacturer's instructions, it has also been to discovered that BTK modulates the expression of specific genes, for example, MAP-KAP kinase and c-myc oncogene. This activity suggests that BTK may be implicated in the pathology of all froms of cancer.

BTK is a member of the Tec family of tyrosine kinases. Tec kinase is expressed, for example, in T-cells. The BTK inhibitors of the invention are also useful to inhibit the activity of other members of the Tec kinase family.

BTK inhibitors (including compounds of formula I and II as described herein) can be used to treat disorders wherein the inhibition or prevention of a Tec family kinase, including BTK activity is indicated. It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Conjugation to a Targeting Moiety

The compounds of the invention can be targeted for specific delivery to a cell type to be treated by conjugation of the BTK inhibitor to a targeting moiety. Targeting moieties useful for conjugation to BTK inhibitors include antibodies, cytokines, and receptor ligands that are specific to the cell to be treated.

The term "conjugate" means a compound formed as a composite between two or more molecules. More specifically, in the present invention, the quinazoline derivative is bonded, for example, covalently bonded, to cell-specific targeting moieties forming a conjugate compound for efficient and specific delivery of the agent to a cell of interest.

The phrase "targeting moiety" means a molecule which serves to deliver the compound of the invention to a specific site for the desired activity. Targeting moieties include, for example, molecules that specifically bind molecules on a specific cell surface. Such targeting moieties useful in the invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

Particularly useful targeting moieties for targeting the BTK-inhibitory compounds of the invention to cells for therapeutic acitivity include those ligands present of Tec kinase expressing cells. For example, antigens present on B-cells and B-lineage cancer cells, such as CD19 can be targeted with anti-CD19 anitbodies such as B43. Antibody fragments, including single chain fragments can be used. Natural ligands for the surface antigens such as CD19 can also be used. Tec kinase expressing T cells can be targeted, for example to the CD7 antigen with anti-CD7 antibodies such as TXU. Mast cells can be targeted via the CD48 antigen with anti-CD48 antibodies. These and other cell surface anitgen antibodies are commercially avaialble, for example, from Pharmingen.

Cytokines are also useful targeting moieties. T cells can be targeted with IL2 and IL7; B cells can be targeted with IL4; mast cells can be targeted with C-KIT, MGF, GMCSF, and IL3. Cancer cells expressing Tec kinase can be targeted, for example, with EGF and IGF.

Compounds as Salts

In cases where an agent ("compound") is sufficiently basic or acidic to form stable nontoxic acid or base salts, administration of the compounds as salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Prodrug Derivatives

The compounds of the invention may have attached thereto flinctinal groups to provide a prodrug derivative. The prodrug deriviative facilitates use of the drug in the body, for example, by facilitating entry into cells. The term "prodrug moiety" is a substitution group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolized in vivo.

Pharmaceutical Formulations

A compound can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the compound or its salt can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active compound which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active compound plus any additional desired ingredient present in the previously sterile-filtered solutions.

For topical administration, the compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active compound per unit dosage form.

Ideally, the active compound should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

As disclosed herein, it has been discovered that BTK inhibitors are useful as chemosensitizing agents, and thus, are useful to increase the sensitivity of a cancer cell to other chemotherapeutic agents that promote apoptosis. As such, BTK inhibitors can conveniently be administered in combination with other chemotherapeutic agents. Additioanlly, the pharmaceutical compositions of the invention that comprise an agent that inhibits BTK, can also further comprise one or more other chemotherapeutic agents that promote apoptosis.

The invention will now be illustrated by the following non-limiting Examples

EXAMPLES

Example 1

BTK Inhibits FAS/APO-1 DISC

The following example provides biochemical and genetic evidence that BTK is an inhibitor the Fas/APO-1 death inducing signaling complex (DISC) in B-lineage lymphoid cells. BTK associates with Fas via its kinase and PH domains and prevents the FAS-FADD interaction, which is essential for the recruitment and activation of the death-inducing proteolytic enzyme FLICE by Fas during the apoptotic signal. Notably, treatment of human leukemic B-cells with a potent inhibitor of BTK abrogated the BTK-Fas association and sensitized the cells to Fas-mediated apoptosis.

Cell lines, reagents, and biochemical assays. The establishment of BTK-deficient DT-40 lymphoma B-cell clones have been previously described by Uckun, F. M., et al. (1996) Science 273, 1096–1100. To disrupt the btk gene, targeting constructs containing neomycin-resistance gene cassette (i.e., pcBTK-neo) or histidinol-resistance gene cassette (i.e., pcBTK-hisD) were sequentially transfected into DT-40 cells. The targeting vectors, pcBTK-neo and pcBTK-hisD, were constructed by replacing the 0.7 kb BglII-BamHI genomic fragment containing exons which correspond to human BTK amino acid residues 91–124 with neo or hisD cassette. pcBTK-neo was linearized and introduced into wild-type DT-40 cells by electroporation. Screening was done by Southern blot analysis using a 3' flanking probe (0.5 kb BglII-Bgl-II fragment). The neo-targeted clone was again transfected with pcBTK-hisD and selected with both G418 (2 mg/mL) and histidinol (1 mg/mL). Southern blot analysis of BTK-deficient DT-40 clone confirmed the homologous recombination at both btk loci and hybridization with a neo and hisD probe indicated that the targeted clone had incorporated a single copy of each construct. Lack of BTK expression in BTK-deficient DT-40 cells was confirmed by both immune complex kinase assays and Western blot analysis (Uckun, F. M., et al. (1996) Science 273, 1096–1100). Mutations in the human btk cDNA were introduced by PCR using Pfu polymerase (Strategene, La Jolla, Calif. #600153) and confirmed by sequencing. Wild-type and mutant btk cDNAs were subcloned into pApuro expression vector and electroporated into BTK-deficient cells. The PTK activity of BTK immune complexes, as measured by in vitro autophosphorylation, was abrogated by the catalytic domain mutation, reduced by the PH domain mutation but not affected by the mutation in the SH2 domain. Equal amounts of BTK protein were detected by Western blot analysis in all of the BTK-deficient DT-40 clones transfected with wild-type or mutated human btk genes but no BTK protein was detectable in the untransfected BTK-deficient DT-40 cells (Uckun, F. M., et al. (1996) Science 273, 1096–1100). The establishment and characterization of LYN-deficient DT-40 clones were previously reported by Uckun, F. M., et al. (1996) Science 273, 1096–1100. In addition to these chicken lymphoma B-cells, the following human B-lineage lymphoid cell lines: NALM-6-UM1, BTK-positive human B-cell precursor (pre-B acute lymphoblastic leukemia) cell line; RAMOS-1, BTK-deficient human Burkitt's/B-cell leukemia line; and KL2 BTK-positive human EBV-transformed normal B-lymphoblastoid cell lines were used.

Antibodies directed against BTK, SYK, and LYN have been described previously (Uckun, F. M., et al. (1996) Science 273, 1096–1100; Dibirdik, I., et al. (1998) J. of Biol. Chem., 273, 4035–4039; and Uckun, F. M., et al. (1996) J. Biol. Chem. 271, 6389–6397. Polyclonal antibodies to BTK were generated by immunization of rabbits with glutathione S-transferase (GST) fusion proteins (Amersham Pharmacia Biotech, Arlington Heights, Ill.) containing the first 150 amino acids of BTK. In addition, the following anti-BTK antibodies were used in Western blots of purified fusion proteins: Polyclonal goat anti-BTK carboxyl terminus (Santa Cruz Biotechnology, Inc., Santa Cruz, Calif., cat # SC1107), polyclonal goat anti-BTK amino terminus (Santa Cruz Biotechnology, Inc., Santa Cruz, Calif. cat # SC 1108,), and polyclonal rabbit serum raised against the Btk $SH_2$–$SH_3$ domains (aa219–377). Polyclonal anti-MBP antibodies were generated by immunizing rabbits. The rabbit polyclonal anti-Fas (sc-715 mixed 1:1 with sc-714) which crossreacts with both human and chicken Fas proteins, goat polyclonal anti-FADD (sc-1171), goat polyclonal anti-TRADD (sc-1163), goat polyclonal anti-FLICE (sc-6135) were purchased from Santa Cruz Biotechnology, Inc. and used according to the manufacturer's recommendations. The monoclonal anti-Fas antibody (F22120) was obtained from the Transduction Laboratories, Inc. (Lexington, Ky., USA). Immunoprecipitations, immune-complex protein kinase assays, and immunoblotting using the enhanced chemiluminescence (ECL) detection system (Amersham Pharmacia Biotech, Arlington Heights, Ill.) were conducted as described previously (Uckun, F. M., et al. (1996) Science 273, 1096–1100; Dibirdik, I., et al. (1998) J. of Biol. Chem., 273, 4035–4039; Uckun, F. M., et al. (1996) *J. Biol. Chem.* 271, 6389–6397; Mahajan, S., et al. (1995) *Mol. Cell. Biol.* 15, 5304–5311; Uckun, F. M., et al. (1993) *J. Biol. Chem.* 268, 21172–21184; Uckun, F. M., et al. (1995) *Science* 267, 886–91; and Uckun, F. M., et al. (1997)*Blood*, 89,3769–3777). The BTK inhibitor α-cyano-β-hydroxy-β-methyl-N-(2,5-dibromophenyl)propenamide (LMA-13) was prepared as described in Example 2.

Expression and Purification of MBP-BTK and GST-BTK Fusion Proteins. cDNAs encoding full-length BTK and its kinase or PH domains with PCR-generated 5' and 3' BamHI sites were cloned into the *E. coli* expression vector pMAL-C2 with the IPTG-inducible Ptac promoter to create an in frame fusion between these coding sequences and the 3' end of the *E. coli* malE gene, which codes for maltose binding protein (MBP). cDNAs encoding the SH2, SH3, or SH2+SH3 domains with PCR-generated 5' and 3' BamHI sites were cloned into the *E. coli* expression vector pGEX-2t with the IPTG-inducible Ptac promoter to create an in frame fusion between these coding sequences and the 3' end of the *E. coli* gluthatione S-transferase (GST) gene. The generated recombinant plasmids were transformed into the *E. coli* strain DH5a. Single transformants were expanded in 5 ml Luria-Burtain (LB) medium (1% tryptone, 1% NaCl, 0.5% yeast extract) containing ampicillin (100 μg/ml) by overnight culture at 37° C. Expression of the fusion proteins was induced with 10 mM IPTG. The cells were harvested by centrifugation at 4,500×g in a Sorvall RC5B centrifuge for 10 minutes at 4° C., lysed in sucrose-lysozyme buffer (20 mM Tris pH 8.0, 150 mM NaCl, 10% sucrose, 1 mM EDTA, 20 mM lysozyme), and further disrupted by sonication. After removal of the cell pellets by centrifugation at 35,000×g for 1 hour at 4° C., GST-BTK fusion proteins were purified by gluthatione-Sepharose chromatography (Uckun, F. M., et al. (1996) *J. Biol. Chem.* 271, 6389–6397), whereas MBP-BTK fusion proteins were purified from the culture supernatants by amylose affinity chromatography (Hsu, D., et al. (1996) *Biochemistry* 35, 13871–77).

Confocal Laser Scanning Microscopy. Wildtype and BTK-deficient DT-40 cells treated with anti-Fas antibody (1 μg/ml, 24 hrs at 37° C.) were attached to poly-1-lysine coated coverslips and fixed in ice cold (−20° C.) methanol for 15 minutes. After fixation, the coverslips were washed for 15 min in phosphate buffered saline (PBS)+0.1% triton X-100. Cells were stained with a rabbit polyclonal anti-tubulin antibody according to the manufacturer's recommendations (Sigma, St. Louis, Mo.) to visualize their cytoplasms. DNA was labelled for 10 min with toto-3 a DNA specific dye (Molecular Probes, Eugene Oreg.) to visualize the apoptotic changes in the nuclei. BTK-MBP electroporated BTK-deficient DT-40 cells and non-electroporated BTK-deficient DT-40 cells were labelled with an antibody raised against maltose binding protein. The secondary antibody was a goat anti-rabbit fluorescein conjugated antibody. In some experiments, cells were examined for Fas expression by confocal microscopy. In brief, cells were attached to poly-L-lysine coated coverslips and fixed for 40 min in 2% paraformaldehyde in phosphate buffered saline (PBS). Cells were rinsed in PBS+115 mM glycine to quench the formaldehyde and then blocked in PBS containing 2% bovine serum albumin (PBS+BSA). A monoclonal antibody raised against the extracellular domain of Fas (Transduction Labs, Lexington, Ky., catalog #F22120) was added in PBS+BSA and the coverslips were incubated for 40 min at 37° C. before again rinsing in PBS. A fluorescein-labeled secondary antibody (goat antimouse—FITC H+L, Zymed, South San Francisco, Calif., catalog no. 62-6511) diluted in PBS+BSA was then added to the coverslips and they were again incubated for 40 min at 37° C. After another wash, cellular DNA was labelled by incubation in 1 mM TOTO-3 (Molecular Probes, Eugene, Oreg.) for 20 min at room temperature. Coverslips were inverted and mounted onto slides in is Vectashield (Vector Labs, Burlinghame, Calif.), to prevent photobleaching and sealed with nail varnish. Slides were examined using a Bio-Rad MRC 1024 Laser Scanning Confocal Microscope mounted on an Nikon Eclipse E-800 upright microscope equipped for epifluorescence with high numerical aperture objectives (Uckun, F. M., et al. (1998) *Clinical Cancer Research*, 4, 901–912). Optical sections were obtained and turned into stereo micrographs using Lasersharp software (Bio-Rad, Hercules, Calif.). Representative digital images were saved to Jaz disk and processed using the Photoshop software (Adobe Systems, Mountain View Calif.). Images were printed with a Fuji Pictography thermal transfer printer (Fuji Photo, Elmsford, N.Y.). Digital data was archived and stored on CD-ROM.

Apoptosis Assays. To induce apoptosis, cells were treated with an agonistic anti-Fas/APO-1 antibody (Biosource International, Camarillo, Calif., lot. 04/1295) at 0.1 μg/ml, 0.5 μg/ml, or 1.0 μg/ml final concentrations. MC540 binding (as an early marker of apoptosis) and PI permeability (as a marker of advanced stage apoptosis) were simultaneously measured in DT-40 cells 24 hours after exposure to anti-Fas antibody as previously described (Uckun, F. M., et al. (1996) *Science* 273, 1096–1100). Whole cells were analyzed with a FACStar Plus flow cytometer (Becton Dickinson, San Jose, Calif.). All analyses were done using 488 nm excitation from an argon laser. MC540 and PI emissions were split with a 600 nm short pass dichroic mirror and a 575 nm band pass filter was placed in front of one photomultiplier tube to measure MC540 emission and a 635 nm band pass filter was used for PI emission.

To detect apoptotic fragmentation of DNA, DT-40, NALM-6-UM1, and RAMOS-1 cells were harvested 24 hours after exposure to anti-Fas. DNA was prepared from Triton-X-100 lysates for analysis of fragmentation (Uckun, F. M., et al. (1996) *Science* 273, 1096–1100; Uckun, F. M., et al. (1995)*Science* 267, 886–91; and Uckun, F. M., et al. (1998) *Clinical Cancer Research*, 4, 901–912) Cells were lysed in hypotonic 10 mmol/L Tris-HCl (pH 7.4), 1 mmol/L EDTA, 0.2% Triton-X-100 detergent; and subsequently centrifuged at 11,000×g. To detect apoptosis-associated DNA fragmentation, supernatants were electrophoresed on a 1.2% agarose gel, and the DNA fragments were visualized by ultraviolet light after staining with ethidium bromide. In some experiments, MBP-BTK fusion proteins (100 μg/2.5× $10^8$ cells) were electroporated (420V electrical field, 125 μF) into BTK-deficient DT-40 cells using a BioRad gene pulser and the procedures of Bergland and Starkey (Bergland, D. and Starkey, J. (1991) *Cytometry* 12, 64–67) with slight modifications 4 hours prior to Fas-ligation and apoptosis assays.

Pull Down Assays with MBP-BTK and GST-BTK Fusion Proteins.

GST-BTK fusion proteins were non-covalently bound to glutathione-agarose beads (Sigma Aldrich, Inc., St. Louis, Mo.) and MBP-BTK fusion proteins were non-covalently bound to amylose beads under conditions of saturating protein, as previously described (Uckun, F. M., et al. (1996) *J. Biol. Chem.* 271, 6389–6397; and Hsu, D., et al. (1996) *Biochemistry* 35, 13871–77). In brief, 50 μg of each protein was incubated with 50 μl of the beads for 2 hours at 4° C. The beads were washed three times with 1% Nonidet P-40 buffer. Nonidet P-40 lysates of BTK-deficient DT-40 cells, NALM-6-UM1 human leukemic B-cell precursors, and KL2 human EBV-transformed lymphoblastoid cells were prepared as described (Uckun, F. M., et al. (1996) *Science* 273, 1096–1100; and Uckun, F. M., et al. (1996)*J. Biol. Chem.* 271, 6389–6397) and 500 µg of the lysate was incubated with 50 µl of fusion-protein coupled beads for 2 hours on ice. The fusion protein adsorbates were washed with ice-cold 1% Nonidet P-40 buffer and resuspended in reducing SDS sample buffer. Samples were boiled for 5 min and then fractionated on SDS-PAGE. Proteins were transferred to Immobilon-P (Millipore, Bedford, Mass.) membranes, and membranes were immunoblotted with anti-Fas (Transduction Laboratories, Inc., Lexington, Ky., cat. # F22120), according to previously described procedures (Uckun, F. M., et al. (1996) *Science* 273, 1096–1100; Dibirdik, I., et al. (1998) *J. of Biol. Chem.*, 273, 4035–4039; Uckun, F. M., et al. (1996) *J. Biol. Chem.* 271, 6389–6397; and Uckun, F. M., et al. (1997) *Blood*, 89, 3769–3777).

Figure 2A:
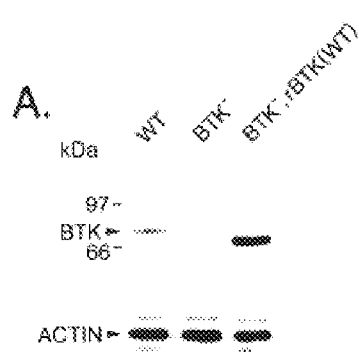
FIGS. 2A–2C: Fas protein expression levels in wild-type and BTK-deficient DT-40 cells.
Figure 2B:
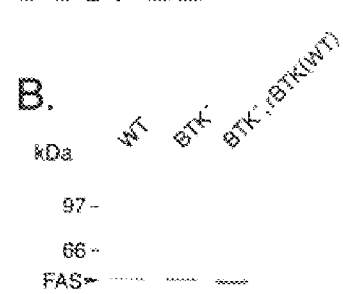
Figure 2C:
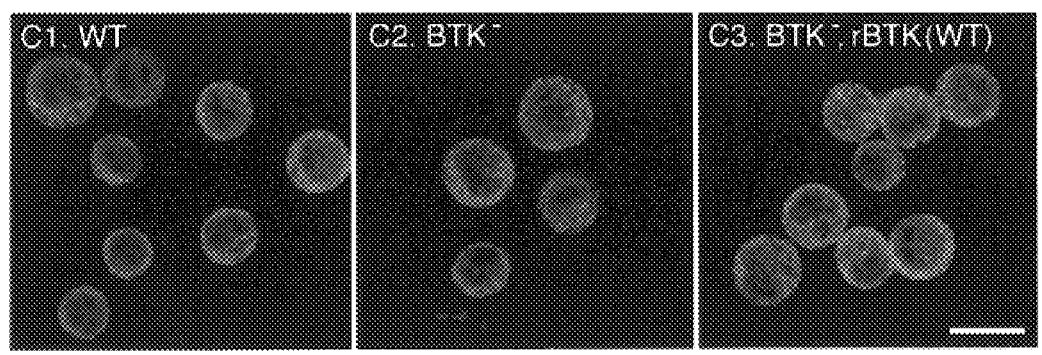

In a series of experiments designed to examine the potential negative regulatory role of BTK in Fas-mediated apoptosis, we first compared the effects of Fas-ligation on wild-type DT-40 cells to the effects of Fas-ligation on a BTK-deficient subclone of DT-40 cells that was established by homologous recombination knockout (Uckun, F. M., et al. (1996) *Science* 273, 1096–1100). To this end, we first used a quantitative flow cytometric apoptosis detection assay (Uckun, F. M., et al. (1996) *Science* 273, 1096–1100). MC540 binding and propidium iodide (PI) permeability were simultaneously measured before and after treatment with the agonistic anti-Fas antibody (1 µg/mL×24 hours). Whereas only 5.0% of wild-type DT-40 cells treated with the anti-Fas antibody showed apoptotic changes, 96.3% of BTK-deficient DT-40 cells underwent apoptosis, as determined by MC540 single fluorescence (early apoptosis) or MC540/PI double fluorescence (advanced apoptosis) at 24 hours (FIG. 1). Notably, BTK-deficient DT-40 cells reconstituted with a wild-type human btk gene displayed very little flow cytometric evidence of apoptosis, which provided formal evidence that BTK plays a pivotal role in preventing the apoptotic death signal triggered by Fas-ligation. In accordance with previously published information regarding the pro-apoptotic function of Src family PTK (Waddick, K. G., et al. (1993) *Radiation Research*, 136, 313–319; Schlottmann, K. E., et al. *Leukocyte Biology* 60, 546–554; and Atkinson, E. A., et al. (1996) *J. Biol. Chem.* 271, 5968–5971) and the reported impairment of Fas-mediated apoptosis in B-cells from LYN-deficient mice (Wang, J., et al. (1996) *J. Exp. Med.* 184, 831–838), very little apoptosis was found in an anti-Fas treated LYN-deficient subclone of DT-40 cells that was included as a control in these experiments (FIG. 1). As shown in FIG. 2A, no BTK protein was detectable by Western blot analysis in the whole cell lysates of BTK-deficient DT-40 cells, whereas BTK-deficient DT-40 cells reconstituted with a wild-type human btk gene expressed higher levels of BTK than the wild-type DT-40 cells. However, the Fas protein expression levels in these three B-cell clones were virtually identical (FIG. 2B). These findings were further confirmed by confocal microscopy. As shown in C.1 to C.3, all three cell lines exhibited similar levels of punctate Fas staining. 3-dimensional reconstructions of serial optical sections confirmed the expression of Fas both in the cytoplasm and on the surface membrane of all 3 cell lines without any detectable differences relative to expression levels or pattern. Thus, the resistance of wild-type DT-40 cells or BTK-deficient DT-40 cells reconstituted with wild-type BTK against Fas-mediated apoptosis was not due to lower expression levels of Fas protein and the susceptibility of BTK-deficient DT-40 cells to Fas-mediated apoptosis was not caused by augmented Fas protein expression.

Figure 3A:
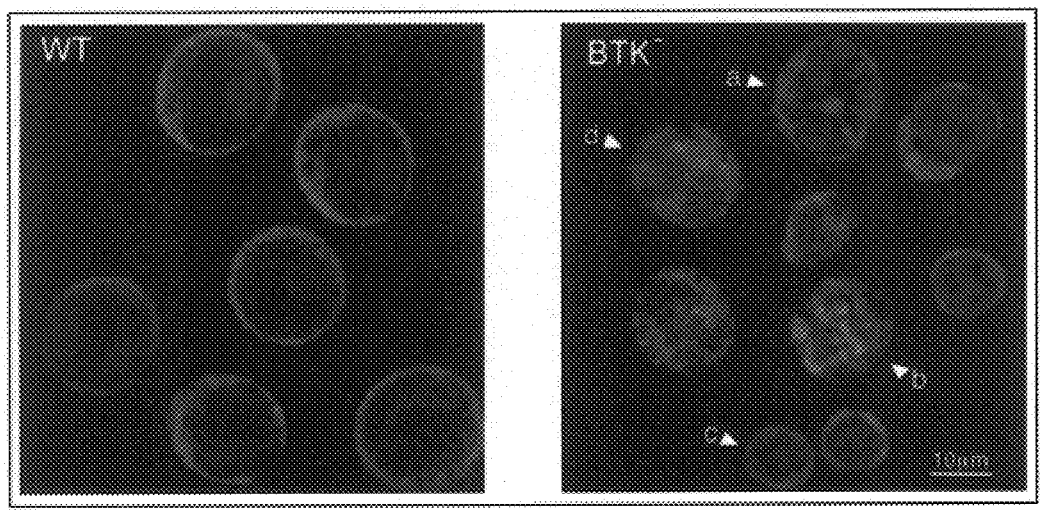
FIGS. 3A–3D: BTK inhibits Fas-mediated apoptosis.
Figure 3B:
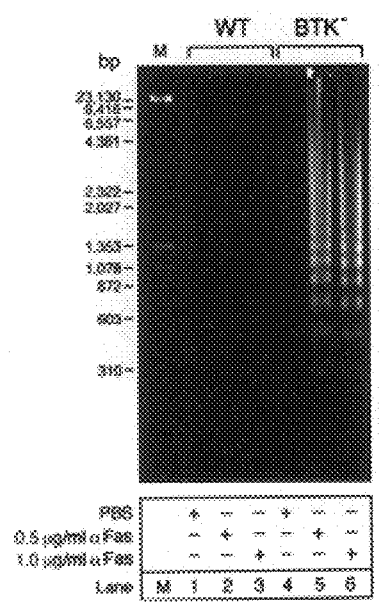

The comparative examination of the morphologic features of wild-type versus BTK-deficient DT-40 cells by laser scanning confocal microscopy showed no evidence of apoptosis for wild-type cells after treatment with the agonistic anti-Fas antibody, whereas BTK-deficient cells showed shrinkage and nuclear fragmentation consistent with apoptosis (FIG. 3A). On agarose gels, DNA from Triton-X-100 lysates of anti-Fas treated BTK-deficient DT-40 cells showed a ladder-like fragmentation pattern consistent with apoptosis, whereas no DNA fragmentation was observed in wild-type DT-40 cells (FIG. 3B). These results provide direct evidence that BTK can inhibit Fas/APO-1-mediated apoptosis.

Figure 3C:
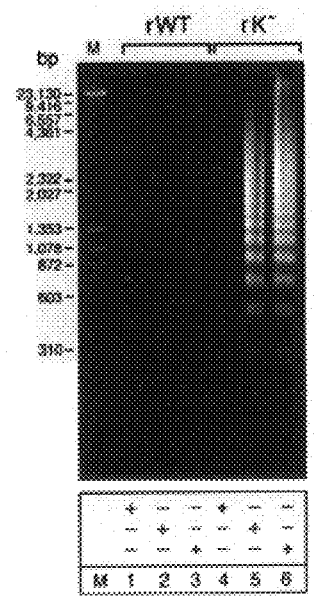
Figure 3D:
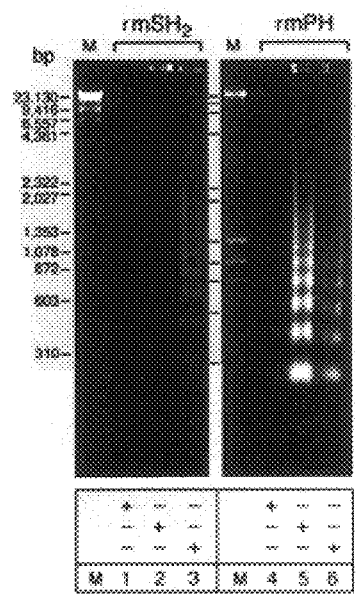

BTK has a unique N-terminal region which contains a pleckstrin homology (PH) and Tec homology (TH) domains, a single Src homology 3 (SH3) domain which contains the autophosphorylation site at tyrosine 223, a single SH2 domain, and a catalytic kinase domain which contains the transphosphorylation site at tyrosine 551 (Rawlings, D. J., Witte, O. N. (1994) *Immunol. Rev.* 138, 105–119; and Kurosaki, T. (1997) *Curr Opin. Immunol.* 9, 309–318). The PH domain of BTK interacts with various isoforms of protein kinase C, heterotrimeric G proteins, as well as the BAP-135 protein (Rawlings, D. J., Witte, O. N. (1994) *Immunol. Rev.* 138, 105–119; Kurosaki, T. (1997) *Curr Opin. Immunol.* 9, 309–318; Tsukada, S. (1994)*J. Biol. Chem.* 269, 10217–10220; and Yang, W., Desiderio, S. (1997) *Proc Natl Acad Sci USA* 94, 604–609). SH3 domains have been shown to interact with proline-rich sequences of other proteins whereas SH2 domains interact with tyrosine phosphorylated proteins (Yang, W., Desiderio, S. (1997) *Proc Natl Acad Sci USA* 94, 604–609). However, specific proteins interacting with the BTK SH2 or SH3 domains in B-lineage lymphoid cells have not been reported. Mutations in the catalytic domain, SH2 domain, as well as PH domain of the BTK have been found to lead to maturational blocks at early stages of B-cell ontogeny in human XLA (Pawson, T., Gish, G. D. (1992) *Cell* 71, 359–362; and Vihinen, M., et al. (1995) *Immunol. Today* 16, 460–465). BTK-deficient mice generated by introducing PH-domain or catalytic domain mutations in embryonic stem cells showed defective B-cell development and function (Kerner, J. D., et al. (1995) *Immunity* 3, 301–312. Thus, different regions of BTK are important for its physiologic functions. To examine the participation of the various domains of BTK in negative regulation of Fas-mediated apoptosis, we introduced wild-type human btk gene as well as human btk genes harboring mutations either in the catalytic domain ($Arg^{525}$ to Gln), SH2 domain ($Arg^{307}$ to Ala), or PH domain ($Arg^{28}$ to Cys) into the BTK-deficient DT-40 cells (Uckun, F. M., et al. (1996) *Science* 273, 1096–1100). As evidenced in FIG. 3C & 3D, BTK-deficient DT-40 cells reconstituted with wild-type human btk gene (rWT) did not undergo apoptosis after treatment with the agonistic anti-Fas antibody, whereas Fas-activation of reconstituted BTK-deficient DT-40 cells expressing human BTK with mutations in the kinase (rK-), SH2 (rmSH2), or PH (rmPH) domains induced apoptosis as it did in non-reconstituted BTK-deficient DT-40 cells shown in FIG. 3B. Thus, the kinase, SH2, and PH domains of BTK are all important and apparently indispensable for its function as a negative regulator of Fas-mediated apoptosis.

Figure 4B:
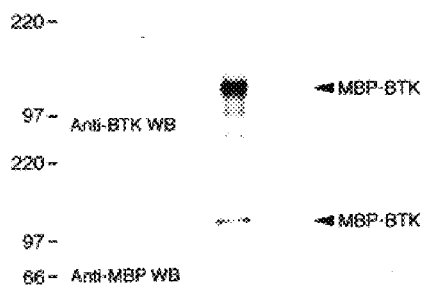
Figure 4C:
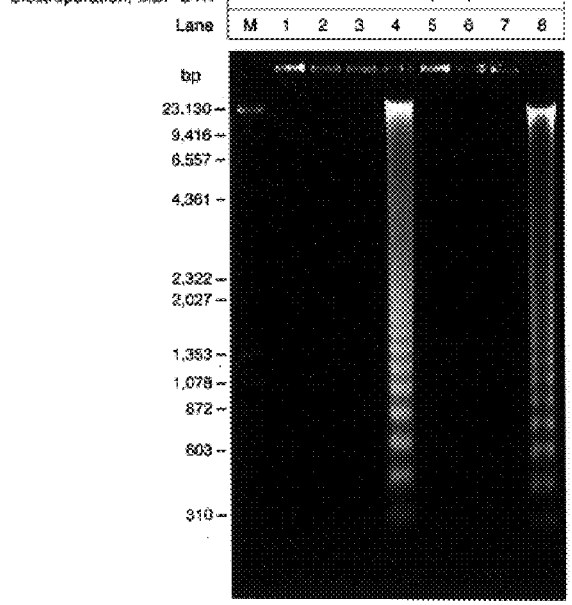

To further characterize the anti-apoptotic function of BTK, we introduced by electroporation an MBP fusion protein containing full-length wild-type BTK into BTK-deficient cells 4 hours prior to treatment with the anti-Fas antibody. Examination of these cells by confocal laser scanning microscopy (FIG. 4A) as well as Western blot analysis using anti-BTK and anti-MBP antibodies (FIG. 4B) confirmed the presence of the electroporated MBP-BTK protein. As shown in FIG. 4C, introduction of wild-type BTK protein by electroporation rendered the BTK-deficient DT-40 cells resistant to the apoptotic effects of Fas-ligation, suggesting direct protein-protein interactions between BTK and members of the Fas signal transduction pathway as a possible mechanism for the anti-apoptotic function of BTK.

The downstream pro-apoptotic events initiated by the ligation of Fas or TNF receptor-1 are beginning to be illuminated (Fraser, A., Evan, G. (1996) Cell 85, 781–784; Kischkel, F. C., et al. (1995) EMBO J. 14, 5579–5588; Hu, S., Vincenz, et al. (1997) J. Biol. Chem. 272, 17255–17257; Deveraux, Q. L., et al. (1997)Nature 388, 300–304; Thome, M., et al. (1997)Nature 386, 517–521; Boldin, M. P., et al. (1995) J. Biol. Chem. 270, 7795–7798; Los, M., et al. (1995) Nature 375, 81–83; Boldin, M. P., et al. (1996) Cell 85, 803–815; and Chinnaiyan, A. M., et al. (1995)Cell 81, 505–512). Both Fas and TNF receptor-1 contain a homologous intracellular "death domain", which plays a pivotal role in ligand-dependent assembly of a pro-apoptotic death inducing signaling complex (DISC) (Kischkel, F. C., et al. (1995) EMBO J. 14, 5579–5588). The death domains of p55 TNF receptor-1 and Fas/CD95 serve as docking sites that mediate ligand-dependent recruitment of and heteroassociation with other death domain containing multivalent adapter proteins: Fas associated protein with death domain (FADD) and receptor-interacting protein (RIP) in the case of CD95; and TNF receptor-1-associated death domain protein (TRADD) and RIP in the case of TNF receptor-1 (Fraser, A., Evan, G. (1996) Cell 85, 781–784; Kischkel, F. C., et al. (1995) EMBO J. 14, 5579–5588; and Chinnaiyan, A. M., et al. (1995)Cell 81, 505–512). FADD is the point of convergence between the Fas/CD95- and TNF receptor-1-linked apoptotic signal transduction pathways. Whereas Fas/CD95 directly recruits FADD, TNF receptor 1 binds TRADD, which then acts as an adapter protein to recruit FADD. The formation of CD95-FADD or TNF receptor-1-TRADD-FADD complexes following ligand binding are important for the induction of apoptosis. The assembly of a pro-apoptotic DISC is completed by the recruitment and concomitant activation of the cytosolic caspase FLICE, a member of the ICE protease family (Fraser, A., Evan, G. (1996) Cell 85, 781–784; Kischkel, F. C., et al. (1995) EMBO J. 14, 5579–5588; Hu, S., Vincenz, et al.(1997) J. Biol. Chem. 272, 17255–17257; Deveraux, Q. L., et al. (1997)Nature 388, 300–304; Thome, M., et al. (1997) Nature386, 517–521; Boldin, M. P., et al. (1995) J. Biol. Chem. 270, 7795–7798; Los, M., et al. (1995) Nature 375, 81–83; Boldin, M. P., et al. (1996) Cell 85, 803–815; and Chinnaiyan, A. M., et al. (1995)Cell 81, 505–512). Recently, a number of proteins have been identified as inhibitors of Fas- as well as TNF receptor-1 induced apoptosis ((Fraser, A., Evan, G. (1996) Cell 85, 781–784; Kischkel, F. C., et al. (1995) EMBO J. 14, 5579–5588; Hu, S., Vincenz, et al. (1997) J. Biol. Chem. 272, 17255–17257; Deveraux, Q. L., et al. (1997) Nature 388, 300–304; Thome, M., et al. (1997) Nature 386, 517–521). These proteins interact directly with FADD or FLICE, thereby interfering with DISC assembly and function. Notably, the death domain of Fas contains a conserved YXXL motif similar to the immunoreceptor tyrosine-based activation motif (ITAM) sequences as a potential binding site for SH2 containing proteins and Fas has recently been shown to associate with Fyn and Lck kinases as pro-apoptotic regulators which are required for induction of Fas-mediated apoptosis (Schlottmann, K. E., et al. Leukocyte Biology 60, 546–554; and Atkinson, E. A., et al. (1996) J. Biol. Chem. 271, 5968–5971). We therefore postulated that BTK could interact with Fas and prevent the assembly of a proapoptotic DISC after Fas-ligation.

Figure 5A:
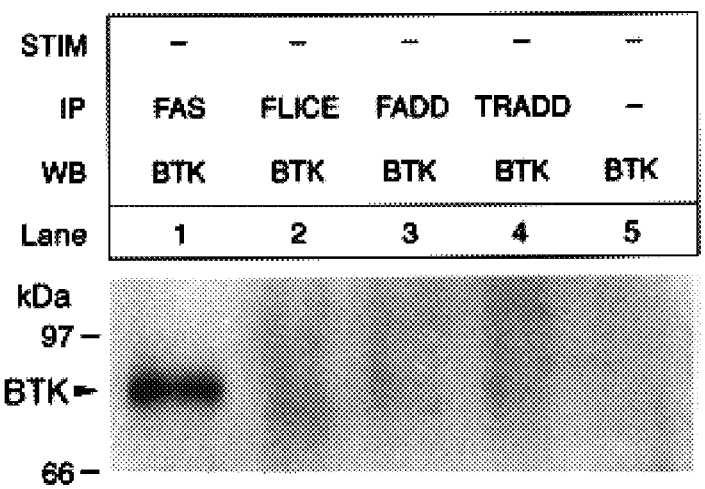
FIGS. 5A–5D: BTK associates with FAS and Intereferes with FAS-FADD Interactions. The Fas, FLICE, FADD, and TRADD immune complexes immunoprecipitated from Nonidet P-40 lysates of untreated wild-type DT-40 lymphoma B-cells were collected, washed, boiled in 2×SDS sample buffer, fractionated on 12.5% polyacrylamide gels, transferred to an Ihmobilon-PVDF membrane, and examined for the presence of BTK protein by imrnunoblotting, as described in the Examples and shown in FIG. 5A. The BTK and FADD immune complexes (as well as the positive control FAS immune complexes) immnunoprecipitated from untreated versus Fas-activated BTK-deficient DT-40 lymphoma B-cells, which were reconstituted with wild-type human btk gene, were collected, washed, boiled in 2×SDS sample buffer, fractionated on 12.5% polyacrylamide gels, transferred to an Immobilon-PVDF membrane, and immunoblotted with a monoclonal anti-Fas antibody, as described below and shown in FIG. 5B. FAS, FLICE, FADD, TRADD, and BTK immune complexes from lysates of BTK-positive NALM-6-UM1 human B-cell precursor leukemia cells were subjected to anti-Fas Western blot analysis as shown in FIG. 5C. FADD was immunoprecipitated from Nonidet-P-40 lysates of untreated versus Fas-activated (anti-Fas 1 μg/ml×1 hour) BTK-deficient DT-40 cells, as described in the Examples. The immune complexes were collected, washed, boiled in 2×SDS sample buffer, fractionated on 12.5% polyacrylamide gels, transferred to an Imrobilon-PVDF membrane, and immunoblotted with a monoclonal anti-Fas antibody (FIG. 5D). Similarly, the FAS immune complexes from the same cells were examined for the presence of FADD by immunoblotting.
Figure 5B:
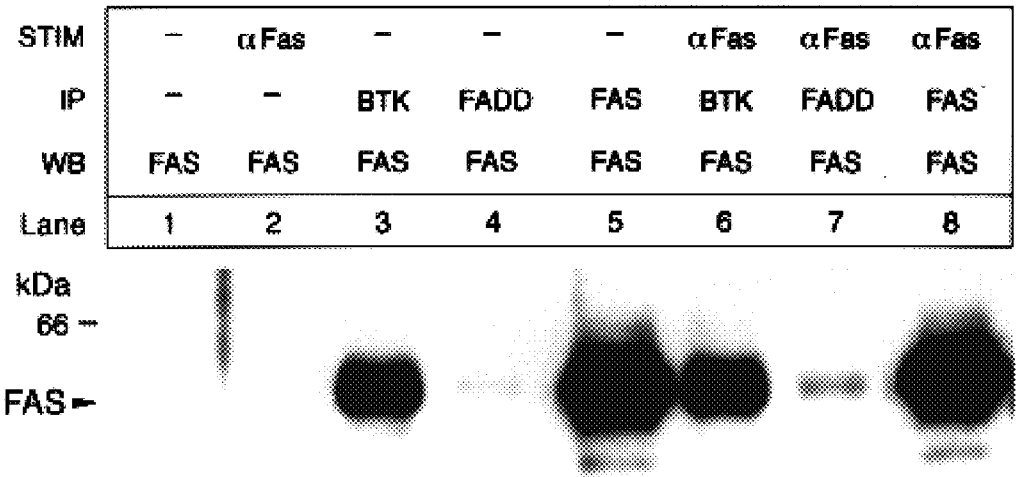
Figure 5C:
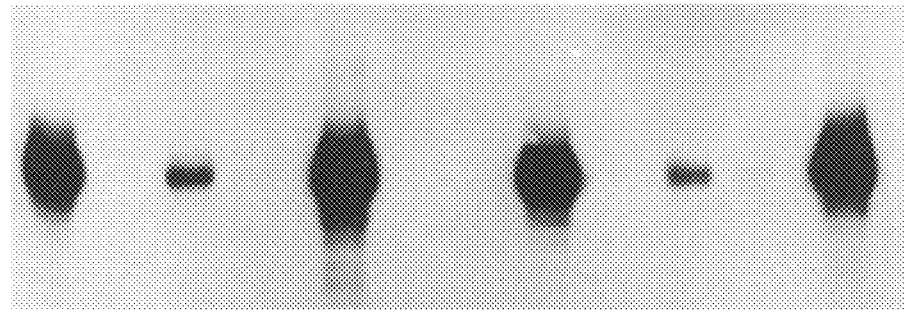
Figure 5D:

We first investigated if BTK is capable of a physical association with Fas and other members of DISC by examining the Fas, FLICE, FADD, and TRADD immune complexes from the Nonidet P-40 lysates of untreated DT-40 cells for the presence of BTK. BTK was detected by Western blot analysis in Fas (but not the other) immune complexes by anti-BTK immunoblotting (FIG. 5A). Similarly, Fas was detected by anti-Fas immunoblotting in BTK immune complexes from wild-type DT-40 cells as well as BTK-deficient DT-40 cells reconstituted with wild-type human btk gene (FIG. 5B). The constitutive association of BTK with Fas protein was also found in the human B-cell precursor leukemia cell line NALM-6-UM1 (FIG. 5C). Taken together, these results demonstrated that BTK is capable of associating with Fas protein and this physical association does not require prior engagement of the Fas receptor. As shown in FIG. 5D, Fas is associated with FADD in BTK-deficient DT-40 cells, as evidenced by detection of Fas in FADD immune complexes and this physical interaction was markedly enhanced after Fas-ligation. In Fas-activated BTK-deficient DT-40 cells, Fas-associated FADD molecules could be detected by anti-FADD inununoblotting (FIG. 5D). In contrast to BTK-deficient DT-40 cells, very little Fas-FADD association was found in untreated or anti-Fas treated BTK-deficient DT-40 cells reconstituted with wild-type human BTK (FIG. 5B). Similarly, Fas-ligation failed to enhance the Fas-FADD association in human NALM-6-UM1 leukemia cells (FIG. 5C). Thus, BTK associates with Fas and impairs its interaction with FADD, a protein which is essential for the recruitment and activation of FLICE by Fas during the apoptotic signal. While these results do not exclude the possibility that BTK may alter the fate of the apoptotic signal triggered by Fas ligation by multiple mechanisms including modulation of the function of positive or negative regulators of apoptotic signal transduction, they do provide at least one plausible explanation for the observed anti-apoptotic function of BTK.

Figure 6A:
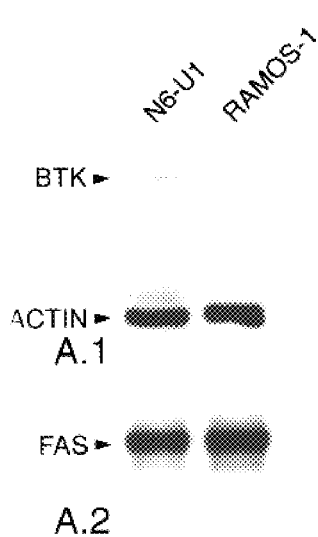
FIGS. 6A–6D: Apoptotic Responses of Human B-lineage Leukemia Cells to Fas Ligation in Relationship to BTK Expression and Function. Anti-BTK and anti-Actin dual-antibody Western blot analysis of whole cell lysates from BTK-positive NALM-6-UM1 (N6-U1) and BTK-deficient RAMOS-1 cells (FIG. 5A). Anti-Fas Western blot analysis of the same cell lysates. [B] Cells were harvested 24 hours after exposure to anti-Fas antibody at 0.1 μg/ml or 1.0 μg/ml concentrations and DNA from Triton-X-100 lysates was analyzed for fragmentation, as described by Uckun, F. M., et al. (1996) *Science* 273, 1096–1100; and Uckun, F. M., et al. (1995) *Science* 267, 886–91. Anti-Fas treatment induced apoptosis in BTK-deficient RAMOS-1 cells but not in BTK-positive N6-U1 cells. [C.1] and [C.2] Anti-BTK and anti-Fas Western blot analysis of whole cell lysates from N6-U1 cells treated with the BTK inhibitor LMA-13 (10 μM×4 hours). [C.3] Anti-Fas and Anti-BTK Western blot analysis of anti-BTK antibody immunoprecipitated BTK immune complexes from untreated (=−Inhibitor) and LMA-13-treated (10 μM×4 hours) (=+Inhibitor) N6-U1 cells. [D]. N6-U1 cells were harvested 24 hours after exposure to anti-Fas antibody at 0.1 μg/ml or 1.0 μg/ml concentrations and DNA from Triton-X-100 lysates was analyzed for fragmentation, as described by Uckun, F. M., et al. (1996) *Science* 273, 1096–1100; and Uckun, F. M., et al. (1995) *Science* 267, 886–91. Anti-Fas treatment induced apoptosis in LMA-13-pretreated (10 μM×4 hours) (=Inhibitor +) N6-U1 cells. In contrast, no apoptosis was observed in N6-U1 cells that were not pretreated with this BTK inhibitor (=Inhibitor −). An ECL detection system (Amersham Pharmacia Biotech, Arlington Heights, Ill., cat no. RPN2106) was used for the Western blot analyses in [A.1], [A.2], [C.1], [C.2], and [C.3].
Figure 6B:
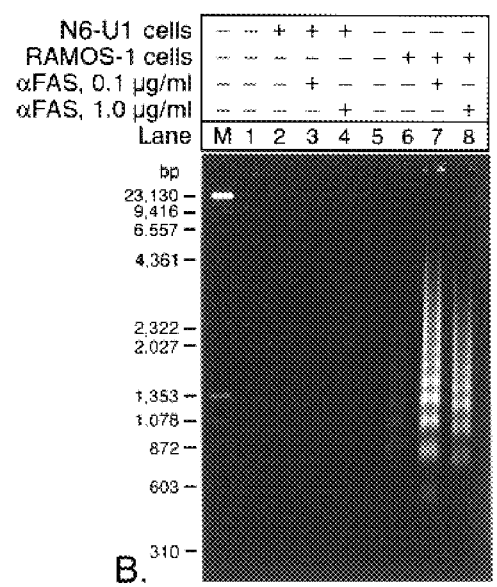
Figure 6C:
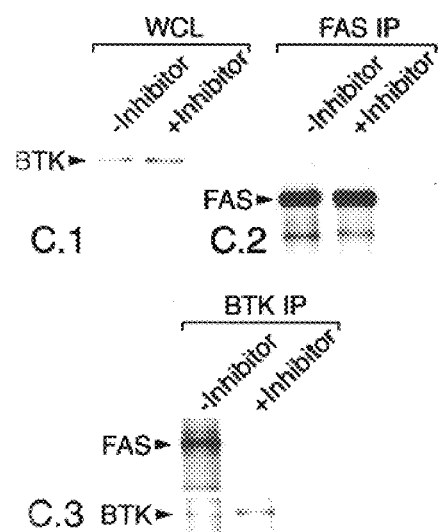
Figure 6D:
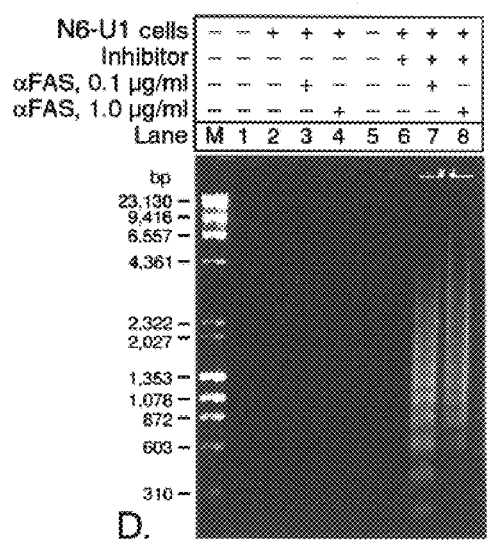

To further elucidate the physiologic significance of the observed BTK-Fas association in human leukemic B-cell precursors, we compared the sensitivities of BTK-positive NALM-6-UM1 human pre-B leukemia cell line and BTK-deficient RAMOS-1 human B-cell leukemia cell line to Fas-mediated apoptosis. As shown in FIG. 6A, these two cell lines express similar levels of Fas protein. BTK-deficient RAMOS-1 cells underwent apoptosis after Fas ligation with the agonistic anti-Fas antibody but BTK-positive NALM-6-UM1 cells did not (FIG. 6B). We next examined the effects of the leflunomide metabolite analog α-cyano-β-hydroxy-β-methyl-N-(2,5-dibromophenyl)propenamide (LMA-13), a potent inhibitor of BTK on BTK-Fas association and resistance to Fas-mediated apoptosis in NALM-6-UM1 cells. Anti-BTK and anti-Fas Western blot analyses of whole cell lysates from LMA-13-treated NALM-6-UM1 cells showed no reduction in BTK (FIG. 6.C.1) or Fas protein (FIG. 6.C.2) expression levels. There was substantially less Fas protein in the BTK immune complexes, providing direct evidence that inhibition of TK by LMA-13 abrogates the BTK-Fas association (FIG. 6C.3). Notably, a 4 hour treatment with LMA-13 did not induce apoptosis in NALM-6-UM1 cells but rendered these highly resistant human leukemia cells sensitive to Fas-mediated apoptosis (FIG. 6D). These results provided further show that BTK is a physiologically important negative regulator of Fas-mediated apoptosis.

Figure 7A:
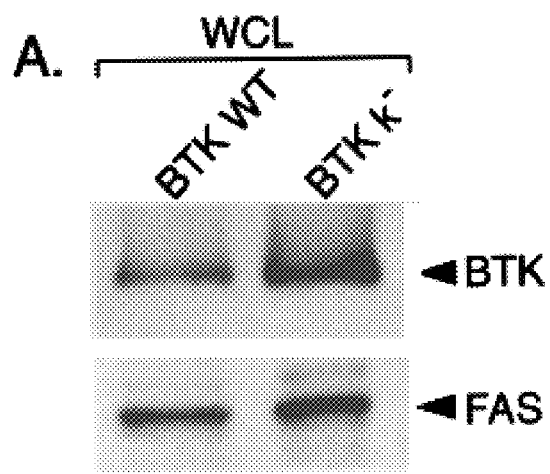
FIGS. 7A–7B: Kinase-Inactive BTK Does Not Associate with Fas. Anti-BTK (A.1) and anti-Fas (A.2) Western blot analysis of whole cell lysates from BTK-deficient DT-40 cells (FIG. 7A) reconstituted with wild-type human BTK (BTK-, rBTK[WT]) (Lane 1) or kinase domain mutant inactive human BTK (BTK-, rBTK[K-] (Lane 2). The expression levels of BTK and Fas were measured by immunoblotting using appropriate antibodies and the ECL chemiluminescence detection system.
Figure 7B:
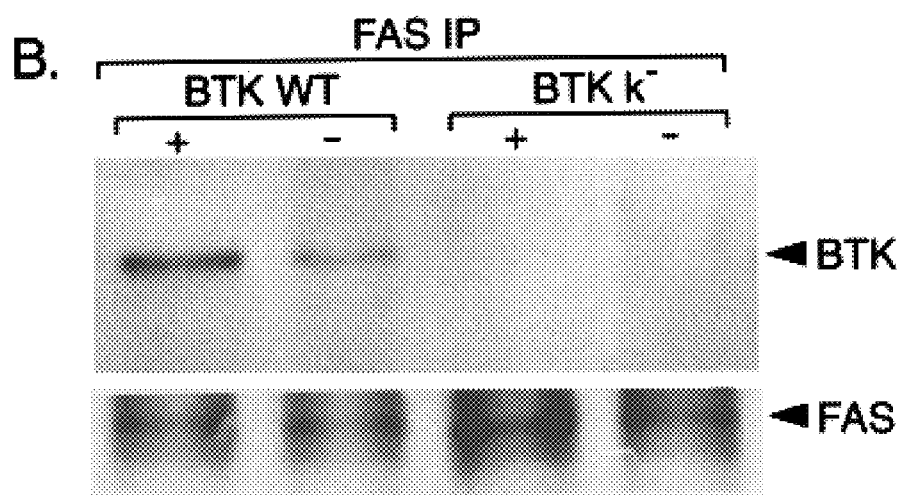

The ability of the BTK inhibitor LFM-A13 to abrogate the BTK-Fas association provided evidence that the kinase activity of BTK plays an important role for the formation of the BTK-Fas complexes. In order to further establish whether or not the association of BTK with Fas is dependent on its kinase activity, we next examined BTK-Fas interactions in BTK-deficient DT-40 cells reconstituted with either wild-type human BTK (BTK-, rBTK[WT]) or kinase inactive mutant ($Arg^{525}$ to Gln) human BTK (BTK-, rBTK[K-]). As shown in FIG. 7A, Western blot analysis of whole cell lysates from these two cell lines with anti-BTK or anti-Fas antibodies did not reveal any substantial differences (i.e., in both of two independent experiments, we observed slightly higher BTK and Fas expression levels in BTK-, rBTK[K-] cells). Fas immune complexes from lysates of BTK-, rBTK [WT] cells contained BTK protein and this BTK-Fas association was further enhanced by treatment of cells with the anti-Fas antibody (FIG. 7B, lanes 1 and 2). In contrast, no BTK protein was detectable in Fas immune complexes from BTK-, rBTK[K-] cells regardless of treatment with the anti-Fas antibody (FIG. 7B, lanes 3 and 4). These results provide corroborating evidence that the association of BTK with Fas is dependent on the kinase activity of BTK.

Figure 8A:
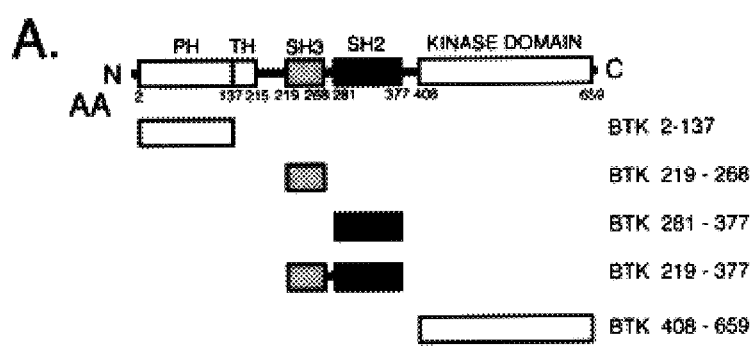
FIGS. 8A–8F: Binding of BTK fusion proteins to Fas protein in chicken and human B-lineage lymphoid cells.
Figure 8B:
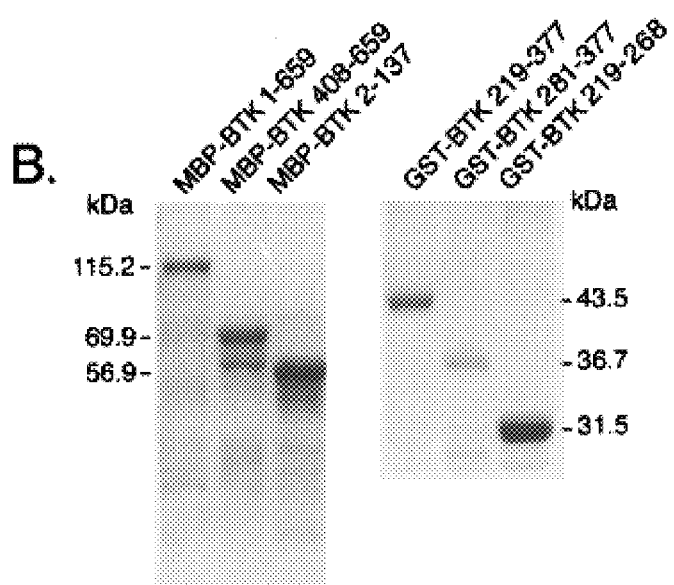
Figure 8C:
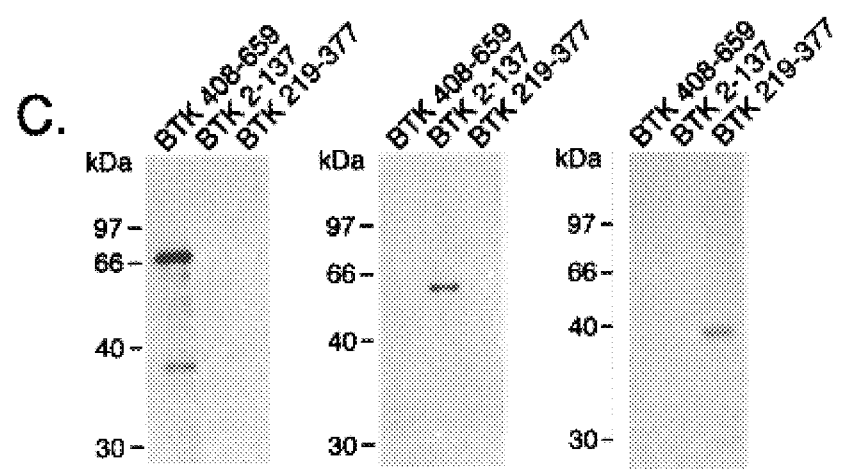
Figure 8D:
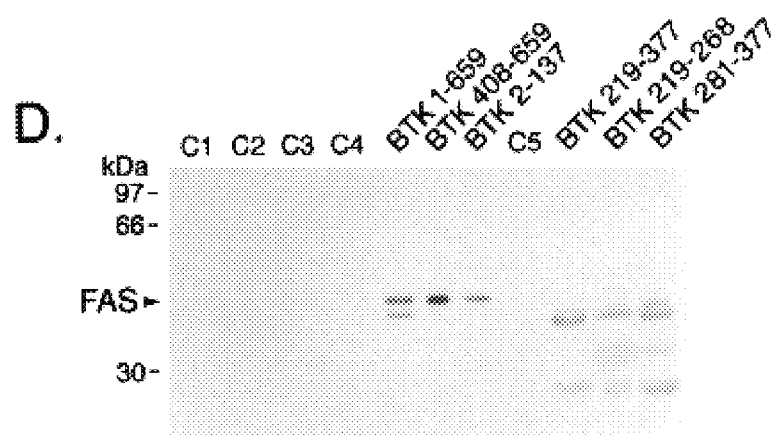
Figure 8E:
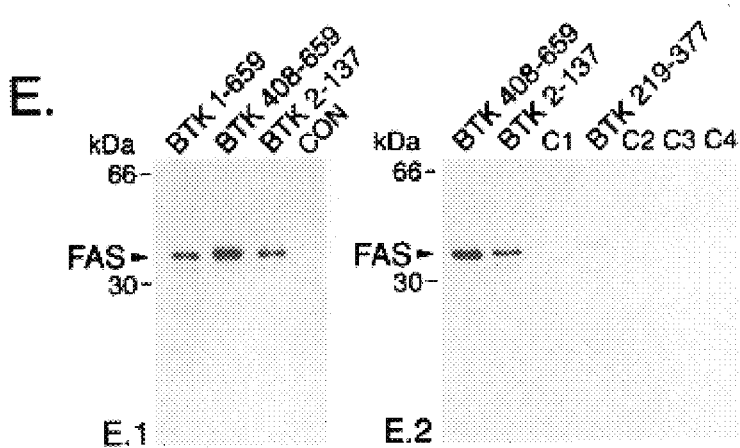
Figure 8F:
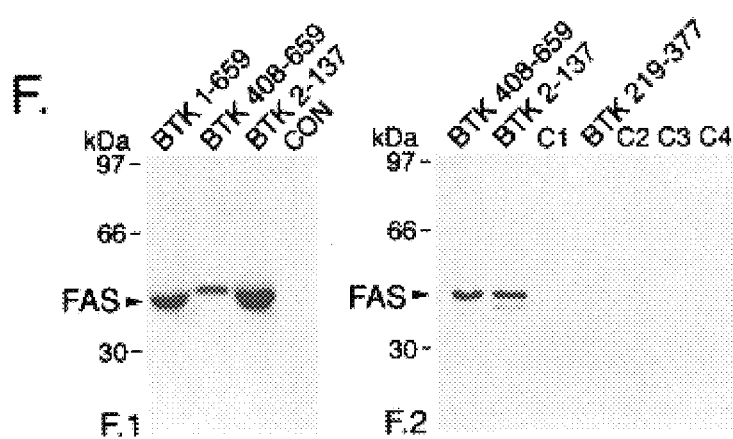

We next performed binding experiments with full length MBP-BTK and truncated MBP-BTK and GST-BTK fusion proteins corresponding to various domains of BTK (FIG. 8A–C) to elucidate the structural requirements for BTK association with Fas. MBP-BTK 1–659 (full length BTK) as well as MBP-BTK 408–659 ("BTK kinase domain") and MBP-BTK 2–137 ("BTK PH domain") were able to bind and pull down Fas from lysates of BTK-deficient DT-40 cells (FIG. 8D), human NALM-6 pre-B leukemia cells (FIG. 8E), and KL2 human EBV-transformed B-lymphoblastoid cells (FIG. 8F). However, Fas did not bind to the control MBP-BTK 519–567 fusion protein corresponding to a truncated kinase domain containing the Y551 transphosphorylation site (C5 in FIG. 7D), GST-BTK 219–377 containing the SH3 plus SH2 domains, GST-BTK 219–268 corresponding to the SH3 domain, or GST-BTK 281–377 corresponding to SH2 domain (the latter two were used only with lysates from BTK-deficient DT-40 cells) (FIG. 8D–F).

Although the crystal structure of full length BTK has not been reported, the recently published structures of the PH domain and BTK motif (Hyvonen, M., Saraste, M. (1997) *EMBO J*. 16, 3396–3404) provide useful information applicable to the binding capability of BTK and its PH domain. FADD has been reported to interact with the cytoplasmic domain of Fas, which is largely composed of a death domain consisting of six antiparallel a-helices assembled from residues 230–314 (Huang, B., et al. (1996)*Nature* 384, 638–641). The YXXL sequence of the Fas death domain has been speculated to resemble ITAMs and be recognized by an SH2 domain of a PTK upon tyrosine phosphorylation or by other mechanisms (Schlottmann, K. E., et al. *Leukocyte Biology* 60, 546–554; and Atkinson, E. A., et al. (1996) *J. Biol. Chem*. 271, 5968–5971). An analysis of the conformation of this YXXL sequence shows that it is located in the middle of an α-helix and unless a substantial conformational change of that α-helix would occur to make the tyrosine residue more accessible, it may be too rigid for interaction with a PTK. Thus, the structural geometry of the YXXL sequence would likely prevent Fas and BTK to adopt a binding mode such as that of is CD3-ε ITAM/ZAP-70 as was suggested by Atkinson, E. A., et al. (1996) *J. Biol. Chem*. 271, 5968–5971. The inability of the BTK SH2 domain to pull down Fas from whole cell lysates further supports this notion. How then does BTK associate with Fas? BTK and Fas may associate via complementary electrostatic attractions and hydrogen bond interactions which could involve the previously reported charged residues on the surfaces of the α-helices of the Fas death domain. This association could be mediated by a third protein which forms an interface between Fas and BTK. The importance of the SH2 and kinase domains of BTK for its anti-apoptotic function prompts the hypothesis that a tyrosine phosphorylated substrate of BTK may provide such an interface.

The ability of BTK to inhibit the pro-apoptotic effects of Fas-ligation prompts the hypothesis that apoptosis of developing B-cell precursors during normal human B-cell ontogeny may be reciprocally regulated by Fas and BTK. The absence of BTK or mutations in its kinase, PH, and SH2 domains could lead to inappropriate apoptotic cell death of pre-B cells leading to the phenotype of XLA (Rawlings, D. J., Witte, O. N. (1994) *Immunol. Rev*. 138, 105–119; Tsukada, S., et al. (1993) *Cell* 72, 279–290; and Vetrie, D. (1993) *Nature* 361. 226–233). Inappropriate apoptosis may underlie the pathogenesis as well as drug resistance of human leukemias and lymphomas, which makes control of apoptosis an important potential target for therapeutic intervention. The fate of leukemia/lymphoma cells exposed to chemotherapeutic agents (e.g. vincristine, daunorubicin, or taxol) may reside in the balance between the opposing proapoptotic effects of caspases activated by DISC and an upstream negative regulatory mechanism involving BTK and/or its substrates. Therefore, inhibitors of BTK are likely to enhance the drug sensitivity of B-lineage leukemia/lymphoma cells.

Example 2

Synthesis of Specific Leflunomide Metabolite Analogs

Chemistry. All chemicals were purchased from Aldrich (Milwaukee, Wis.) and were used without further purification. Except where moted, each reaction vessel was secured with a rubber septum, and the reaction was performed under nitrogen atmosphere. $^1H$ and $^{13}C$ NMR spectra were obtained on a Varian Mercury 300 instrument spectrometer (Palo Alto, Calif.) at ambient temperature in the solvent specified. Melting points were determined using a Fisher-Johns melting point apparatus and are uncorrected. FT-IR spectra were recorded on a Nicolet Protege 460 spectrometer (Madison, Wis.). GC/MS spectra were obtained on a HP 6890 GC System (Palo Alto, Calif.) equipped with a HP 5973 Mass Selective Detector.

MS (EI) spectra were obtained on an HP Series 1100 LL/MSD.

Figure 19:
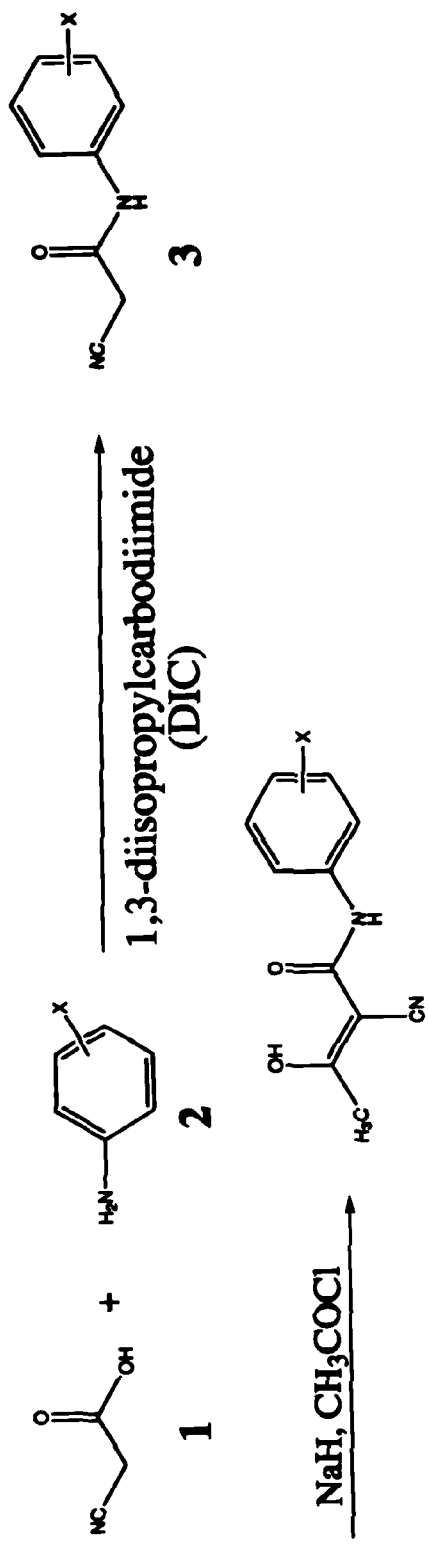
FIG. 19: Illustrates the synthesis of LFM-13 and other related compounds.

The general synthetic scheme for the preparations of LFM, and LFM-A 1–LFM-A14 (35,36) is illustrated in FIG. 19. Cyanoacetic acid 1 was coupled with the desired aniline 2 in the presence of diisopropylcarbodiimide (DIC) to form 3. Compound 3 was treated with NaH and then acylated with acetyl chloride to afford LFM or LFM-A1 to LFM-A14.
General Synthetic Procedure 1,3-diisopropylcarbodiimide (1.75 g; 13.9 mmol) was added to a solution of cyanoacetic acid 1 (1.70 g; 20.0 mmol) and the desired substituted-aniline 2 (12.6 mmol) in tetrahydrofuran (25 mL) at 0° C. The mixture was stirred for 12 hours at room temperature. The resulting urea precipitate (reaction side product) was removed by filtration and the filtrate was partitioned between ethyl acetate and 0.5 N HCl.

The organic layer was sequentially washed with brine twice, dried over anhydrous $Na_2SO_4$ and concentrated by rotary-evaporation. The crude solid product was recrystallized from ethyl alcohol to give pure 3. See Kuo, E. A., et al. (1996) *J. Med. Chem.* 39(23), 4608–21; and Sjogren, E. R., et al. (1991) *J. Med. Chem.* 34, 3295–3301.

Sodium hydride (0.93 g; 60% in mineral oil; 23.2 mmol) was added slowly to the solution of 3 (12.0 mmol) in tetrahydrofuran (40 mL) at 0° C. After stirring for 30 minutes at 0° C., acetyl chloride (1.04 g; 13.2 mmol) was added to the reaction mixture. The reaction was continued for another hour at room temperature and was quenched by the addition of acetic acid (2 mL). The mixture was poured into ice water (100 mL) containing 2.5 mL of hydrochloric acid to precipitate the crude product, which was collected by filtration and washed with water. The final pure product was obtained by recrystallization.

Physical Data

α-Cyano-β-hydroxy-β-methyl-N-[4-(trifluoromethyl)phenyl]-propenamide (LFM). mp: 230–233° C.; IR (KBr): 3303, 2218, 1600 and 1555 $cm^{-1}$; $^1$H NMR (DMSO-$d_6$): δ 11.01 (s, 1H, NH), 7.75 (d, J=8.4 Hz, 2H, ArH), 7.64 (d, J=8.4 Hz, 2H, ArH), 2.22 (s, 3H, $CH_3$); GC/MS m/z 270 ($M^+$), 161, 142, 111.

α-Cyano-β-hydroxy-β-methyl-N-(4-bromophenyl)propenamide (LFM-A1). mp: 213–214° C.; IR (KBr): 3288, 2228, 1615, 1555 $cm^{-1}$; $^1$H NMR (DMSO-$d_6$): δ 10.51 (s, 1H, NH), 7.49 (s, 4H, ArH), 2.25 (s, 3H, $CH_3$); MS (EI) m/z 280 ($M^+$).

α-Cyano-β-hydroxy-β-methyl-N-(4-chlorophenyl)propenamide (LFM-A2). mp: 209–211° C.; IR (KBr): 3298, 2223, 1598 and 1552 $cm^{-1}$; $^1$H NMR (DMSO-$d_6$): δ 10.48 (s, 1H, NH), 7.54 (d, J=8.7 Hz, 2H, ArH), 7.45 (s br, 1H, OH), 7.36 (d, J=8.7 Hz, 2H, ArH), 2.25 (s, 3H, $CH_3$); MS (CI) m/z 236 ($M^+$), 129, 127.

α-Cyano-β-hydroxy-β-methyl-N-(4-fluorophenyl)propenamide (LFM-A3). mp: 165–166° C.; IR (KBr): 3298, 2218, 1610 and 1560 $cm^{-1}$; $^1$H NMR (DMSO-$d_6$): δ 10.33 (s, 1H, NH), 7.80 (s br, 1H, OH), 7.53 (m, 2H, ArH), 7.16 (m, 2H, ArH), 2.26 (s, 3H, $CH_3$); GC/MS m/z 220 ($M^+$), 111.

α-Cyano-β-hydroxy-β-methyl-N-[2-(trifluoromethyl)phenyl]-propenamide (LFM-A4). mp: 61–63° C.; IR (KBr): 3435, 2209, 1619, 1952 and 1548 $cm^{-1}$; $^1$H NMR (DMSO-$d_6$): δ 10.99 (s, 1H, NH), 8.03 (d, J=7.5 Hz, 1H, ArH), 7.67 (d, J=7.5 Hz, 1H, ArH), 7.60 (dd, J=7.5, 7.5 Hz, 1H, ArH), 7.29 (dd, J=7.5, 7.5 Hz, 1H, ArH) 5.71 (s br, 1H, OH), 2.20 (s, 3H, $CH_3$); GC/MS m/z 270 ($M^+$), 161, 141, 114.

α-Cyano-β-hydroxy-β-methyl-N-(2-bromophenyl)propenamide (LFM-A5). mp: 98–100° C.; IR (KBr): 3351, 2214, 1609, 1585 and 1536 $cm^{-1}$; $^1$H NMR (DMSO-$d_6$): δ 10.76 (s, 1H, NM), 8.06 (dd, J=8.1, 1.5 Hz, 1H, ArH), 7.62 (dd, J=8.1. 1.5 Hz, 1H, ArH), 7.33 (m, 1H, ArH), 7.03 (m, 1H, ArH), 6.60 (s br, 1H, OH), 2.22 (s, 3H, $CH_3$); ); MS (EI) m/z 280 ($M^+$), 173, 171.

α-Cyano-β-hydroxy-β-methyl-N-(2-chlorophenyl)propenamide (LFM-A6). mp: 93–94° C.; IR (KBr): 3372, 2208, 1644, 1621 and 1587 $cm^{-1}$; $^1$H NMR (DMSO-$d_6$): δ 10.96 (s, 1H, NH), 8.16 (d, J=8.1 Hz, 1H, ArH), 7.46 (dd, J=7.5, 1.5 Hz, 1H, ArH), 7.29 (m, 1H, ArH), 7.08 (m, 1H, ArH), 2.22 (s, 3H, $CH_3$); MS (CI) m/z 236 ($M^+$), 129, 127.

α-Cyano-β-hydroxy-β-methyl-N-(2-fluorophenyl)propenamide (LFM-A7). mp: 118–119° C.; IR (KBr): 3409, 2212, 1613, 1591 and 1532 $cm^{-1}$; $^1$H NMR (DMSO-$d_6$): δ 1070 (s, 1H, NH), 7.91 (m, 1H, ArH), 7.23 (m, 2H, ArH), 7.13 (m, 2H ArH), 7.10 (s, br, 1H, OH), 2.22 (s, 3H, $CH_3$); GC/MS m/z 220 ($M^+$), 111.

α-Cyano-β-hydroxy-β-methyl-N-[3-(trifluoromethyl)phenyl]-propenamide (LFM-A8). mp: 182–184° C.; IR (KBr): 3303, 2221, 1619 and 1572 $cm^{-1}$; $^1$H NMR (DMSO-$d_6$): δ 10.79 (s, 1H, NH), 8.05 (s br, 1H, OH), 8.04 (s, 1H, ArH), 7.75 (d, J=8.1 Hz, 1H, ArH), 7.53 (dd, J=8.1, 7.5 Hz, 1H, ArH), 7.42 (d, J=7.5 Hz, 1H, ArH), 2.24 (s, 3H, $CH_3$); GC/MS m/z 270 ($M^+$), 161.

α-Cyano-β-hydroxy-β-methyl-N-(3-bromophenyl)propenamide (LFM-A9). mp: 184–185° C.; IR (KBr): 3303, 2228, 1610, 1595 and 1550 $cm^{-1}$; $^1$HMR (DMSO-$d_6$): δ 10.56 (s, 1H, NH), 7.89 (m, 1H, ArH), 7.47 (m, 1H, ArH), 7.28 (m, 2H, ArH), 6.37 (s br, 1H, OH), 2.26 (s, 3H, $CH_3$); MS (EI) m/z 282 ($M^++H$, $^{81}Br$), 280 ($M^++H$, $^{79}Br$), 173, 171.

α-Cyano-β-hydroxy-β-methyl-N-(3-chlorophenyl)propenamide (LFM-A10). mp: 184–187° C.; IR (KBr): 3293,2221, 1610, 1595 and 1557 $cm^{-1}$; $^-$H NMR (DMSO-$d_6$): δ 10.61 (s, 1H, NH), 7.76 (m, 1H, ArH), 7.42 (m, 1H, ArH), 7.33 (dd, J=8.1, 8.1 Hz, 1H, ArH), 7.16 (m, 1H, ArH), 6.84 (s br, 1H, OH), 2.25 (s, 3H, $CH_3$); MS (CI) m/z 239 ($M^++H$, $^{37}Cl$), 237 ($M^++H$ $^{35}Cl$), 129, 127.

α-Cyano-β-hydroxy-β-methyl-N-(3-fluorophenyl)propenamide (LFM-A11). mp: 136–138° C.; IR (KBr): 3297, 2221, 1613, 1597 and 1567 $cm^{-1}$; $^1$H NMR (DMSO-$d_6$): δ 10.54 (s, 1H, NH), 7.54 (m, 1H, ArH), 7.33 (m, 2H, ArH), 6.93 (m, 1H, ArH), 2.27 (s, 3H, $CH_3$); GC/MS m/z 220 ($M^+$), 111.

α-Cyano-β-hydroxy-β-methyl-N-[4-(trifluoromethoxy)phenyl]-propenamide (LFM-A12). mp: 182–183° C.; IR (KBr): 3308, 2213, 1625 and 1580 $cm^{-1}$; $^1$H NMR (DMSO-$_6$): δ 10.57 (s, 1H, NH), 7.90 (s br, 1H, OH), 7.64 (d, J=8.7 Hz, 2H, ArH), 7.32 (d, J=8.7 Hz, 2H, ArH), 2.25 (s, 3H, $CH_3$); GC/MS m/z 286 ($M^+$), 177, 108.

α-Cyano-β-hydroxy-β-methyl-N-(2,5-dibromophenyl)-propenamide (LFM-A13). mp: 148–150° C.; IR (KBr): 3353, 2211, 1648 and 1590 $cm^{-1}$; $^1$H NMR (DMSO-$d_6$): δ 11.41 (s, 1H, NH), 8.57 (d, J=2.4 Hz, 1H, ArH), 7.55 (d, J=8.7 Hz, ArH), 7.14 (dd, J=8.7, 2.4 Hz, 1H, ArH), 7.10 (s br, 1H, OH), 2.17 (s, 3H, $CH_3$); MS (EI) m/z 362 ($M^++4$), 360 ($M^++2$), 358 ($M^+$), 253, 251, 249, 150.

α-Cyano-β-hydroxy-β-methyl-N-(phenyl)propenamide (LFM-A14). mp: 134–135° C.; IR (KBr): 3281, 2214, 1605, 1579 and 1554 $cm^{-1}$; $^1$H NMR (DMSO-$d_6$): δ 10.33 (s, 1H, NH), 7.51 (d, J=7.5 Hz, 2H, ArH), 7.40 (s, br, 1H, OH), 7.31 (dd, J=7.5, 7.5 Hz, 2H, ArH), 7.11 (m, 1H, ArH), 2.26 (s, 3H, $CH_3$); GM/MS m/z 202 ($M^+$), 93.

Using procedures similar to the general procedure identified above, the following compounds of formula I were also prepared.

α-Cyano-β-hydroxy-β-methyl-N-[4-(methylsulfonyl)phenyl]-propenamide; prepared by oxidation of the corresponding 4-methylthio compound with peracetic acid in acetic acid; mp: 205–206° C.; $^1$H NMR (DMSO-$d_6$): δ 11.26 (s, 1), 7.81 (d, 2), 7.76 (d, 2), 3.15 (s, 3), 2.19 (s, 3); IR (KBr): 3309, 2225, 1643 and 1586 $cm^{-1}$; MS (EI) m/z 281.0 ($M+H^+$), 172.1.

α-Cyano-β-hydroxy-β-methyl-N-[3-methylsulfonyl)phenyl]-propenamide; prepared by oxidation of the corresponding 3-methylthio compound with peracetic acid in acetic acid; mp: 213–214° C.; $^1$H NMR (DMSO-d$_6$): δ 10.98 (s, 1), 8.18 (m, 1), 7.82 (m, 1), 7.60 (m, 2), 3.18 (s, 3), 2.23 (s, 3); IR (KBr): 3278, 2231, 1607 and 1555 cm$^{-1}$; MS (EI) m/z 281.0 (M+H$^{30}$), 172.1.

α-Cyano-β-hydroxy-β-methyl-N-[3-bromo-4-(trifluoromethoxy)-phenyl]propenamide; mp: 178–179° C.; $^1$H NMR (DMSO-d$_6$): δ 11.03 (s, 1), 8.12 (d, 1), 7.55 (dd, 1), 7.45 (m, 1), 5.53 (s, 1), 2.20 (s, 3); IR (KBr); 3304, 2350, 1620 and 1602 cm$^{-1}$; MS (EI) m/z 365.0 (M +H$^+$), 255.9.

α-Cyano-β-hydroxy-β-methyl-N-(2,4-dibromophenyl)-propenamide; mp: 181–181° C; $^1$HMR (DMSO-d$_6$): δ 11.03 (s, 1), 8.14(m, 1),7.84(d, 1), 7.51 (dd, 1), 5.65 (s, 1), 2.20 (s, 3); IR (KBr): 3360, 2205, 1591 and 1530 cm$^{-1}$; MS (EI) m/z 361.0 (M+H$^+$), 249.9.

α-Cyano-β-hydroxy-β-methyl-N-(2,4-dichlorophenyl)-propenamide; mp: 143–144° C; $^1$H NMR (DMSO-d$_6$): δ 11.23 (s, 1), 8.29 (m, 1), 7.60 (d, 1), 7.35 (dd, 1), 5.17 (s, 1), 2.18 (s, 3); IR (KBr): 3371, 2210, 1601 and 1540 cm$^{31\ 1}$; MS (EI) m/z 271.0 (M+H$^{30}$), 162.0.

α-Cyano-β-hydroxy-β-methyl-N-(2,5-dichlorophenyl)-propenamide; mp: 143–144° C.; $^1$H NMR (DMSO-d$_6$): δ 11.70 (s, 1), 8.51 (d, 1), 7.45 (d, 1), 7.05 (dd, 1), 4.97 (s, 1), 2.14 (s, 3); IR (KBr): 3370, 2215, 1581 and 1528 cm $^{31}$; MS (EI) m/z 271.0 (M+H$^+$), 162.0.

α-Cyano-β-hydroxy-β-methyl-N-(3,4-didichlorophenyl)-propenamide; mp: 216–217° C.; $^1$H NMR (DMSO-d$_6$): δ 10.74 (s, 1), 7.95 (m, 1), 7.54 (m, 1), 7.47 (m, 1), 5,64 (s, 1), 2.23 (s, 3); IR (KBr): 3319, 2225 and 1612 cm$^{31}$$_1$; m/z 271.0 (M+H$^+$), 162.0.

Using a BTK inhibition assay similar to the one described in described in Table 1, the above compounds were found to act as BTK inhibitors, generally having IC$_{50}$s of 20 μm/mL or less. The compounds were also found to sensitize cells to apoptosis with vincristine and ceramide using a procedure similar to that described in Example 3.

Example 3

The following example provides information of how specific inhibitors of BTK can be designed. A homology model for the kinase domain of BTK is disclosed, which is useful for the design and confirmation of inhibitors of BTK. The use of the homology model to identify specific compounds, including a novel leflunomide metabolite analog that is a potent and selective inhibitor of BTK is also disclosed.

In an effort to design potent inhibitors of the anti-apoptotic tyrosine kinase BTK as antileukemic agents with apoptosis promoting and chemosensitizing properties, a three-dimensional homology model of the BTK kinase domain was constructed, as described more completely below. Modeling studies revealed a distinct rectangular binding pocket near the hinge region of the BTK kinase domain with Leu$^{460}$, Tyr$^{476}$, Arg$^{525}$ and Asp$^{539}$ residues occupying the corners of the rectangle. The dimensions of this rectangle are approximately 18 Å×8 Å×9 Å×17 Å and the thickness of the pocket is approximately 7 Å.

Advanced docking procedures were employed for the rational design of leflunomide metabolite (LFM) analogs with a high likelihood to bind favorably to the catalytic site within the kinase domain of BTK. The compound LFM-A13, for which we calculated a K$_i$ value of 1.4 μM, inhibited human BTK in vitro with an IC$_{50}$ value of 17.2±0.8 μM. Similarly, LFM-A13 inhibited recombinant BTK expressed in a baculovirus expression vector system with an IC$_{50}$ value of 2.5 μM. The energetically favorable position of LFM-A13 in the binding pocket is such that its aromatic ring is close to Tyr$^{476}$, and its substitutent group is sandwiched is between residues Arg$^{525}$ and Asp$^{539}$. In addition, LFM-A13 is capable of favorable hydrogen bonding interactions with BTK via Asp$^{539}$ and Arg$^{525}$ residues.

Besides its remarkable potency in BTK kinase assays, LFM-A13 was also discovered to be a highly specific inhibitor of BTK. Even at concentrations as high as 100 μg/ml (~278 μM), this novel inhibitor did not affect the enzymatic activity of other protein tyrosine kinases, including JAK1, JAK3, HCK, EGF-Receptor Kinase (EGFR), and Insulin-Receptor Kinase (IRK).

In accordance with the anti-apoptotic function of BTK, treatment of BTK$^+$ B-lineage leukemic cells with LFM-A13 enhanced their sensitivity to ceramide-or vincristine-induced apoptosis.

Crystal Structures of Leflunomide Metabolite and Its Analogs

The leflunomide metabolite (LFM) and two of its analogs (LFM-A12, LFM-A13) were crystallized using various solvents by evaporation or liquid-liquid diffusion. X-ray data from single crystals were collected using a SMART CCD area detector (Bruker Analytical X-ray Systems, Madison, Wis.) with MoKα radiation (λ=0.7107 Å). The space group was determined based on systematic absences and intensity statistics. A direct methods solution provided most of the non-hydrogen atoms from the electron density map. Several full-matrix least squares/difference Fourier cycles were performed to locate the remaining non-hydrogen atoms. All non-hydrogen atoms were refined with anisotropic thermal parameters. Hydrogen atoms were placed in ideal positions and refined as riding atoms with relative isotropic temperature factors. The structure was refined using full-matrix least-squares on F$^2$. Crystal structure calculations were performed using a Silicon Graphics INDY R4400-SC computer (Silicon Graphics Inc., Mountain View, Calif.) or a Pentium computer using the SHELXTL V 5.0 suite of programs (Sheldrick, G., 5.0 Ed., Bruker Analytical X-ray Systems, Madison, Wis.).

Construction of the Homology Model for the Kinase Domain of BTK

A homology model of BTK was constructed using crystal structures of homologous kinase domains of protein kinases HCK, FGFR, IRK, and cAPK (Sicheri, F., Moarefi, I., and Kuriyan, J. (1997) Nature 385(6617), 602–9; Mohammadi, M., et al. (1997) Science 276(5314), 955–60; Hubbard, S. R. (1997) The E. M B. O. Journal 16(18), 5572–5581; Zheng, J., et al. (1993) Acta Cryst. D49, 362–365). The homology modeling of BTK was carried out by first obtaining the protein sequence of BTK (Swiss-Prot # Q06187, Univ. of Geneva, Geneva, Switzerland) from GenBank (National Center for Biotechnology Information, Bethesda, Md.). Next, the most reasonable sequence alignment between the BTK kinase and a coordinate template was determined. This was done by first superimposing the Cα coordinates of the kinase domains of HCK, FGFR, IRK, and cAPK using the InsightII program ((1996), Molecular Simulations, Inc., San Diego, Calif.) to provide the best overall structural comparison. All four sequences were then aligned based on the superimposition of their structures (amino acid sequences were aligned together if their Cα positions were spatially related to each other). The sequence alignment accommodated such features as loops in a protein which differed from the other protein sequences. The structural superimposition was done using the Homology module of the InsightII ((1996), Molecular Simulations, Inc., San Diego. Calif.)

program and a Silicon Graphics INDIGO2 computer (Silicon Graphics Inc., Mountain View, Calif.). The sequence alignment was manually adjusted based on the previously mentioned considerations, and produced a sequence variation profile for each superimposed Cα position. The sequence variation profile served as a basis for the next procedure, which was sequence alignment of all four proteins with BTK kinase. In this procedure. the sequence of BTK kinase was read into the program and manually aligned with the four known kinase proteins based on the sequence variation profile described previously.

Next a set of 3D coordinates was assigned to the BTK kinase sequence using the 3D coordinates of HCK as a template, which employed the Homology module within the InsightII program ((1996), Molecular Simulations, Inc., San Diego, Calif.). The coordinates for a loop region where a sequence insertion occurs (relative to HCK without the loop) was chosen from a limited number of possibilities automatically generated by the program and manually adjusted to a more ideal geometry using the program CHAIN (Sack, J. S. (1988) *J. Mol. Graphics* 6, 244–245). Finally, the constructed model of BTK was subjected to energy minimization using the X-plor program (Brunger, A. T. (1992), New Haven, Conn.) so that any steric strain introduced during the model-building process could be relieved. The model was lo screened for unfavorable steric contacts and if necessary such side chains were remodeled either by using a rotamner library database or by manually rotating the respective side chains. The final homology model of the BTK kinase domain had an RMS deviation of 0.01 Å from ideal bond lengths and 2.2° from ideal bond angles after energy minimization. The homology model of BTK was then used, in conjunction with model coordinates of LFM and its analogs (which were later compared with crystal structures), for modeling studies of the BTK/inhibitor complexes.

Docking Procedure using Homology Model of BTK Kinase Domain. Modeling of the BTK/LFM analog complexes was done using the Docking module within the program INSIGHTII and using the Affinity suite of programs for automatically docking a ligand to the receptor. Energy-minimized coordinates for each LFM molecule were generated and interactively docked into the ATP binding site of BTK based on the position of quercetin in the HCK/quercetin crystal structure (Sicheri, F., et al., J. (1997) *Nature* 385 (6617), 602–9). The hydrogen atoms on the kinase domain of BTK were generated and potentials were assigned to both receptor and ligand prior to the start of the docking procedure. The docking method in the Insightll program used the CVFF force field and a Monte Carlo search strategy to search for and evaluate docked structures. While the coordinates for the bulk of the receptor were kept fixed, a defined region of the binding site was allowed to relax, thereby allowing the protein to adjust to the binding of different inhibitors. A binding set was defined within a distance of 5 Å from the inhibitor, allowing residues within this distance to shift and/or rotate to energetically favorable positions to accommodate the ligand. An assembly was defined consisting of the receptor and inhibitor molecule and docking was performed using the fixed docking mode. Calculations approximating hydrophobic and hydrophilic interactions were used to determine the ten best docking positions of each LFM analog in the BTK catalytic site. The various docked positions of each LFM analog was qualitatively evaluated using Ludi (Bohm, H. J. (1992) *J. Comput. Aided. Mol. Des.* 6(6), 593–606; and Bohm, H. J. (1994) *J. Comput. Aided Mol. Des.* 8(3), 243–56) in INSIGHTII which was used to estimate a binding constant ($K_i$) for each compound in order to rank their relative binding capabilities and predicted inhibition of BTK. The $K_i$ trends for the LFM analogs were compared with the trend of the experimentally determined tyrosine kinase inhibition $IC_5$ values for the compounds, in order to elucidate the structure-activity relationships (SAR) determining the potency of LFM analogs.

Recombinant Baculovirus Construction and Protein Expression. Sf21 (IPLB-SF21-AE) cells (Vassilev, A., et al. (1998) *J. Biol. Chem.*, 274, 1646–1656) derived from the ovarian tissue of the fall armyworm *Spodotera frugiperda*, were obtained from Invitrogen and maintained at 26–28° C. in Grace's insect cell medium supplemented with 10% FBS and 1.0% antibiotic/antimycotic (GIBCO-BRL). Stock cells were maintained in suspension at $0.2–1.6 \times 10^6$/ml in 600 ml total culture volume in 1 L Bellco spinner flasks at 60–90 rpm. Cell viability was maintained at 95–100% as determined by trypan blue dye exclusion.

Recombinant baculovirus containing the murine BTK gene was constructed as described (Vassilev, A., et al. (1998) *J. Biol. Chem.*, 274, 1646–1656). In brief, the gene encoding BTK was excised from pBluescript $SKII^+$ vector (Stratagene, La Jolla, Calif.) digestion with BamHI and this fragment was then ligated into pFastBac1 (Gibco-BRL). The resulting vector, pFastBac1-BTK, was then used to generate the recombinant baculovirus by site-specific transposition in *E. coli* DH10Bac cells (Gibco-BRL) which harbor a baculovirus shuttle vector (bacmid), bMON14272. The resulting recombinant bacmid DNA was introduced into insect cells by transfection with the standard liposome-mediated method using Cellfectin reagent (Gibco-BRL). Four days later, transfection supernatants were harvested for subsequent plaque purification and analyzed as above. Kinase-dead BTK was generated as described (Vassilev, A., et al. (1998) *J. Biol. Chem.*, 274, 1646–1656) and cloned into the baculovirus expression vector as described above for wild type BTK. Baculovirus expression vectors for JAK1 and JAK3 kinases were constructed and introduced into insect cells, as previously reported (Goodman, P. A., et al. (1998) *J. Biol. Chem.* 273, 17742–48).

Immunoprecipitation of Recombinant Proteins from Insect Cells. Sf21 cells were infected with a baculovirus expression vector for BTK, JAK1, or JAK3, as indicated in brief description of the figures. Cells were harvested, lysed (10 mM Tris pH7.6, 100 mM NaCl, 1% Nonidet P-40, 10% glycerol, 50 mM NaF, 100 mM $Na_3VO_4$, 50 µg/ml phenylmethylsulfonyl fluoride, 10 µg/ml aprotonin, µg/ml leupeptin), and the kinases were immnunoprecipitated from the lysates, as reported (Vassilev, A., et al. (1998) *J. Biol. Chem.*, 274, 1646–1656). Antibodies used for immunoprecipitations from insect cells are as follows: Polyclonal rabbit anti-BTK serum, (Mahajan, S., et al. (1995) *Mol. Cell. Biol.* 15, 5304–11) polyclonal rabbit anti-JAK1 (HR-785), cat# sc-277, rabbit polyclonal IgG affinity purified, 0.1 mg/ml, Santa Cruz Biotechnology, and polyclonal rabbit anti-JAK3 (C-21, cat # sc-513, rabbit polyclonal IgG affinity purified, 0.2 mg/ml, Santa Cruz Biotechnology). Kinase assays were perforrned following a 1 hour exposure of the immunoprecipitated tyrosine kinases to the test compounds, as described in detail elsewhere (Mahajan, S., et al. (1995) *Mol. Cell. Biol.* 15, 5304–11; and Uckun, F. M., et al. (1996) *Science* 22, 1096–1100). The immunoprecipitates were subjected to Western blot analysis as previously described (Vassilev, A., et al. (1998) *J. Biol. Chem.*, 274, 1646–1656).

Cell lines, Reagents, and Biochemical Assays. The establishment and characterization of DT40 lymphoma B cell line as well as BTK-deficient DT40 and its derivatives reconstituted with wild-type or mutant human BTK have been previously reported (Uckun, F. M., et al. (1996) *Science* 22, 1096–1100). Equal amounts of BTK protein were detected by Western blot analysis in all of the BTK-deficient DT-40 clones transfected with wild-type or mutated human BTK genes but no BTK protein was detectable in the untransfected BTK-deficient DT-40 cells (Uckun, F. M., et al. (1996) *Science* 22, 1096–1100). All cell lines derived from the chicken B-cell line DT40 were maintained in RPMI 1640 medium supplemented with 10% heat-inactivated fetal bovine serum, 1% heat-inactivated chicken serum, 2 mM glutamine, penicillin, and strepotmycin. Cells were grown at 37° C. in a 5% $CO_2$ water saturated atmosphere. The BTK positive human B-lineage leukemia cell lines NALM-6 and ALL-1 were maintained in RPMI 1640 medium supplemented with 10% heat-inactivated fetal bovine serum (Uckun, F. M., et al. (1995) *Science* 267, 886–91). COS-7 simian kidney cell line and HepG2 human hepatoma cell line were obtained from ATCC.

Antibodies directed against BTK, JAK1, JAK3, and HCK have been described previously (Mahajan, S., et al. (1995) *Mol. Cell. Biol.* 15, 5304–11; Vassilev, A., et al. (1998) *J. Biol. Chem.*, 274. 1646–1656; Goodman, P. A., et al. (1998) *J. Biol. Chem.* 273, 17742–48; and Uckun, F. M., et al. (1996) *Science* 22, 1096–1100). Polyclonal antibodies to BTK were generated by immunization of rabbits with glutathione S-transferase (GST) fusion proteins (Pharmacia Biotech Inc.) containing the first 150 amino acids of BTK. The monoclonal anti-Fas antibody (F22120) was obtained from the Transduction Laboratories, Inc. (Lexington, Ky.). Immunoprecipitations, immune-complex protein kinase assays, and imnnunoblotting using the ECL chemiluminescence detection system (Amersham Life Sciences) were conducted as described previously (Mahajan, S., et al. (1995) *Mol. Cell. Biol.* 15, 5304–11; Vassilev, A., et al. (1998) *J. Biol. Chem.*, 274, 1646–1656; Goodman, P. A., et al. (1998) *J. Biol. Chem.* 273, 17742–48; and Uckun, F. M., et al. (1996) *Science* 22, 1096–1100). Following electrophoresis, kinase gels were dried onto Whatman 3M filter paper and subjected to phosphoimaging on a Molecular Imager (Bio-Rad, Hercules, Calif.) as well as autoradiography on film. Similarly, all chemiluminescent BTK Western blots were subjected to three dimesional densitometric scanning using the Molecular Imager and Imaging Densitometer using the Molecular Analyst/Macontosh version 2.1 software following the specifications of the manufacturer (Bio-Rad). For each drug concentration, a BTK kinase activity index was determined by comparing the ratios of the kinase activity in phosphorimager units (PIU) and density of the protein bands in densitometric scanning units (DSU) to those of the baseline sample and using the formula: Activity Index=[PIU of kinase band/DSU of BTK protein band]$_{test\ sample}$: [PIU of kinase band/DSU of BTK protein band]$_{baseline\ contol\ sample}$. GST-IGα was sometimes used as an exogenous substrate for BTK immune-complex protein kinase assays, as described (Mahajan, S., et al. (1995) *Mol. Cell. Biol.* 15, 5304–11). Horse radish peroxidase-conjugated sheep anti-mouse, donkey anti-rabbit secondary antibodies and ECL reagents were purchased from Amersham (Oakbrook, Ill.). For insulin receptor kinase (IRK) assays, HepG2 human hepatoma cells grown to approximately 80% confluency were washed once with serum-free DMEM and staaved for 3 hour at 37° in a $CO_2$ incubator. Subsequently, cells were stimulated with insulin (Eli Lilly, cat# C.P-410;10 units/ml/$10 \times 10^6$ cells) for 10 minutes at room temperature. Following this IRK activation step, cells were washed once with serum free medium, lysed in NP-40 buffer and IRK was immunoprecipitated from the lysates with an anti-IR$_b$ antibody (Santa Cruz, Cat.# sc-711, polyclonal IgG). Prior to performing the immune complex kinase assays, the beads were equilibrated with the kinase buffer (30 mM Hepes pH 7.4, 30 mM NaCl, 8 mM MgC12, 4 mM $MnCl_2$).

For HCK kinase assays, we used HCK-transfected COS-7 cells. The cloning and expression of HCK in COS-7 cells has been described previously (Saouaf, S. J., et al. (1995) *J. Biol. Chem.* 270, 27072–8). The pSV7c-HCK plasmid was transfected into $2 \times 10^6$ COS-7 cells using Lipofectamine (GIBCO/BRL), and the cells were harvested 48 hours later. The cells were lysed in NP-40 buffer and HCK was immunoprecipitated from the whole cell lysates with an anti-HCK antibody.

Apoptosis Assays

To induce apoptosis, cells were treated with an agonistic anti-Fas/APO-1 antibody (Bender MedSystems, City/State, Lot. 04/1295) at 0.1 μg/ml and 0.5 μg/ml final concentrations, vincristine (vincristine sulfate, USP; Pharmacia, NDC 0013-7466-86, Lot VCB019) at 10 ng/ml and 100 ng/ml final concentrations, or C2-ceramide (Biomol, Lot M8107) at 10 μM, 50 μM, and/or 100 μM final concentrations. MC540 binding (as an early marker of apoptosis) and PI permeability (as a marker of advanced stage apoptosis) were simultaneously measured in DT-40 cells 24 hours after exposure to C2-ceramide, anti-Fas, or vincristine, as previously described (Uckun, F. M., et al. (1996) *Science* 22, 1096–1100). Whole cells were analyzed using a FACStar Plus flow cytometer (Becton Dickinson, San Jose, Calif.). All analysis were done using 488 nm excitation from an argon laser. MC540 and PI emissions were split with a 600 nm short pass dichroic mirror and a 575 nm band pass filter was placed in front of one photomultiplier tube to measure MC540 emission and a 635 nm band pass filter was used for PI emission. In order to examine the effects of the lead BTK inhibitor on ceramide-induced apoptosis in BCR-ABL positive human ALL cell line ALL-1, cells were treated for 4 hours at 37° C. with 10 μM C2-ceramide in the presence or absence of the inhibitor (200 μM LFM-A13). Subsequently, cells were washed, stained with PI and MC540, and the apoptotic fractions were determined by multiparameter flow cytometry, as described (Uckun, F. M., et al. (1996) *Science* 22, 1096–1100).

To detect apoptotic fragmentation of DNA, DT-40 cells were harvested 24 hours after exposure to anti-Fps, C2-ceramide, or vincristine. Similarly, B18.2, NALM-6, and ALL-1 cells were treated with LFM-A13 (100 μM), vincristine (VCR) (10 ng/ml), C2-Ceramide (C2-CER) (10 μM), LFM-A13 (100 μM)+VCR (10 ng/ml), LFM-A13 (100 μM)+C2-CER (10 μM) for 24 hours at 37° C. DNA was prepared from Triton-X-100 lysates for analysis of fragmentation (Uckun, F. M., et al. (1996) *Science* 22, 1096–1100). In brief, cells were lysed in hypotonic 10 mmol/L Tris-HCl (pH 7.4), 1 mmol/L EDTA, 0.2% Triton-X-100 detergent; and subsequently centrifuged at 11,000 g. To detect apoptosis-associated DNA fragmentation, supernatants were electrophoresced on a 1.2% agarose gel, and the DNA fragments were visualized by ultraviolet light after staining with ethidium bromide.

BTK is an Anti-Apoptotic Enzyme

Figure 9A:
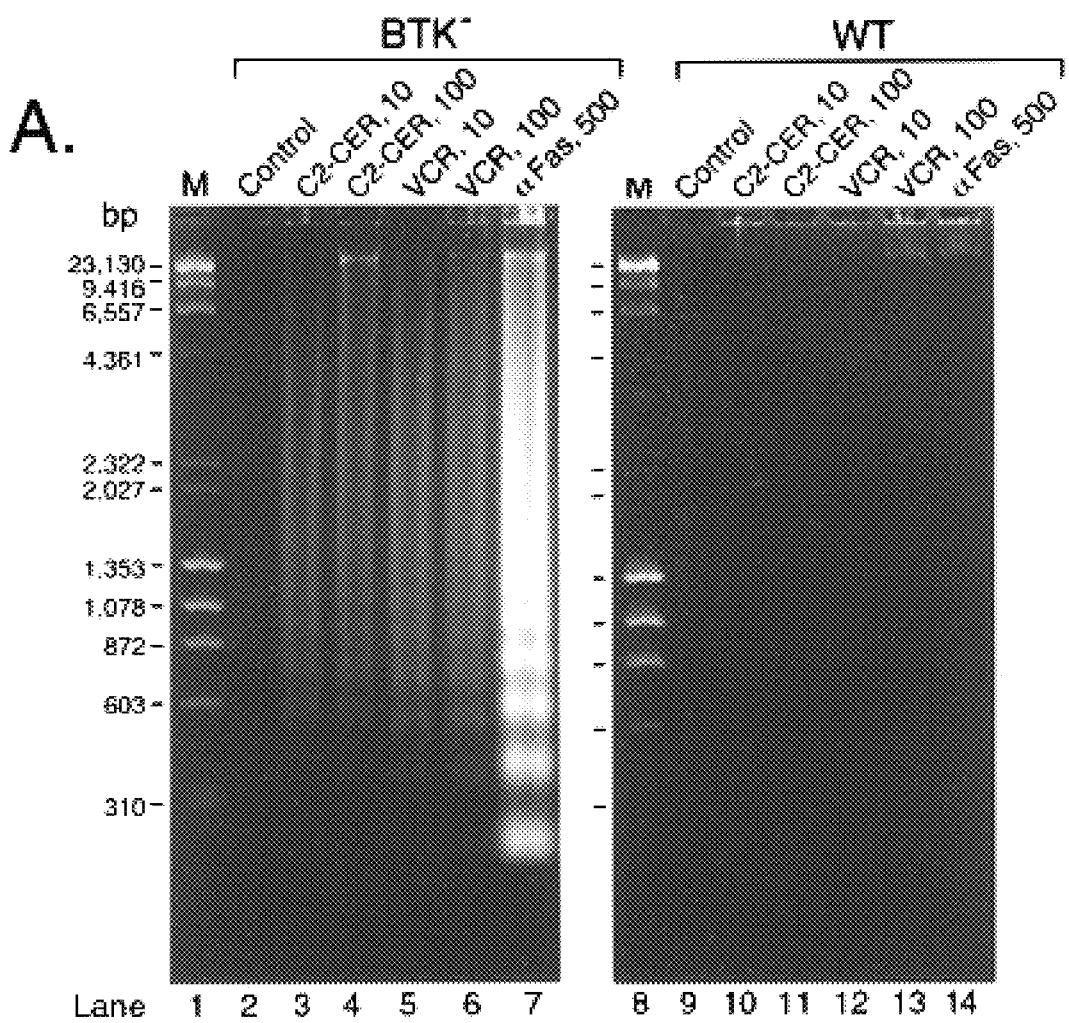
FIGS. 9A–9B: The anti-apoptotic function of BTK. Wild-type and BTK-deficient (BTK-) DT-40 lymphoma B cells (FIG. 9A) as well as BTK-DT-40 cells reconstituted with wild-type or mutant human BTK (FIG. 9B) were treated with $C_2$-CER, vincristine (VCR), or anti-Fas antibody, as described in the Examples. BTK-deficient DT-40 (BTK-) cells expressing wild-type BTK, BTK(Arg$^{525}$®Gln), BTK (Arg$^{28}$®Cys), and BTK(Arg$^{307}$®Ala) were designated as BTK⁻, rBTK(WT), BTK-, rBTK(K-), BTK⁻, rBTK(mPH) and BTK-, rBTK(mSH2), respectively. Vehicle (0.1% DMSO in PBS) treated as well as drug treated cells were maintained in culture medium for 24 hours at 37° C. and 5% $CO_2$ before harvesting. DNA from Triton-X-100 lysates was analyzed for fragmentation as described above. Uckun, F. M., et al. (1996) *Science* 22, 1096–1100.

The anti-apoptotic activity of BTK was evaluated by comparing the effects of the apoptosis-inducing agents C2-ceramide, vincristine, and anti-Fas monoclonal antibody on wild-type DT-40 chicken B lymphoma cells to those on a BTK-deficient subdlone of DT-40 cells that was established by homologous recombination knockout (Uckun, F. M., et al. (1996) *Science* 22, 1096–1100). Ceramide, the product of ceramide synthase and sphingomyelinase, has been shown to function as a second messenger that transmits membrane-induced apoptotic signals, including the Fas-mediated and TNF receptor-mediated death signals, to downstream effectors (Enari, M., Hase, A., and Nagata, S. (1995) *EMBO J.* 14, 5201–5208). The use of vincristine, a commonly used anti-leukemia/lymphoma drug, results in a time-dependent accumulation of ceramide in treated cells which leads to apoptosis. On agarose gels, DNA from Triton-X-100 lysates of anti-Fas treated BTK-deficient DT-40 cells showed a ladder-like fragmentation pattern consistent with apoptosis, whereas no DNA fragmentation was observed in wild-type DT-40 cells (FIG. 9A, Lane 7 vs Lane 14). Thus, the anti-Fas antibody treatment caused apoptosis in BTK-deficient DT-40 cells, but not in wild-type DT-40 cells consistent the fact that BTK is an inhibitor of the Fas-associated death inducing signaling complex (DISC) (Vassilev, A., et al. (1998) *J. Biol. Chem.*, 274, 1646–1656). Notably, treatment of BTK-deficient DT-40 cells with C2-ceramide (=N-acetylspingosine; a synthetic cell-permeable ceramide analog) or vincristine was able to recapitulate the effects of anti-Fas in inducing oligonucleo-somal DNA fragmentation on agarose gel electrophoresis, whereas wild-type DT-40 cells were resistant to both agents, confirrning the function of BTK as a negative regulator of apoptosis (FIG. 9A).

Figure 9B:
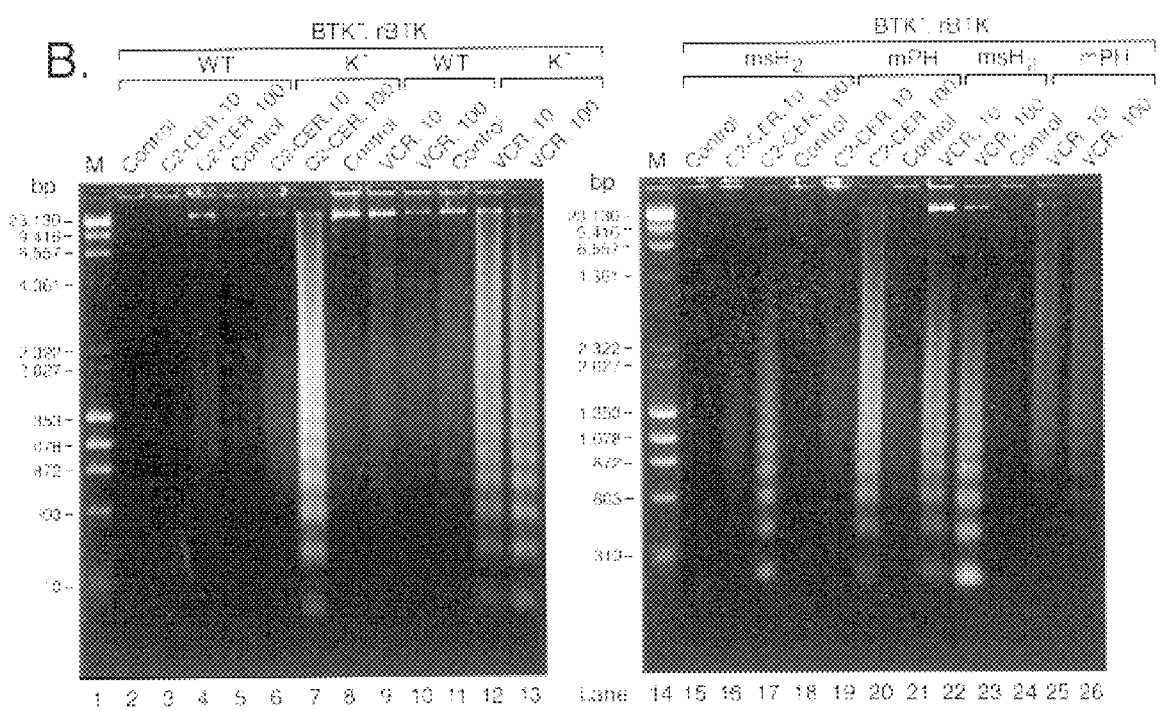

In order to examine the participation of the various domains of BTK in its anti-apoptotic function, we introduced wild-type human BTK gene as well as human BTK genes harboring mutations either in the catalytic domain ($Arg^{525}$ to Gln), SH2 domain ($Arg^{307}$ to Ala), or PH domain ($Arg^{28}$ to Cys) into the BTK-deficient DT-40 cells (Enari, M., Hase, A., and Nagata, S. (1995) *EMBO J.* 14, 5201–5208). As evidenced in FIG. 9B, BTK-deficient DT-40 cells reconstituted with wild-type human BTK gene (WT) did not undergo apoptosis after treatment with C2-ceramide (Lanes 2–4) or vincristine (Lanes 8–10), whereas DT-40 subclones expressing human BTK with mutations in the kinase (K-) (Lanes 5–7 and 11–13), SH2 (mSH2) (Lanes 15–17 and 21–23), or PH (mPH) domains (Lanes 18–20 and 24–26) did. Thus, the kinase, SH2, and PH domains of BTK are important for its anti-apoptotic function.

Homology Model of BTK Kinase Domain

Figure 10A:
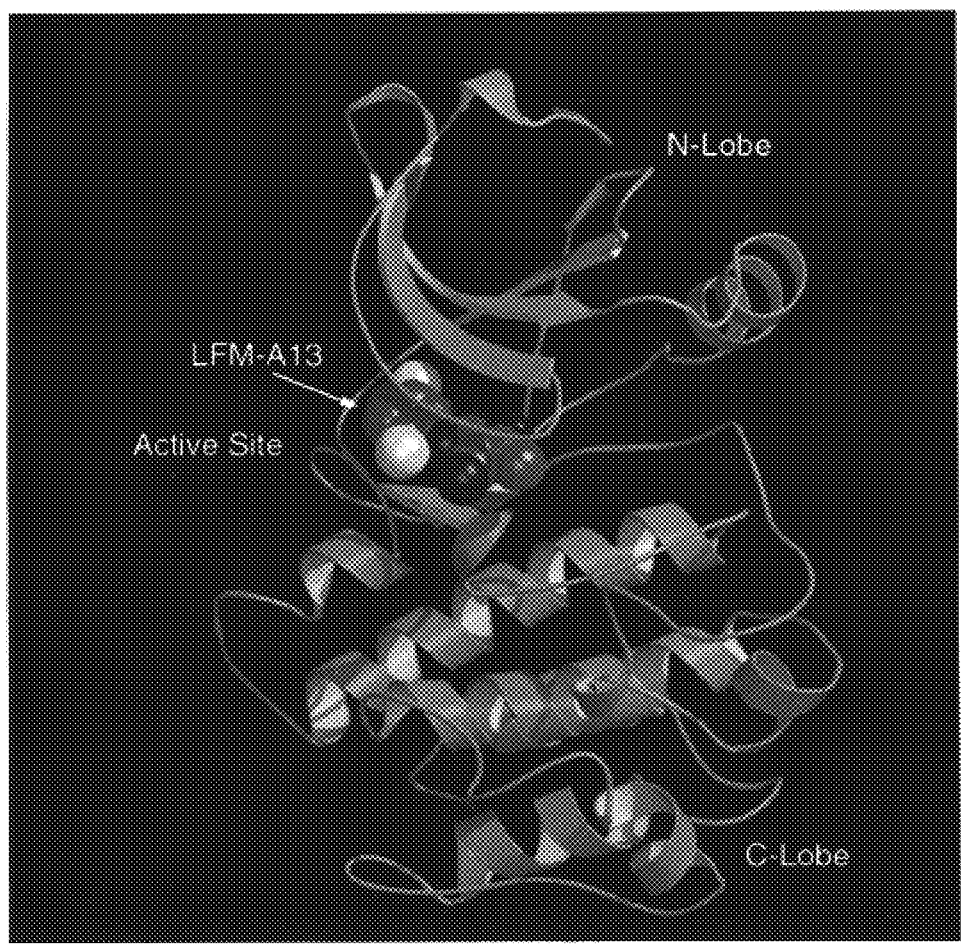
FIGS. 10A–10B: Homology model of BTK Kinase domain.
Figure 10B:
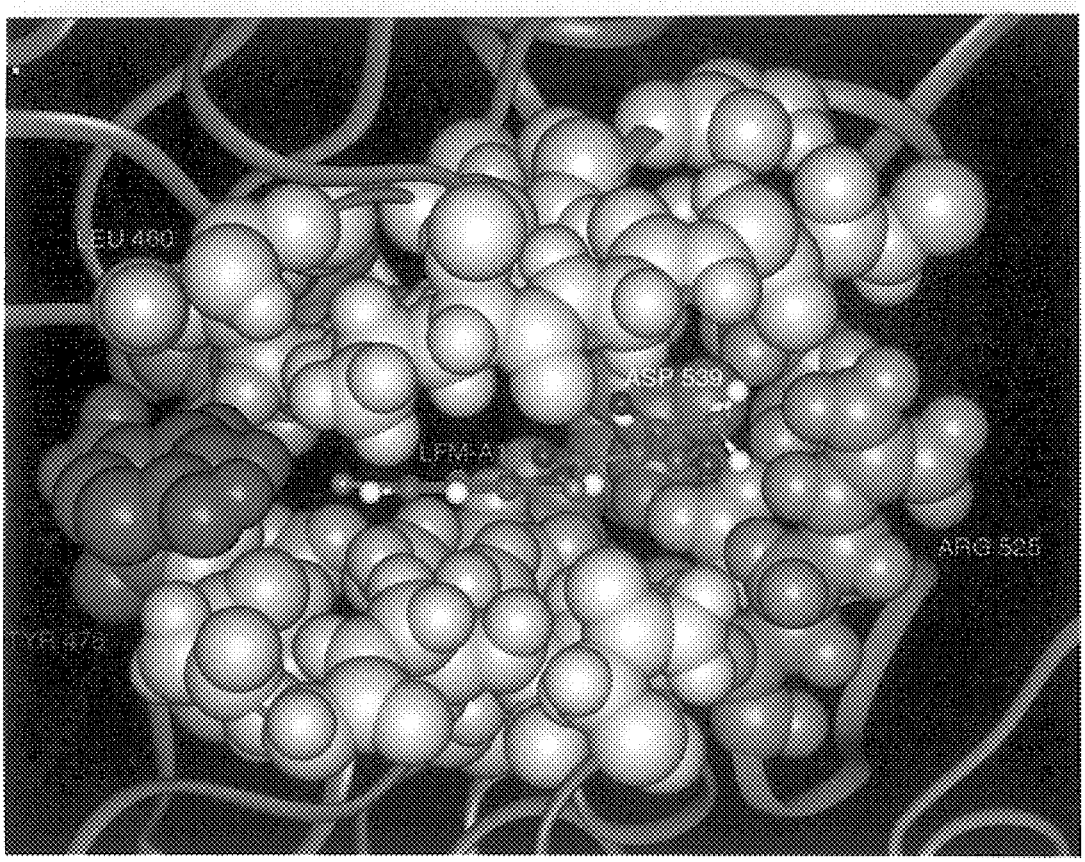

The three-dimensional coordinates of BTK used in the protein/inhibitor modeling studies were constructed based on a structural alignment with the sequences of known crystal structures for four protein kinase domains (kinase domains of HCK, FGFR, IRK, and cAPK), as detailed above (Sicheri, F., Moarefi, I., and Kuriyan, J. (1997) *Nature* 385(6617), 602–9; Mohammadi, M., et al. (1997) *Science* 276(5314), 955–60; Hubbard, S. R. (1997) *The E. M B. O. Journal* 16(18), 5572–5581; Zheng, J., et al. (1993) *Acta Cryst.* D49, 362–365). The modeled BTK kinase domain (FIG. 10A) has the expected protein kinase fold with the catalytic site in the center dividing the kinase domain into two lobes. It is composed of a smaller N-terminal lobe connected by a flexible hinge to a larger C-terminal lobe. The N-terminal lobe is rich in β-strands, while the C-terminal region is mostly helical. The catalytic site is defmed by two β-sheets that form an interface at the cleft between the two lobes. It is in this catalytic region where small molecule inhibitors can bind. Our modeling studies revealed that the catalytic site of the BTK kinase domain is composed of a distinct planar rectangular binding pocket near the hinge region. The rectangular binding region is defined by residues $Leu^{460}$, $Tyr^{476}$, $Arg^{525}$ and $Asp^{539}$ which occupy the comers of the rectangle. The dimensions of this rectangle are approximately 18 Å×8 Å×9 Å×17 Å and the thickness of the pocket is approximately 7 Å (FIG. 10B). The far left comer of the rectangle can be visualized as beginning close to the hinge region at $Leu^{460}$ (shown in yellow, FIG. 10B) and extending 8 Å towards the upper right to $Asp^{539}$ (shown in blue, FIG. 10B). This is the shortest side of the binding pocket and is located closer to the inner core of the protein. The left side of the pocket, which is the longest, extends from $Leu^{460}$ and traces 18 Å along the hinge region up to $Tyr^{476}$ (shown in green, FIG. 10B). The right side of the rectangular pocket, opposite to the hinge region, extends about 9 Å from $Asp^{539}$ to $Arg^{525}$ (shown in pink, FIG. 10B), which is immediately adjacent to the binding subsites for the sugar and triphosphate groups of ATP. The hinge region of the binding site is composed of residues 472 to 481. The solvent exposed or fourth side of the rectangle extends 17 Å along the slot-shaped opening to the catalytic site from $Tyr^{476}$ to $Arg^{525}$. The binding pocket is wider at the solvent accessible region, it narrows towards the innermost region of the binding site, and overall it is relatively shallow with a thickness of about 7 Å. The volume of the pocket is approximately 500 Å$^3$.

While most of the catalytic site residues of the BTK kinase domain were conserved relative to other tyrosine kinases, a few specific variations were observed. Residues $Asn^{526}$ and $Asp^{539}$ (opposite the hinge) are conserved in EGFR, IRK, HCK, and BTK. Residue $Thr^{474}$ in the hinge region changes to Met in IRK, JAK1 and JAK3 and residue $Tyr^{476}$ in the hinge region changes to Leu in EGFR and IRK. Residue $Ser^{538}$ of BTK is not conserved in other kinases, but changes to Gly in JAK1 and IRK, to Thr in EGFR, and to Ala in FGF-Receptor, JAK3, and HCK. One region of the binding site contains $Cys^{481}$ in BTK which is more hydrophobic than the corresponding residue of PDGF-Receptor (Asp), FGF-Receptor (Asn), and IRK (Asp). These residue identity differences provide a basis for designing selective inhibitors of the BTK kinase domain.

Structure-Based Design and Synthesis of LFM Analogs with Potent BTK-Inhibitory Activity In modeling studies aimed at identifying LFM analogs with a high likelihood to bind favorably to the catalytic site of the kinase domain of BTK, we chose to evaluate the estimated $K_i$ values which quantitate predicted binding interactions between the inhibitor and residues in the catalytic site of BTK. Each of the small molecule LFM analogs was individually modeled into the catalytic site of the BTK kinase domain using an advanced docking procedure (see Experimental Procedure described above). The position of quercetin in the HCK crystal structure (Sicheri et al., 1997, *Nature* 385:602) was used as a template to obtain a reasonable starting point for the docking procedure. The various docked positions of each LFM analog were qualitatively evaluated using a scoring procedure and consequently compared with the $IC_{50}$ values of the compounds in cell-free BTK inhibition assays. Table 1 shows the interaction scores, calculated $K_i$ values and measured $IC_{50}$ values for LFM and its analogs with BTK.

Figure 11:
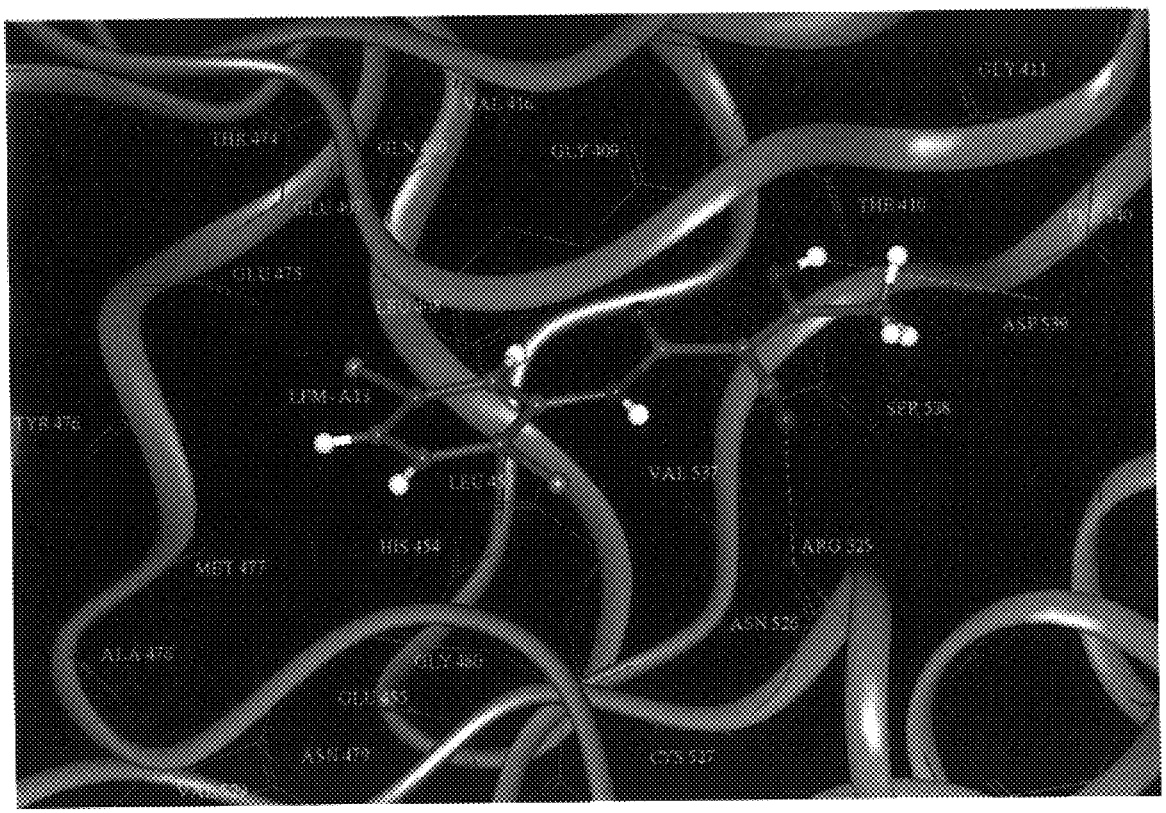
FIG. 11: Docked position of the LFM-A13 molecule (multi-color) at the catalytic site (blue ribbon) of the kinase domain of BTK. Dashed lines represent hydrogen bonds between LFM-A13 and the kinase domain residues of BTK.

The inhibitors in our modeling studies were sandwiched by two regions of mostly hydrophobic residues. The region above the docked inhibitor consisted of residues $Leu^{408}$, $Val^{416}$, and $Lys^{430}$, and the residues below the docked inhibitor included BTK residues $Leu^{528}$, $Ser^{538}$, $Gly^{480}$, and $Cys^{481}$. Of all the reported compounds evaluated in our modeling studies (Table 1), we predicted that compound LFM-A13 would provide the strongest binding to BTK. The positions of the critical residues in the active site of the BTK and the docked position of the compound LFM-A13 is shown in FIG. 11. Of all the possible orientations of this molecule bound to the catalytic site, the one shown in FIG. 11 showed the highest interaction score with BTK. This high interaction score is indicative of an energetically favored binding mode, with a correspondingly low calculated $K_i$ value of 1.4 μM. This binding position of LFM-A13 is such that the aromatic ring of the inhibitor faces the $Tyr^{476}$ residue and the flexible side chain extends towards the $Asp^{539}$ and $Arg^{525}$ residues. The aromatic ring is also sandwiched between the hydrophobic residues $Leu^{408}$ and $Val^{416}$ above, and $Gly^{480}$ and $Leu^{528}$ below. Residue $Ser^{538}$ lies below the flexible side chain of the inhibitor and the end of the side chain is located between residues $Asp^{539}$ and $Arg^{525}$. This position closely resembles that of the ATP analog position found in the IRK complex crystal structure (Hubbard, EMBO J, 16(18): 5572–5581, 1997. According to our modeling studies, the O3 atom in the hydroxyl group of LFM-A13 would form a hydrogen bond with Asp539:O and its O4 atom would form a hydrogen bond with Arg525:N.

Figure 12:
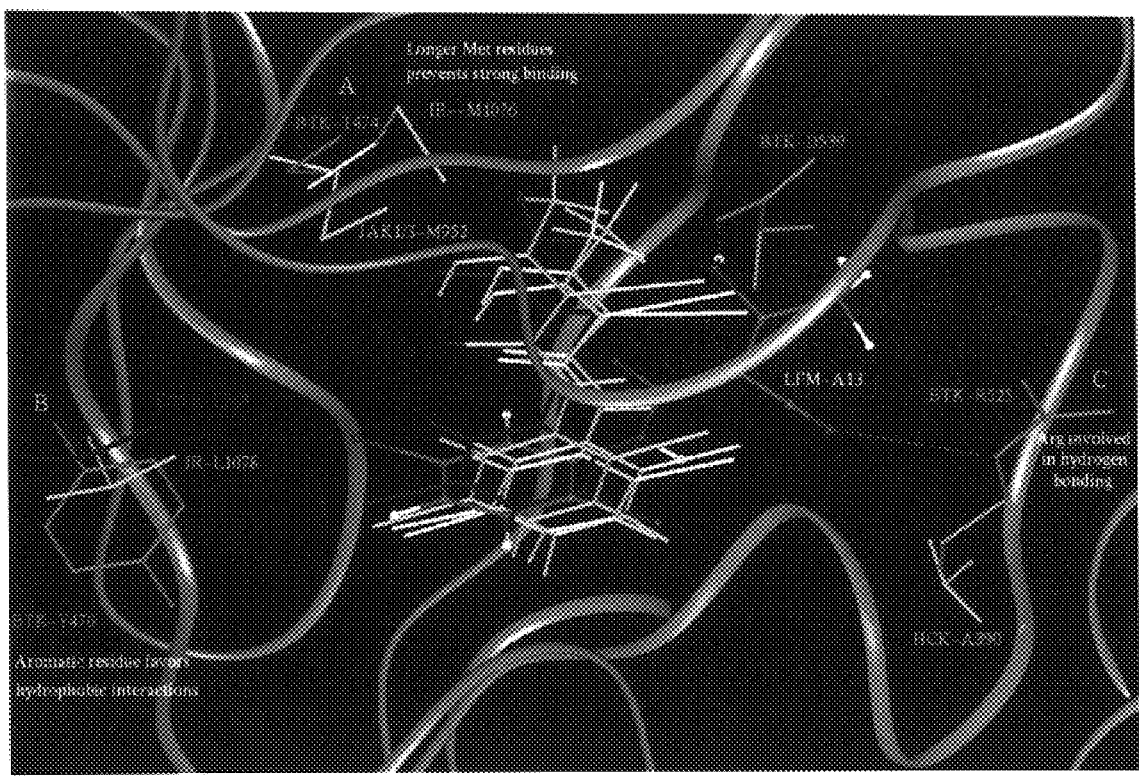
FIG. 12: Superimposed docked positions of LFM (purple), LFM-A12 (red) and LFM-A13 (multi-color) in the catalytic site (blue ribbon) of the kinase domain of BTK.

FIG. 12 illustrates the superimposed docked positions of LFM-A13 in the catalytic site of BTK, together with compounds LFM and LFM-A12. The molecules LFM and LFM-A12 are docked such that they lie along the hinge region, corresponding to the quercetin position in the HCK crystal structure. The aromatic ring of these molecules are close to $Tyr^{476}$, and the end of the side chain is sandwiched between residues $Asp^{539}$ and $Thr^{474}$. The $CF_3$ group in these molecules points toward the solvent accessible region and are surrounded by $Leu^{408}$ above and $Gly^{480}$ below. The OH group of LFM is hydrogen-bonded to an oxygen atom of $Asp^{539}$, and for LFM-A12, the same group is hydrogen bonded to an oxygen atom of $Thr^{474}$. All LFM analogs listed in Table 1, except LFM-A13, lie along the hinge region like LFM or LFM-A12 and their side chains are sandwiched between $Asp^{525}$ and $Thr^{474}$.

A comparison of the docked positions of LFM, LFM-A12, and LFM-A13 in the BTK active site shows that although the aromatic portion of the three molecules are roughly in the same region (which is also true for the other inactive LFM analogs), the side chain of LFM-A13 is tilted away from those of the others and is sandwiched between residues $Asp^{539}$ and $Arg^{525}$. This rotation is likely due to a more favorable orientation of the 2,5-dibromo groups of LFM-A13. This slightly tilted position and the larger Br groups afford two advantages for the interaction of LFM-A13 with the active site residues of BTK.

The first advantage is that LFM-A13 is able to form two hydrogen bonds with active site residues $Asp^{539}$ and $Arg^{525}$, whereas the inactive LFM analogs form only one hydrogen bond each with the $Thr^{474}$ or $Asp^{539}$ of BTK. The second advantage for binding is the higher contact area of LFM-A13 with active site residues of BTK, relative to the other 12 inactive LFM analogs, which leads to a greater hydrophobic interaction for LFM-A13. This feature is reflected by the correspondingly higher lipophilic score for LFM-A13 in Table 1.

The results from the modeling studies discussed above prompted the hypothesis that LFM-A13 would exhibit potent BTK-inhibitory activity. In order to test this hypothesis and validate the predictive value of the described BTK homology model, we synthesized LFM-A13, LFM, and 11 other LFM analogs listed in Table 1. The structures of LFM, LFM-A12, and LFM-A13 were determined by single crystal X-ray diffraction (crystal data, experimental parameters, and refinement statistics for these compounds are summarized in Table 2). All structures were found to have a planar conformation and all bond lengths and angles were in the expected range.

Figure 13:
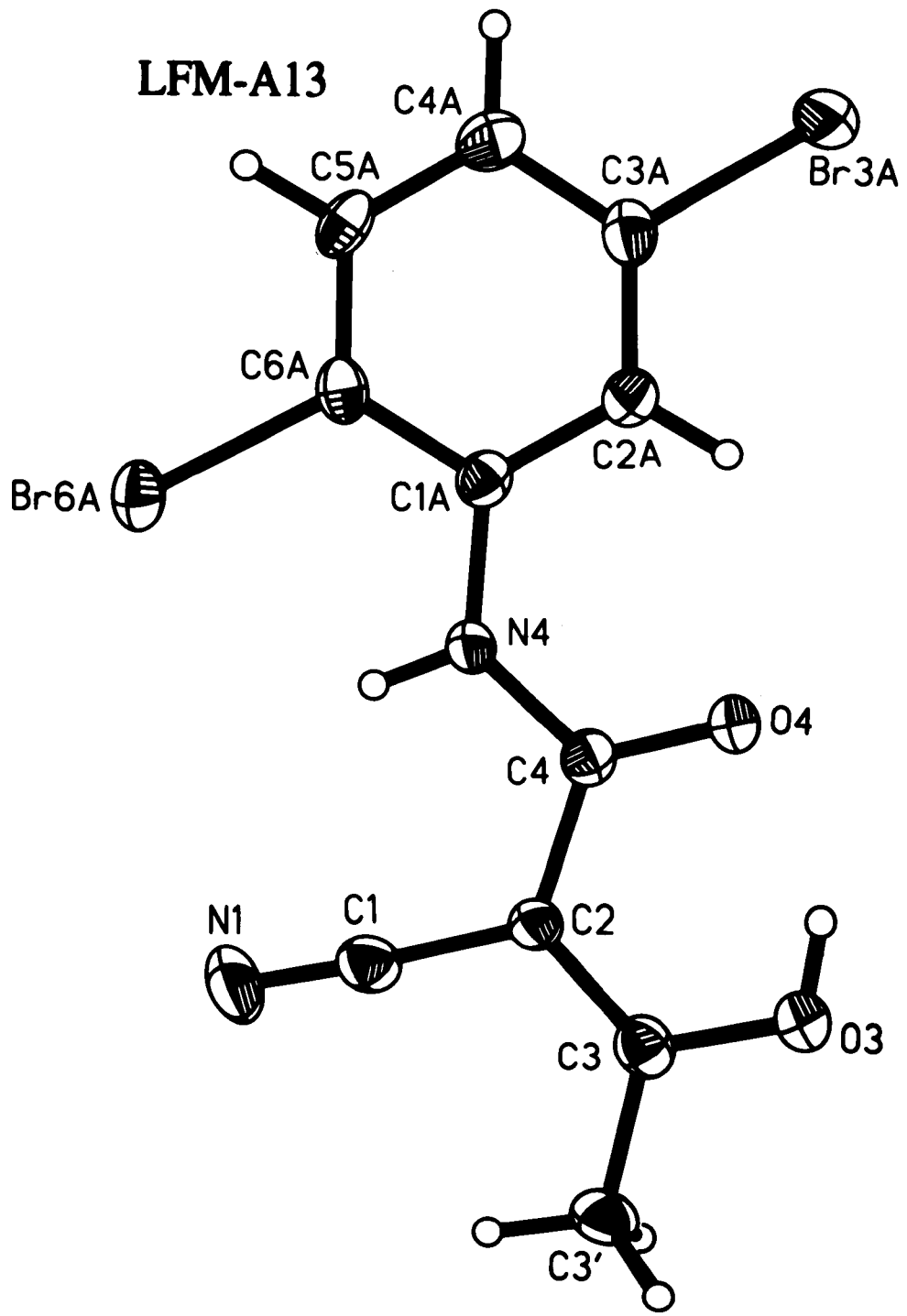
FIG. 13: ORTEP picture of the crystal structure of the BTK inhibitor, LFM-A13.

FIG. 13 shows an ORTEP representation of the compound LFM-A13. The crystal structure of LFM-A13 showed that its molecular conformation was very similar to the energy-minimized molecular coordinates which were generated and used for docking studies with BTK. This conformational similarity with the crystal structures indicated that the molecular models used for docking were appropriate for modeling studies.

Specific Inhibition of BTK by LFM-A13

Cell-free immune complex kinase assays were used to compare the effects of LFM and 12 LFM analogs on the enzymatic activity of human BTK immunoprecipitated from B18-2 cells (Uckun, F. M., et al. (1996) Science 22, 1096–1100) (i.e., BTK-deficient DT-40 chicken lymphoma B-cells reconstituted with wild-type human BTK gene). As shown in Table 1, only LFM-A13 exhibited significant BTK inhibitory activity with an $IC_{50}$ value of 6.2±0.3 μg/ml (=17.2±0.8 μM). None of the other compounds inhibited BTK even at concentrations as high as 100 μg/ml (i.e., at a range of 349 μM for LFM-A12 to 495 μM for LFM-A14).

Figure 14A:
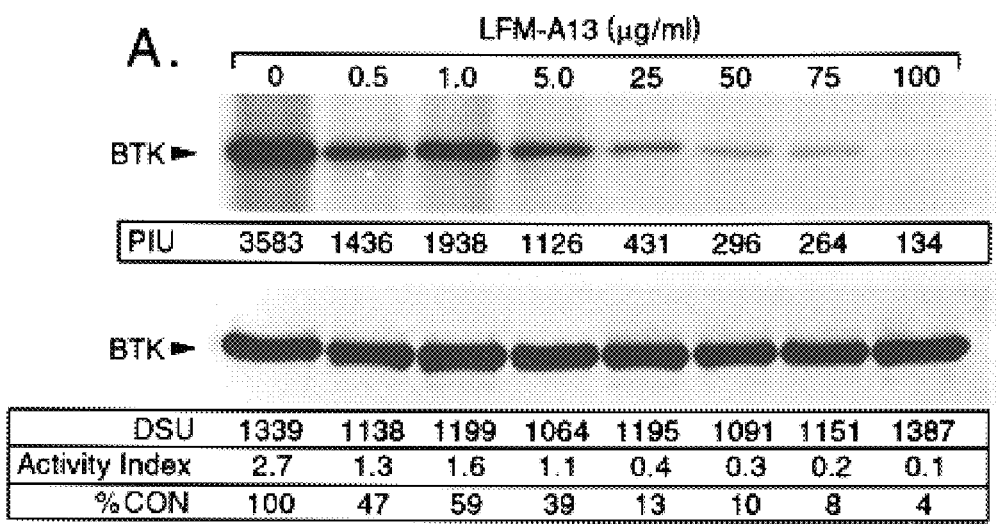
FIGS. 14A–14C: Effects of LFM-A13 on the Tyrosine Kinase Activity of BTK. A highly purified (>90%) preparation of BTK produced in a baculovirus vector expression system was treated for 1 hour at room temperature with LFM-A13 at the indicated concentrations. The enzymatic activity of BTK shown in FIG. 14A was determined by measuring autophosphorylation in a 10 minute kinase assay, as described in the Examples. BTK was irnmunoprecipitated from B18.2 cells (i.e., BTK-DT-40 cells reconstituted with wild-type human BTK), treated with LFM-A13 or vehicle (0.1% DMSO in PBS) for 1 hour, and then assayed for PTK activity, measured by autophosphorylation as well as phosphorylation of GST-Iga, which was used an exogenous kinase substrate. The kinase data is shown in FIG. 14B. B18.2 lymphoma B-cells were treated with LFM-A13, then lysed, and BTK immune complex kinase assays and Western blots were performed as described in the Examples. The data are shown in FIG. 14C. PIU: Phosphoimager units; DSU, densitometric scanning units; CON, control.
Figure 14B:
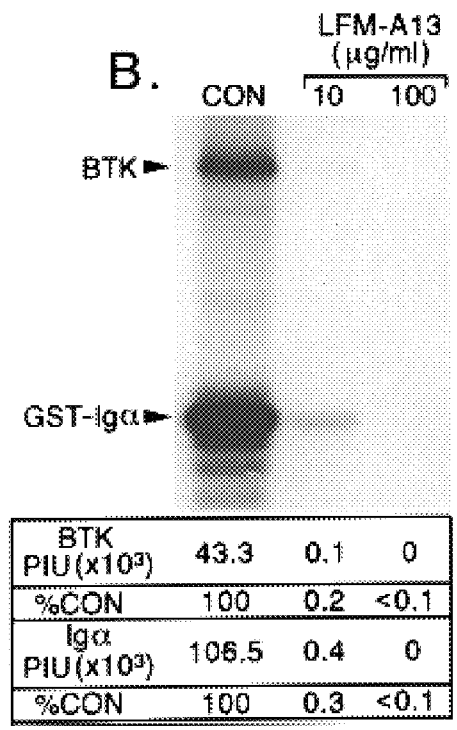
Figure 14C:
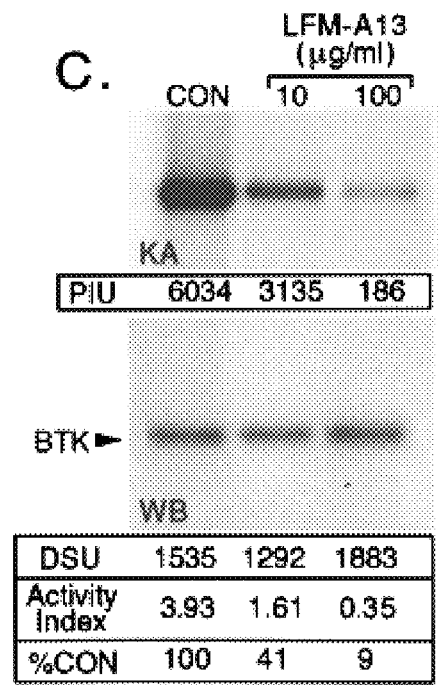
Figure 15:
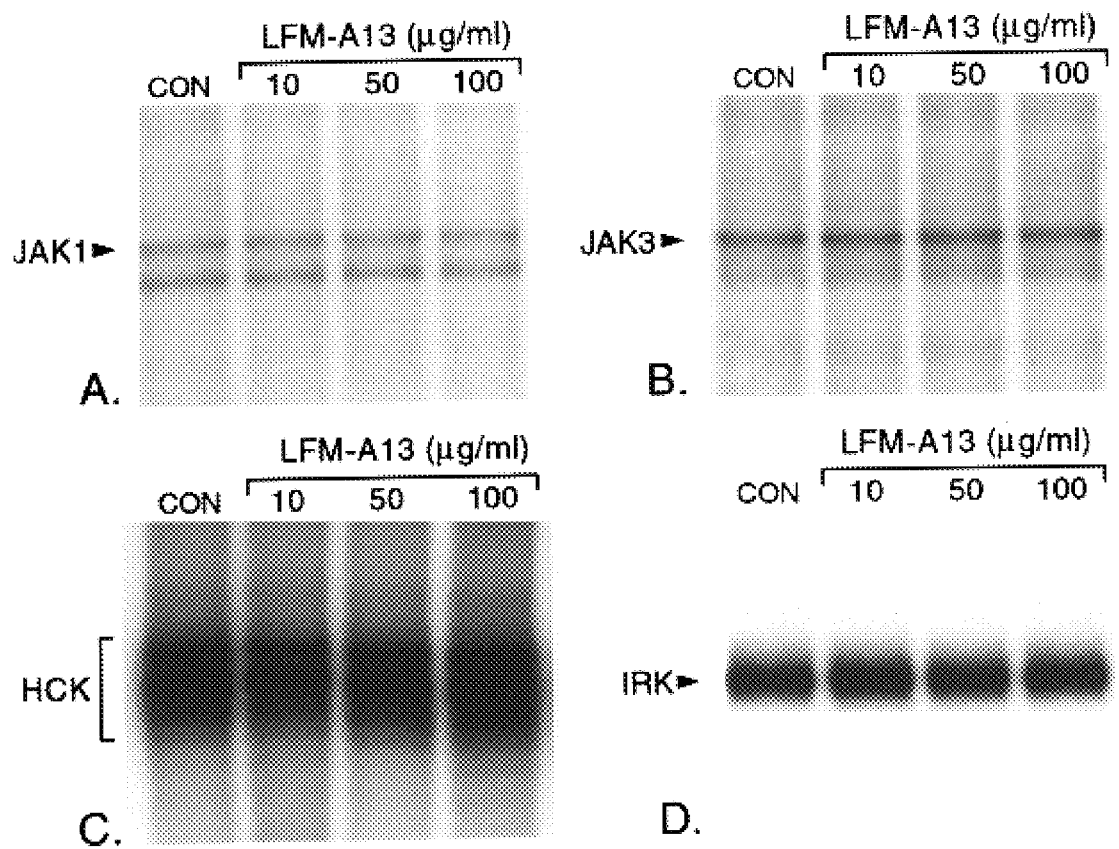
FIG. 15: Effects of LFM-A13 on the Tyrosine Kinase Activity of JAK1, JAK3, HCK, and IRK. JAK1 and JAK3 immunoprecipitated from Sf21 insect ovary cells transfected with the appropriate baculovirus expression vectors, HCK immunoprecipitated from COS-7 cells transfected with the pSV7c-HCK plasmid, and IRK immunoprecipitated from HepG2 hepatoma cells were treated with LFM-A13, then subjected to in vitro kinase assays as described in Experimental Procedures.

LFM-A13 was also effective against recombinant BTK expressed in a baculovirus vector expression system with an $IC_{50}$ value of 0.9 μg/ml (2.5 μM, FIG. 14A), as well as BTK immunoprecipitated from NALM-6 human B-lineage ALL cell lysates (FIG. 14B). Furthermore, treatment of B18.2 cells (FIG. 14C) or NALM-6 cells (data not shown) with LFM-A13 resulted in a dose-dependent inhibition of cellular BTK activity. The inhibitory activity of LFM-A13 against BTK was specific since it did not affect the enzymatic activity of other protein tyrosine kinases, including Janus kinases JAK1 and JAK2, Src family kinase HCK, and receptor family tyrosine kinase IRK, at concentrations as high as 100 μg/ml (~278 μM; Table 3, FIG. 15).

Structural Basis for the BTK-Specificity of LFM-A13.

Biological assays have shown LFM-A13 to be a selective inhibitor of BTK, whereas it is a poor inhibitor of EGFR, HCK, JAK1, JAK3 and IRK. To evaluate this selectivity we constructed a homology model of EGFR, JAK1 and JAK3 using homologous crystal structure coordinates of protein kinases IRK, HCK, and cAPK as a template. The models were then used to study the binding of small molecules such as LFM-A13 into the catalytic sites of these kinases, and to better understand how LFM-A13 can inhibit BTK but not EGFR, IRK, JAK1, JAK3 or HCK. These studies identified three factors which may contribute to the specificity of LFM-A13 for BTK.

The small molecule LFM-A13 was docked into the kinase domains of IRK, HCK, JAK3 and EGFR. Table 3 shows the interaction scores, calculated $K_i$ values, and measured $IC_{50}$ data for LFM-A13 with these kinases. We postulate that the selectivity of LFM-A13 for BTK results from favorable interactions with the BTK catalytic site residues which are not present in the other kinases studied. There are some residues in the BTK active site which differ from those of other PTKs. These differences are illustrated in FIG. 16 which shows the backbone of the BTK catalytic site, the residue differences between BTK and other kinases, and the docked positions of LFM-A13 in the kinase domains of BTK, HCK, JAK3, JAK1, EGFR, and IRK.

Figure 16:
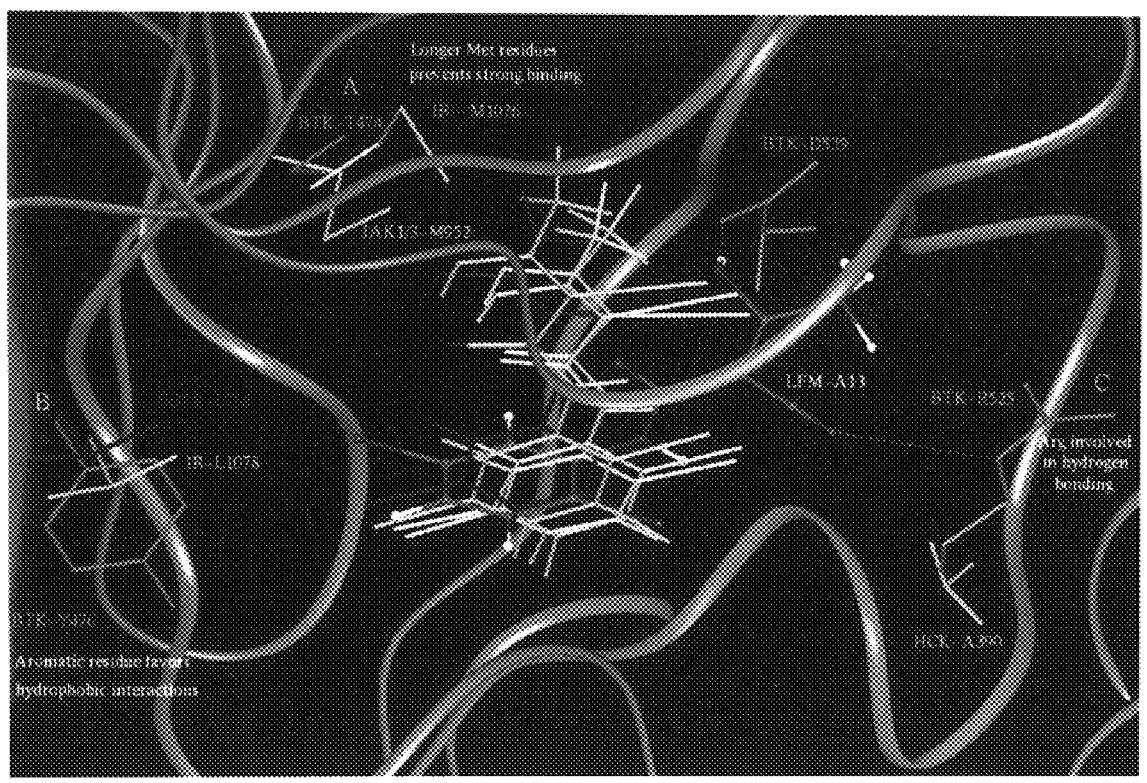
FIG. 16: Structural Basis for the Selectivity of LFM-A13 for BTK. Shown in light blue is a trace of the BTK homology model with selected residues at positions A, B, and C, together with the docked position of the leflunomide metabolite analog LFM-A13 (multicolor). Shown in red is the docked position of LFM-A13 with a model of EGFR and the residue difference between EGFR and BTK at position B. Shown in yellow is the docked position of LFM-A13 with the crystal structure of HCK and the residue difference between HCK and BTK at position C. Shown in pink is the docked position of LFM-A13 with models of JAK3/JAK1 and the residue difference between JAK3/JAK1 and BTK at position A. Shown in dark blue is the docked position of LFM-A13 with the crystal structure of IRK and the residue differences between IRK and BTK at positions A and B.

It is believed that the residue differences shown at positions A, B, and C in FIG. 16 may contribute to the specificity of LFM-A13 for BTK. Kinases that are not inhibited by LFM-A13, such as IRK (gray) and JAK1/JAK3 (pink) contain a methionine residue at position A which protrudes into the active site and prevents the close contact of small molecules like LFM-A13 with the hinge region of the binding site. As a result, LFM-A13 can lose favorable hydrophobic contact with the hinge region of the kinase domains of these proteins and does not bind to it tightly. Moreover, docking studies indicated that the favorable position of LFM-A13 in the BTK kinase domain is such that the side chain of the small molecule is located between residues Asp$^{539}$ and Arg$^{525}$, and forms hydrogen bonds with them.

In addition, an aromatic residue at position B of BTK increases the hydrophobic interaction of the LFM-A13 molecule with the receptor, an interaction which is lost in EGFR (red, FIG. 16) and IRK (dark blue, FIG. 16). This is reflected by the lipophilic (hydrophobic interaction) scores shown in Table 3. While the Lipo scores ranged between 457 and 473 for other kinases, the Lipo score for BTK was higher (more favorable) at 517. Finally, the Arg$^{525}$ residue at position C of BTK can hydrogen bond to LFM-A13. This interaction is lost in HCK (yellow), which contains an Ala at the C position. The favorable position of LFM-A13 at the HCK kinase domain (shown in yellow) is such that the small molecule is aligned along the hinge region. At this position LFM-A13 does not form hydrogen bonds with HCK, which is not the case for BTK. The longer side chain of Arg$^{525}$ in BTK (position C) is involved in hydrogen bonding with LFM-A13, whereas HCK has an Ala at this position which is not able to form the same hydrogen bond.

Figure 18A:
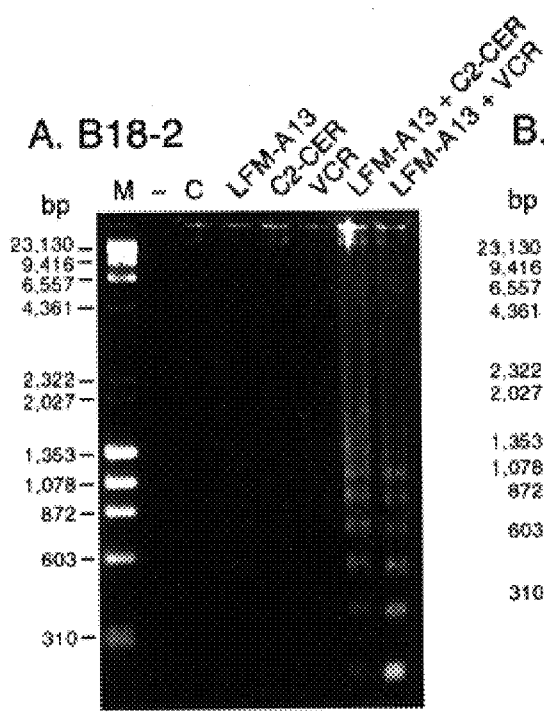
FIGS. 18A–18C: Chemosensitizing Effects of LFM-A13. BTK-deficient DT-40 cells reconstituted with wild-type human BTK gene (i.e., B18.2 clone) (FIG. 18A), NALM-6 human pre-B ALL cells (FIG. 18B), and ALL-1 human Ph+ ALL cells (FIG. 18C) were treated with LFM-A13 (100 $\mu$M), vincristine (VCR) (10 ng/ml), C2-Ceramide (C2-CER) (10 $\mu$M), LFM-A13 (100 $\mu$M)+VCR (10 ng/ml), LFM-A13 (100 $\mu$M)+C2-CER (10 $\mu$M) for 24 hours at 37° C. DNA from Triton-X-100 lysates was analyzed for fragmentation, as described by Uckun, F. M., et al. (1996) Science 22, 1096–1100.
Figure 18B:
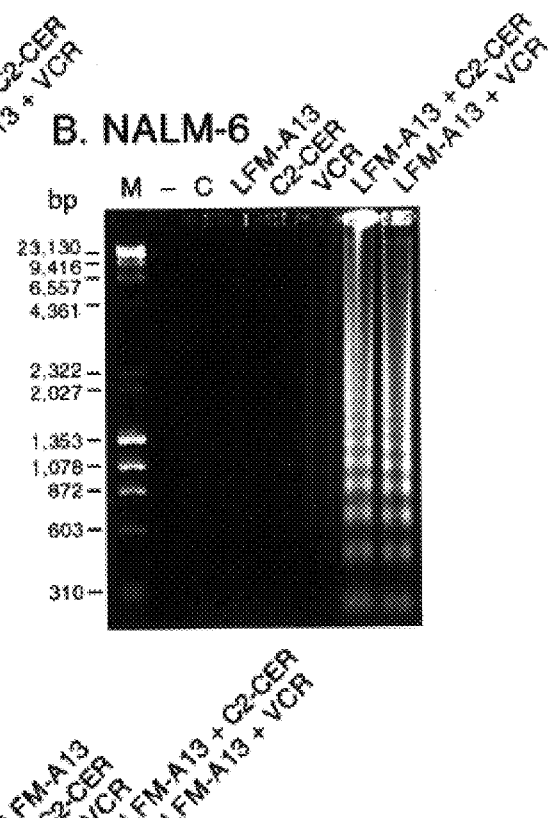
Figure 18C:
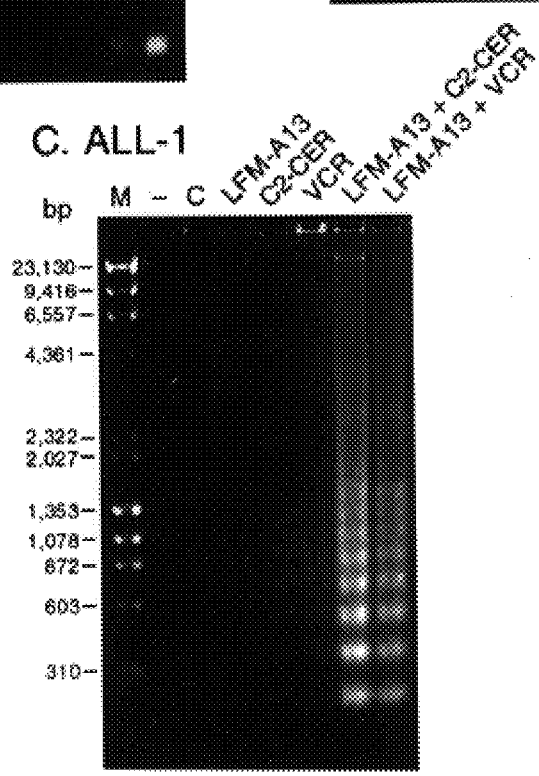

LFM-A13 Enhances the Sensitivity of B-lineage Acute Lymphoblastic Leukemia (ALL) Cells to Ceramide- and Vincristine-Induced Apoptosis Patients with Philadelphia Chromosome (Ph+) ALL have a dismal outcome after intensive multimodality treatment programs. The treatment failure of these patients could be overcome if the apoptotic threshold of their leukemic cells could be decreased. We set out to determine if LFM-A13, by means of inhibiting the anti-apoptotic tyrosine kinase BTK, could alter the sensitivity of the Ph+ ALL cell line ALL-1 to C2-ceramide. As shown in FIG. 17, treatment with LFM-A13 significantly enhanced the chemosensitivity of ALL-1 cells to ceramide-induced apoptosis, as evidenced by a greater percentage of cells treated with LFM-A13 plus C2-ceramide, as compared to cells treated with C2-ceramide alone or LFM-A13 alone, showing dual PI/MC540 fluorescence (shown in blue color) consistent with advanced stage apoptosis. Furthermore, on agarose gels, DNA from Triton-X-100 lysates of B18.2 chicken lymphoma B cells (i.e., BTK-deficient DT40 cells reconstituted with wild-type human BTK gene; see also FIG. 9), NALM-6 human pre-B ALL cells, and ALL-1 cells showed a ladder-like fragmentation pattern consistent with apoptosis after treatment with LFM-A13 plus ceramide or LFM-A13 plus vincristine, which was more pronounced than after treatment with LFM-A13, ceramide, or vincristine alone (FIG. 18). These results demonstrated that LFM-A13 enhances the sensitivity of B-lineage leukemia/lymphoma cells to both ceramide-induced and vincristine-induced apoptosis.

Example 4

Modifications on DDE LFM-A13 for BTK Inhibition

The following example describes how the above homology model and information relating to differences between the binding domain of BTK and other protein tyrosine kinases was used to identify additional compounds of formula I that are specific BTK inhibitors.

Structural and chemical features of LFM analogs which are proposed to aid bindign to the BTK catalytic site are described below and illustrated in FIGS. 20A–20C. Binding Mode 1, (FIGS. 20A–20B) shows the most likely mode of binding of the lead compound LFM-A13 at the BTK catalytic site. Based on the modifications of the lead compound, a second mode of binding may also be possible, illustrated in FIG. 20C (Binding Mode 2).

Table 3 shows the residue differences that the ATP binding site between the ten PTK's: EGFR, Btk, Hck, Jak1, Jak3, IR, FGFR1, PDGFRβ, VEGFR2 and Src.

| No. | EGFR | Btk | Jak1 | Jak3 | IR | Hck | FGFR1 | PDGFRβ | VEGFR2 | Src |
|---|---|---|---|---|---|---|---|---|---|---|
| 1 | Cys | Val 458 | Val | Val | Val | Val | Ile | Val | Val | Val |
| 2 | Leu | Il3 472 | Leu | Leu | Val | Ile | Val | Ile | Val | Ile |
| 3 | Thr | Thr 474 | Met | Met | Met | Thr | Val | Thr | Val | Thr |
| 4 | Leu | Tyr 476 | Phe | Tyr | Leu | Phe | Tyr | Tyr | Phe | Tyr |
| 5 | Cys | Cys 481 | Ser | Cys | Asp | Ser | | | | |
| 6 | Arg | Arg 525 | Arg | Arg | Arg | Ala | | | | |
| 7 | Thr | Ser 538 | Gly | Ala | Gly | Ala | Ala | Cys | Cys | Ala |

Comparison of the inhibitor binding pocket of BTK with that of EGFR, Hck, Jak1, Jak3, IR, FGFR1, PDGFRβ, VEGFR2, and Src shows that SER 538 in the ATP binding cleft of BTK is unique (Table 3), and a target for specific BTK inhibitors design. Ligands designed to interact with this residue should have increased specificity for BTK. FIG. 20B shows the distances (in angstroms) of the NH, =O, and OH groups of the docked LFM-13 ligand from SER 538. When looking into the BTK binding cleft with the aromatic ring of the ligand facing out and the chain going inward, this residue is located below the ligand. Non-planar, single chain substitutions ending with O or N and having the appropriate lengths (FIG. 20B) at the NH, =O, and OH groups should allow the formation of hydrogen bonds with Ser 538. Based on this observation and on modeling and biological data for the 13 leflunomide metabolite analogs described above, additional compounds of formula I can be designed to better interact with the binding pocket that are expected to be inhibitors of BTK.

Example 5

Second Generation LFM Analogs

The following example describes how novel compounds of formula I designed to target SER 538 are designed and prepared.

Figure 20B:
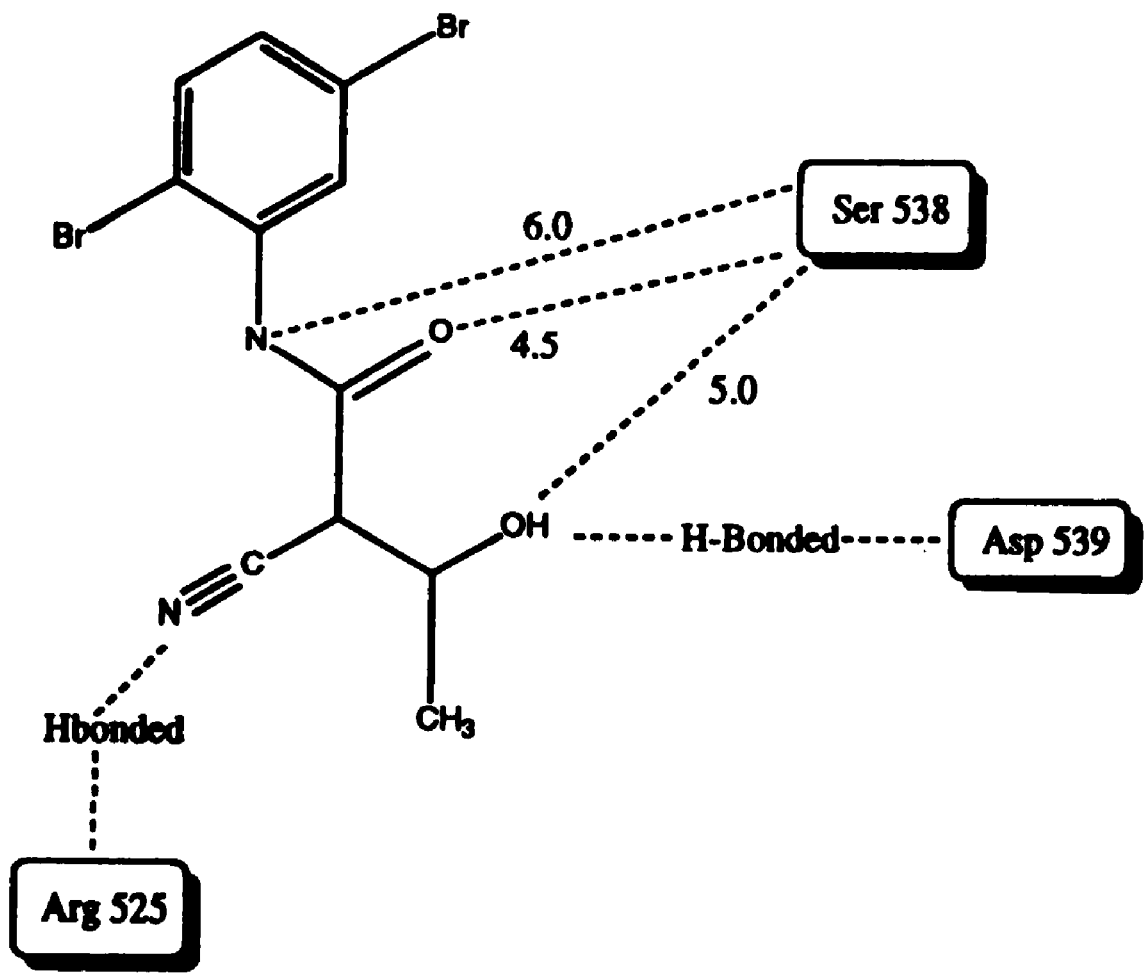
Figure 22C:
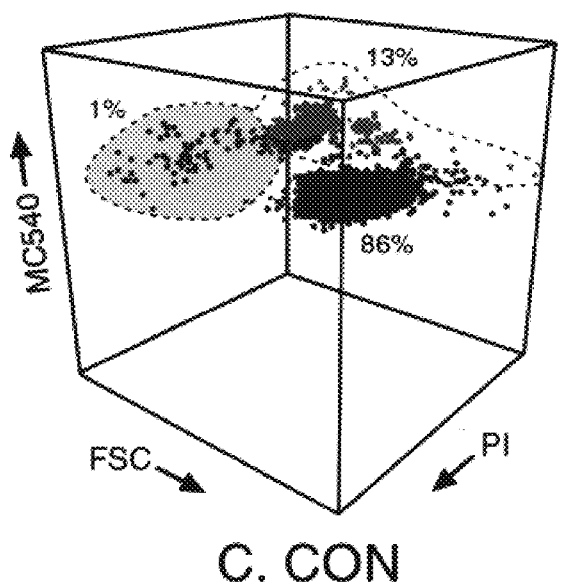
Figure 22D:
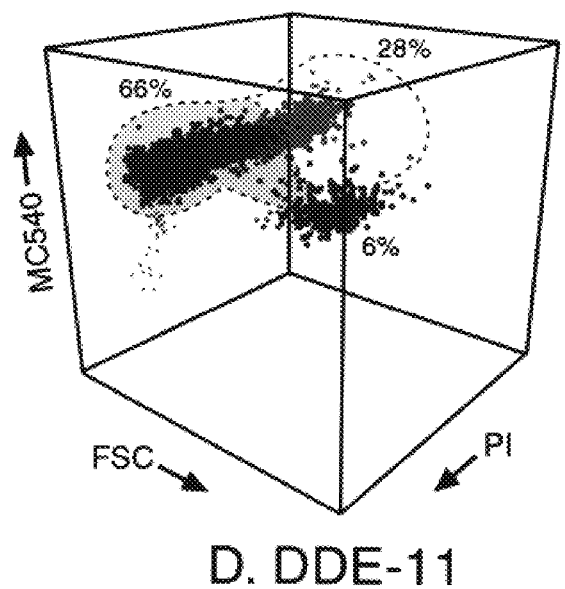

Using the design parameters described in FIGS. 20A–20B, a second generation of LFM analogs (LFM-A15–20) were designed and synthesized. The compounds have the following structural formula:

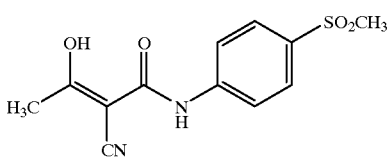
LFM-A15

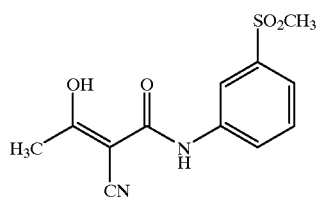
LFM-A16

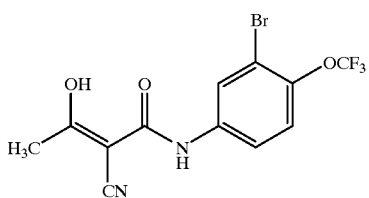
LFM-A17

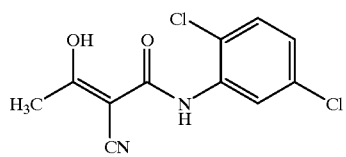
LFM-A18

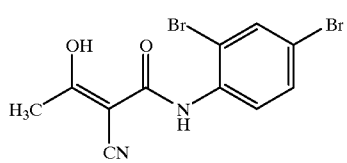
LFM-A19

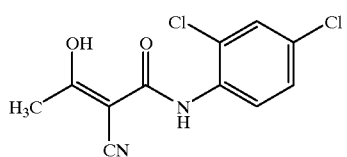
LFM-A20

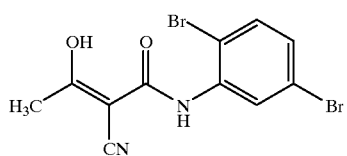
LFM-A13

The following synthetic schemes were used to generate the compounds:

Scheme

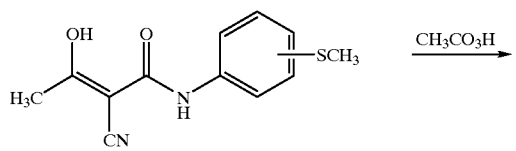

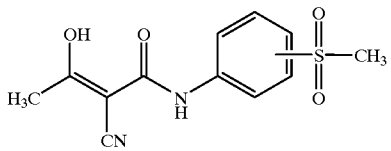

Synthetic Procedure A. 1,3-diisopropylcarbodiimide (1.75 g; 13.9 nunol) was added to a solution of cyanoacetic acid 1 (1.70 g; 20.0 mmol) and the desired substituted -aniline 2 (12.6 mmol) in tetrahydrofuran (25 mL) at 0° C. The mixture was stirred for 12 hours at room temperature. The urea precipitate (reaction side product) was removed by filtration and partitioned between ethyl acetate and 0.5 N HCl. The organic layer was sequentially washed with brine twice, dried over anhydrous $Na_2SO_4$ and concentrated by rotary-evaporation. Finally, the crude solid product was recrystallized from ethyl alcohol to give pure 3. Sodium hydride (0.93 g; 60% in mineral oil; 23.2 mmol) was added slowly to the solution of 3 (12.0 mmol) in tetrahydrofuran (40 mL) at 0° C. After stirring for 30 minutes at 0° C., acetyl chloride (1.04 g; 13.2 mmol) was added to the reaction mixture. The reaction was continued for another hour and then was quenched by the addition of acetic acid (2 mL). The mixture was poured into ice water (100 mL) containing 2.5 mL of hydrochloric acid to precipitate the crude product, which was collected by filtration and washed with water. The pure product was obtained by recrystallization.

Synthetic Procedure B. α-Cyano-β-hydroxypmethyl-N-[(methylthio)phenyl]propenamide (2.48 g, 10.0 mmoll was dissolved in acetic acid (I150 mL), and peracetic acid (8.6 mL of 32% wt solution in acetic acid) was added. The mixture was stirred overnight at room temperature, and water (75 mL) was added. The precipitate was filtered and washed with water. The pure product was obtained by recrystallization.

Physical Data for Synthesized Compounds:

α-Cyano-β-hydroxy-β-methyl-N-[4-(methylsulfonyl)phenyl]propenamide. Melting point: 205–206° C. $^1$H NMR (DMSO-$d_6$): δ 11.26 (s, 1H, NH), 7.81 (d, J=9.0 Hz, 2H, ArH), 7.76 (d, 9.0 Hz, 2H, ArH), 3.15 (s, 3H, $SO_2CH_3$), 2.19 (s, 3H, $CH_3$). IR (KBr): 3309, 2225, 1643 and 1586 cm$^{-1}$. MS (EI): m/z 281.0 (M+H$^+$), 172.1.

α-Cyano-β-hydroxy-β-methyl-N-[3-(methylsulfonyl)phenyl]propenamide. Melting point: 213–214° C. $^1$H NMR (DMSO-$d_6$): δ 10.98 (s, 1H, NH), 8.18 (m, 1H, ArH), 7.82 (m, 1H, ArH), 7.60 (m, 2H, ArH), 3.18 (s, 3H, $SO_2CH_3$). IR (KBr): 3278, 2231, 1607 and 1555 cm$^{-1}$. MS (EI): m/z 281.0 (M+H$^{+1}$), 172.1.

α-Cyano-β-hydroxy-β-methyl-N-[3-bromo,4-(trifluoromethoxy)phenyl]-propenamide. Melting point: 178–179° C. $^1$H NMR (DMSO-$d_6$): δ 11.03 (s, 1H, NH), 8.12 (d, J=2.4 Hz, 1H, ArH), 7.55 (dd, J=2.4, 9.0 Hz, 1H, ArH), 7.45 (m, 1H, ArH), 5.53 (s br, 1H, OH), 2.20 (s, 3H, $CH_3$). IR (KBr): 3304, 2350, 1620 and 1602 cm$^{-1}$. MS (ED: m/z 365.0 (M+H$^+$), 255.9.

α-Cyano-β-hydroxy-β-methyl-N-(2,4-dibromophenyl)propenamide. Melting point: 181–182° C. $^1$H NMR (DMSO-$d_6$): δ 11.03 (s, 1H, NH), 8.14 (m, 1H, ArH), 7.84 (d, J=2.4 Hz, 1H, ArH), 7.51 dd, J=2.4, 9.0 Hz, 1H, ArH), 5.65 (s br, 1H, OH), 2.20 (s, 3H, $CH_3$). IR (KBr): 3360, 2205, 1591 and 1530 cm$^{-1}$. MS (EI): m/z 361.0 (M+H$^+$), 249.9.

α-Cyano-β-hydroxy-β-methyl-N-(2,4-dichlorophenyl)propenamide. Melting point: 143–144° C. $^1$H NMR (DMSO-d$_6$): δ 11.23 (s, 1H, NH), 8.29 (m, 1H, ArH), 7.60 (d, J=2.4 Hz, 1H, ArH), 7.35 (dd, J=2.4, 9.0 Hz, 1H, ArH), 5.17 (s br, 1OH), 2.18 (s, 3H, CH$_3$). IR (KBr): 3371, 2210, 1601 and 1540 cm$^{-1}$. MS (EI): m/z 271.0 (M$^+$), 162.0.

α-Cyano-β-hydroxy-β-methyl-N-(2,5-dichlorophenyl) propenamide. Melting point: 143–144° C. $^1$H NMR (DMSO-d$_6$): δ 11.70 (s, 1H, NH), 8.51 (d, J=3.0 Hz, 1H, ArH), 7.45 (d, J=8.7 Hz, ArH), 7.05 (dd, J=3.0, 8.7 Hz, 1H, OH), 2.14 (s, 3H, CH$_3$). IR (KBr): 3402, 2205, 1627 and 1606 cm$^{-1}$. MS (EI): m/z 271 (M$^+$), 162.0.

TABLE 4

Interaction scores, estimated K$_i$ values and measured IC$_{50}$ data for LFM analogs with BTK

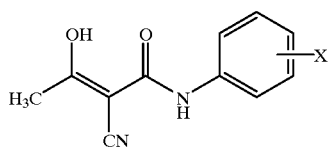

| Compound | X | F.W. | M.S.$^a$ (Å$^2$) | BTK Inhibition IC$_{50}$ (μM) |
|---|---|---|---|---|
| LFM-A15 | 4-SO$_2$CH$_3$ | 280.30 | 261.7 | 35.7 μM |
| LFM-A16 | 3-SO$_2$CH$_3$ | 280.30 | 259.3 | 35.7 μM |
| LFM-A17 | 4-OCF$_3$, 3-Br | 365.11 | 265.6 | 20.5 μM |
| LFM-A18 | 2,5 diCl | 271.10 | 231.6 | 3.7 μM |
| LFM-A19 | 2,4 diBr | 360.00 | 227.2 | 2.8 μM |
| LFM-A20 | 2,4 diCl | 271.10 | 230 | 37.0 μM |

$^a$M.S., molecular surface area calculated using Connolly's MS program. Defined as boundary of volume within any probe sphere (meant to represent a water molecule) of given radius sharing no volume with hard sphere atoms which make up the molecule.

The second generation LFM analogs were evaluated for ineraction with the BTK binding pocket model, and evaluated for inhibitory activity against BTK as described in the Examnple above. The data are shown in Table 4, and demonstrate these novel compounds to be patent inhibitors of BTK.

Using the following synthetic scheme, compounds of formnula II can be prepared from readily available starting materials.

Example 6

Benzopyram Derivatives as BTK Inhibitors

Representative compounds of formula II described hereinabove have been designed as BTK inhibitors. In particular, the compound of formula II wherein R$_6$ is propyl; R$_7$ is hydrogen; R$_8$ is oxo; and R$_9$ is propanoyl (Compound "DDE11") has been found to be a potent and selective inhibitor of BTK.

The homology model of the BTK binding site was used to identify analogs of DDE11. Based on the analysis of the binding of DDE11 to BTK, compounds of formula II were designed, synthesized, and identified as inhibitors of BTK. The structures of compounds of formula II that were synthesized and analyzed for BTK inhibiting activity are shown below:

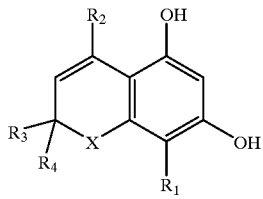

X = O, N, S,

R$_1$ = alkyl, carbonyl, (C$_1$–C$_3$) alkyl with or without substituents (C$_1$–C$_3$) alkyl with or without substituents.

R$_2$ = alkyl, perferably (C$_1$–C$_6$) alkyl

R$_3$ and R$_4$ can be substituents selected from hydrogen, halo, —OH, —SH, amino, nitro, cyano, (C$_1$–C$_6$) alkoxy, (C$_1$–C$_6$)alkanoyl, (C$_1$–C$_6$)alkanoyloxy, amide, carboxy or ster.

R$_3$ and R$_4$ together can be carbonyl or thiocarbonyl.

DDE181

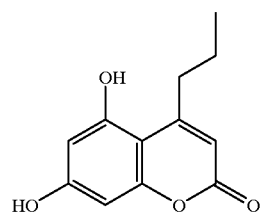

DDE229

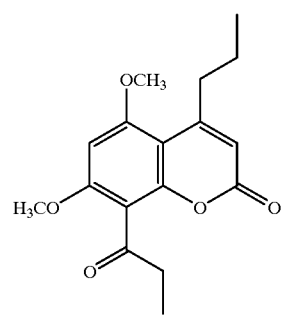

DDE271

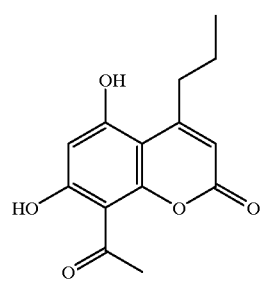

DDE355

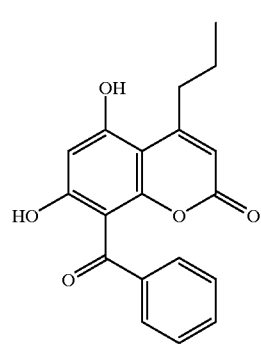

-continued

DDE11
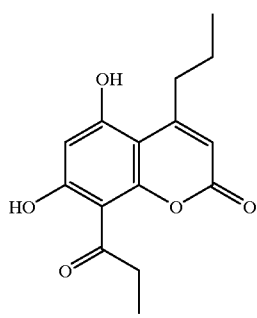

DDE264
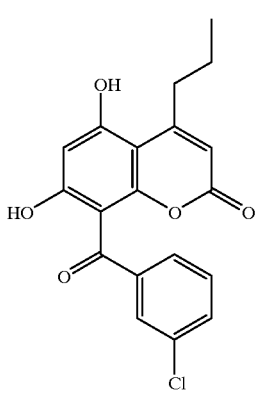

DDE272
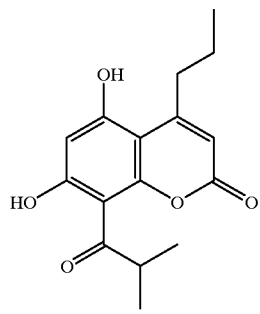

DDE213
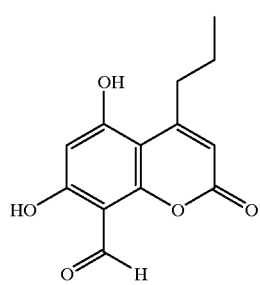

DDE270
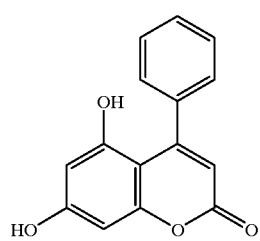

-continued

DDE305
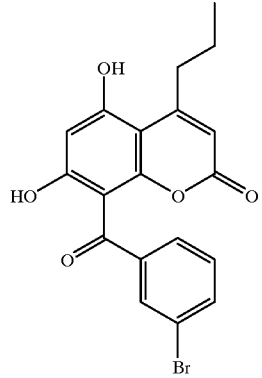

DDE214
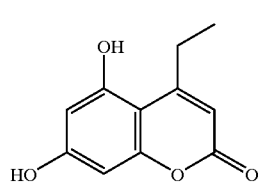

Reaction of phloroglucinol with the requsite P-ketoester under acid catalysis yields a bicyclic analog, which can be acylated with an acid chloride (or anhydride) under Friedel-Crafts conditions to give a compound of formula II.

Using this general procedure, a series of compounds of formula II were prepared and tested for BTK inhibitory activity using the methods described above. The results are shown in Table 5.

TABLE 5

Structure of Benzopyran Derivatives.

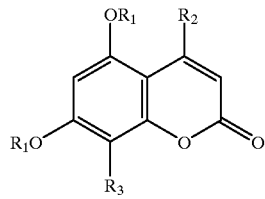

| Compounds | $R_1$ | $R_2$ | $R_3$ | $IC_{50}$ mcg/mL |
|---|---|---|---|---|
| DDE181 | H | $CH_2CH_2CH_3$ | H | <10 |
| DDE11 | H | $CH_2CH_2CH_3$ | $COCH_2CH_3$ | <10 |
| DDE213 | H | $CH_2CH_2CH_3$ | COH | <10 |
| DDE214 | H | $CH_2CH_3$ | H | <10 |
| DDE229 | $CH_3$ | $CH_2CH_2CH_3$ | $COCH_2CH_3$ | >100 |
| DDE264 | H | $CH_2CH_2CH_3$ | $COC_6H_4Cl$ | >75 |
| DDE270 | H | $C_6H_5$ | H | 25 |
| DDE271 | H | $CH_2CH_2CH_3$ | $COCH_3$ | >100 |
| DDE272 | H | $CH_2CH_2CH_3$ | $COCH(CH_3)_2$ | >100 |
| DDE305 | H | $CH_2CH_2CH_3$ | $COC_6H_4Br$ | >75 |
| DDE355 | H | $CH_2CH_2CH_3$ | $COC_6H_5$ | >100 |

5,7-Dihydroxy-4 propyl-2H-1-benzopyran-2-one (DDE 181) was prepared according to the literature procedure (Chenera et al., *J. Org. Chem.*, 1993, 58, 5605–5606) A suspension of anhydrous phloroglucinol (20.0 g, 159 mmol) in ethyl butyryl acetate (26.3 g, 167 mmol) was added to mechanically stirred trifluoromethanesulfonic acid (50 g) cooled in an ice bath. The addition over 30 minutes resulted in the formation of a yellow paste which was stirred for 16 hours. The reaction was quenched by the careful addition of water and ice and the solid material was filtered and dried. Analytically pure 5,7-dihydroxy-4 propyl-coumarin was obtained by recrystallization in 95% ethanol (30.1 g, 81.9%): $^1$H NMR (DMSO-d$_6$) 0.95 (t, 3H), 1.59 (m, 2H), 2.85 (t, 2H), 5.84 (s, 1H), 6.29 (d, 1H) 10.32 (s, 1H), 10.60 (s, 1H); GC/MS 220 (M*), 205, 192, 177, 164; IR (KBr) 3218, 1666, 1616 CM$^{-1}$.

5,7-Dihydroxy-8-propanoyl-4-propyl-2H-1-benzopyran-2-one (DDE 11). To a mixture of 5,7-dihydroxy-4propyl-coumarin (10 g, 45 mmol) and anhydrous AlCl$_3$ (12 g, 90 mmol) was added 1,2-dicholoroethane (120 mL). The resulting suspension was heated to 75° C. with vigorous stirring. After 30 minutes of stirring a brown slurry was obtained, then nitrobenzene was introduced into the mixture resulting in an orange colored solution. A solution of anhydrous AlCl$_3$ (12 g, 90 mmol) and propionic anhydride (6.6 g. 45 mmol) in 1,2-dichloroethane (60 mL) was added dropwise over a period of 1–2 hours. After addition, the mixture was allowed to stir at 75° C. for another two hours and subsequently cooled to room temperature. The resulting mixture was poured into ice and 1N HCl. The precipitated product was filtered and then taken into ethyl acetate and the aqueous solution was extracted throughly with additional ethyl acetate (3×300 mL). The combined ethyl acetate extracts were dried over Na$_2$SO$_4$ and the solvent was removed under reduced pressure. The resulting solid was purified by column chromatography (1:1 Hexane/ethyl acetate) yielding 5,7-dihydroxy-8-propionyl-4 propyl-coumarin (4.2 g, 24%): 240–245° C.; $^1$H NMR (DMSO-d$_6$)δ 0.93 (t, 3H), 1.57 (sextet 2H), 2.86 (t, 2H), 2.98 (q, 2H), 5.96 (s, 1H) 6.20 (s, 1H), 11.44 (s, 1H), 12.47 (s, 1H): GC/MS 294, 277, 276, 247; IR (KBr) 3249, 1693, 1625 and 1592 cm$^{-1}$; UV$_{max}$(MeOH) 219,288,319 nm.

5,7-Dihydroxy-8-carboxaldehyde-4-propyl-2H-1-benzopyran-2-one (DDE 213) was prepared according to the method of Deesphante et al.(14) To a solution 5,7-dihydroxy-4-propyl-coumarin (1.00 g, 5.59 mmol) in dicholoroethane (60 mL) was added N-methylformanilide (1.23 g, 9.10 mmol) and POCl$_3$ (0.77 g, 0.50 mmol). The reaction mixture was stirred at 75° C. for 4 hours at which time it was allowed to cool to room temperature. The solution was then neutralized by the dropwise addition of a saturated aqueous NaOAc solution. The solid that formed was filtered, dried and recrystallized from MeOH to give a light brown solid (0.60 g, 53%): mp. 225–228° C. (lit. mp. 236–237° C.)(14); $^1$H NMR (DMSO-d$_6$)δ 0.92 (t, 3H), 1.55 (m, 2H), 2.83 (t, 2H), 6.05 (s, 1H), 6.15 (s, 1H), 6.15 (s, 1H), 10.1 (s, 1H), 12.1 (bs, 1H).

5,7-Dihydroxy-4-ethyl-2H-1-benzopyran-2-one (DDE 214). A suspension of phloroglucinol (1.04 g, 8.35 mmol) in ethyl propionyl acetate (1.24 mL, 8.71 mmol) was added over 0.5 h to triflic acid (2 mL). The reaction was mechanically stirred in an ice bath for 16 h. The reaction was quenched by carefully pouring into an ice bath. The solid was filtered and dried yielding a white solid (1.1 g, 83.2%): mp. 248–252° C.; $^1$H NMR (DMSO-filtered and dried yielding a white solid (1.1 g, 83.2%): mp. 248–252° C.; $^1$H NMR (DMSO-d$_6$) δ 1.15 (t, 3H), 2.91 (q, 2H), 5.83 (s, 1H), 6.17 (d, 1H), 6.26 (d, 1H) 10.3 (s, 1H) 10.6 (s, 1H).

5,7-Dihydroxy-8-acetyl-4-propyl-2H-1-benzopyran-2-one (DDE 271). To a mixture of 5,7-dihydroxy-4-propyl-coumarin (2.06 g 9.36 mmol) and anhydrous AlCl$_3$ (2.53 g, 18.7 mmol) was added 1,2-dichloroethane (120 mL). The resulting suspension was heated to 75° C. with vigorous stirring. After 30 minutes of stirring, a brown slurry was obtained, then nitrobenzene was introduced into the mixture resulting in an orange colored solution. A solution of anhydrous AlCl$_3$ (2.53 g, 18.7 mmol) and acetic anhydride (0.88 mL, 9.36 mmol) in 1,2-dichloroethane (40 mL) was added dropwise over a period of 1–2 hours. After addition, the mixture was allowed to stir at 75° C. for another two hours and subsequently cooled to room temperature. The resulting mixture was poured into ice and 1N HCl. The precipitated product was filtered and then taken into ethyl acetate and the aqueous solution was extracted throughly with ethyl acetate (3×100 mL). The combined ethyl acetate extracts were dried over N$^a$$_2$SO$_4$ and the solvent was removed under reduced pressure. The resulting solid was purified by column chromatography (1:1 hexane/ethyl acetate) yielding 5,7-dihydroxy-8-acetyl-4-propyl-coumarin (0.30 g, 12%): mp. 221–224° C.; $^1$H NMR (DMSO-d$_6$) δ 0.94 (t, 3H), 1.58 (sextet, 2H), 2.66 (s, 3H), 2.87 (t, 2H), 6.01 (s, 1H), 6.29 (s, 1H).

5,7-Dihydroxy-4-phenyl-2H-1-benzopyran-2-one (DDE 270). A suspension of phloroglucinol (2.10 g, 12.9 mmol) in ethyl benzoyl acetate (2.41 mL, 13.8 mmol) was added over 0.5 hours to triflic acid (4 mL). The reaction was mechanically stirred in an ice bath for 16 h. The reaction was quenched by carefully pouring into an ice bath. The solid was filtered and dried yielding a yellow solid (2.43 g, 74.8%): mp. 179–182° C.; $^1$H NMR (DMSO-D$_6$) δ 5.75 (s, 1H), 6.15 (s, 1H), 6.25 (s, 1H).

As shown in Table 5, the BTK kinase domain model demonstrated its efficiency in predicting useful BTK inhibitors. These compounds inhibited BTK in kinase assays in a dose-dependent mannet. (See FIG. 21) Particularly, potent BTK inhibitors of formula II, include DDE181, DDE12, DDE213, and DDE214.

These compounds promote apoptosis in some cell types, such as Leukemia cells. Treatment with these compounds alone was sufficient ot trigger apoptosis and cell death, as shown in FIGS. 22A–22D.

Figure 23A:
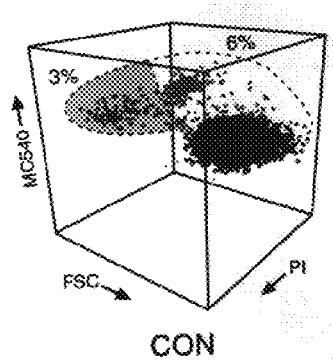
FIG. 23: Effects of DDE-11 on cerarnide or vincristine-sensitivity of human leukemia cells. Studies were done as described above for FIG. 17, but using DDE11 as the BTK inhibitor.
Figure 23B:
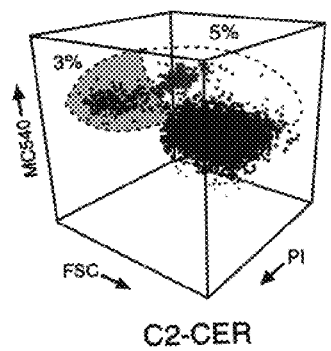
Figure 23C:
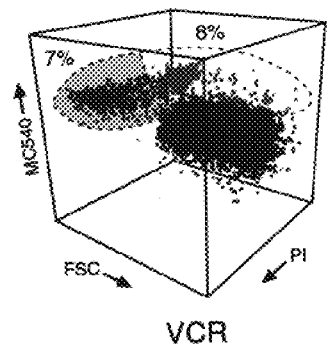

The inhibitors also increase the sensitivity of cells to chemotherapy agents. As shown in FIG. 23, co-administration of DDE-11 with chemotherapeutic agents C2-CER and vincristine (VCR) increaseed the cytotoxicity over the use of the chemotherapeutic agent alone.

Example 7

Novel BTK Inhibitor Designs

Figure 24:
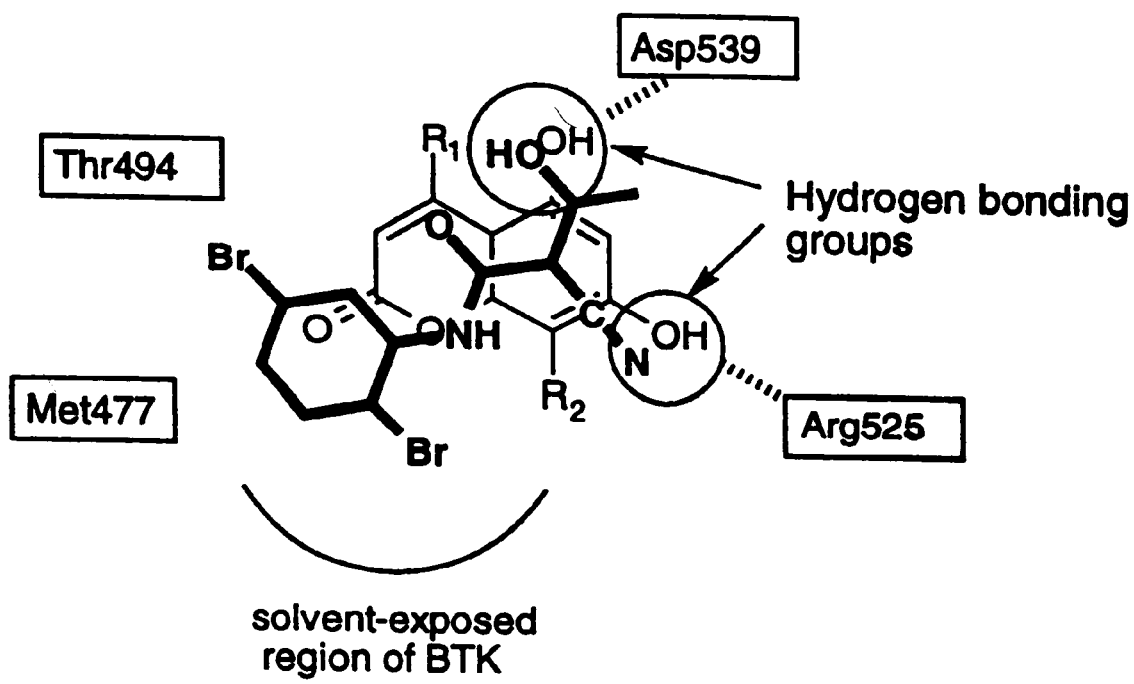
FIG. 24: Binding features of both DDE11 and LFM-A13 based ondocking these compounds in to the ATP-bindign site of BTK. Both compounds contain hydrogen bindign groups that can interact with ASP 525 and Ary 523.
Figure 25B:
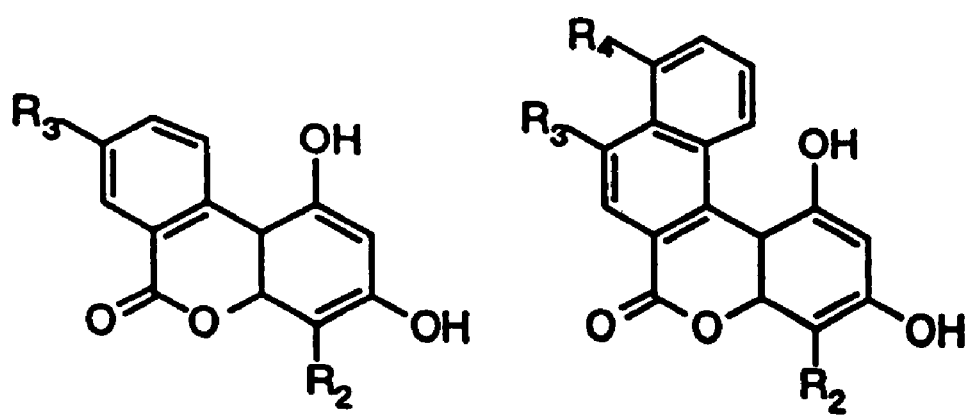

FIG. 24 shows the binding features commron to DDE11 and LFM A13, based on docking the compounds inot the ATP-binding site of BTK. Both inhibitors contain hydrogen-bonding gropus (OH, CN) positioned to interact with Asp 525 and Arg 525. Viewing the binding pocket and target residues as in FIGS. 25A–25B and 26A–26B compound designs that better fill the binding pocket and interact favorably with eligible residues in the pocket are designed, as indicated in FIGS. 25B and 26B.

These compounds, due to their increased volume and groups designed to interact with the binding pocket residue, are expected to have potent BTK-inhibitory activity.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

TABLE 1

Interaction scores, calculated $K_i$ values and measured $IC_{50}$ values for LFM analogs with BTK.

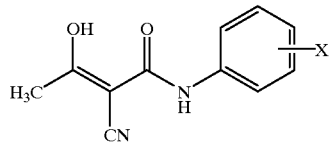

| Compound | X | M.S.[a] (Å$^2$) | B.S.[b] (Å$^2$) | Lipo Score | No. of Hydrogen Bonds | Ludi Score | Ludi[c] $K_i$ (mM) | BTK Inhibition[d] $IC_{50}$ (mM) |
|---|---|---|---|---|---|---|---|---|
| LFM | p-CF$_3$ | 240 | 168 | 491 | 1 | 475 | 56.2 | >370 |
| LFM-A1 | p-Br | 234 | 156 | 459 | 1 | 446 | 36.3 | >356 |
| LFM-A2 | p-Cl | 232 | 162 | 476 | 1 | 461 | 24.5 | >423 |
| LFM-A3 | p-F | 219 | 158 | 462 | 1 | 446 | 34.7 | >454 |
| LFM-A4 | o-CF$_3$ | 237 | 171 | 501 | 1 | 485 | 44.7 | >370 |
| LFM-A5 | o-Br | 228 | 162 | 474 | 1 | 458 | 26.3 | >356 |
| LFM-A6 | o-Cl | 229 | 165 | 483 | 1 | 467 | 21.4 | >423 |
| LFM-A7 | o-F | 218 | 146 | 428 | 1 | 412 | 75.9 | >454 |
| LFM-A8 | m-CF$_3$ | 248 | 172 | 503 | 1 | 488 | 44.7 | >370 |
| LFM-A9 | m-Br | 239 | 167 | 490 | 1 | 474 | 18.2 | >356 |
| LFM-A10 | m-Cl | 233 | 163 | 478 | 1 | 463 | 23.4 | >423 |
| LFM-A11 | m-F | 218 | 153 | 448 | 1 | 432 | 47.9 | >454 |
| LFM-A12 | p-OCF$_3$ | 257 | 170 | 497 | 1 | 457 | 27.0 | >349 |
| LFM-A13 | 2,5-diBr | 248 | 176 | 517 | 2 | 587 | 1.4 | 17.2 ± 0.8 |
| LFM-A14 | H | 212 | 148 | 434 | 1 | 419 | 64.5 | >495 |

[a]M.S., molecular surface area calculated using Connolly's MS programError! Bookmark not defined.. Defined as boundary of volume within any probe sphere (meant to represent a water molecule) of given radius sharing no volume with hard sphere atoms which make up the molecule.
[b]B.S., buried surface: molecular surface in contact with protein calculated by Ludi based on docked positions.
[c]Ludi $K_i$ calculated based on the empirical score function in Ludi program.
[d]Cell-free inhibition assays were performed in 3 independent experiments on BTK immunoprecipitated from B18.2 cells and exposed to LFM and LFM analogs for 1 hr prior to hot kinase assays. Except for LFM-A13 none of the compounds inhibited BTK in any of the experiments even at concentrations as high as 100 μg/ml (349–495 μM).

TABLE 2

Interaction scores, calculated $K_i$ values and measured $IC_{50}$ values for LFM-13 with several different PTKs.

| Tyrosine Kinase | M.S.[a] (Å$^2$) | B.S.[b] (%) | Lipo Score | No. of Hydrogen Bonds | Ludi Score | Ludi[c] $K_i$ (μM) | Inhibition $IC_{50}$ (μM) |
|---|---|---|---|---|---|---|---|
| JAK1 | 250 | 68 | 497 | 0 | 396 | 110 | >278 |
| JAK3 | 246 | 67 | 484 | 0 | 383 | 148 | >278 |
| IRK | 248 | 64 | 466 | 1 | 450 | 31.6 | >278 |
| EGFR | 248 | 66 | 479 | 0 | 378 | 166 | >278 |
| HCK | 246 | 65 | 468 | 0 | 367 | 214 | >278 |

[a]M.S., molecular surface area calculated using Connolly's MS programError! Bookmark not defined.. Defined as boundary of volume within any probe sphere (meant to represent a water molecule) of given radius sharing no volume with hard sphere atoms which make up the molecule.
[b]B.S., buried surface: percentage of molecular surface in contact with protein calculated by Ludi based on docked positions.
[c]Ludi $K_i$ calculated based on the empirical score function in Ludi program.
[d]Cell-free tyrosine kinase inhibition assays were performed in 2–3 independent experiments, as described in the Methods section. LFM-A13 did not inhibit JAK1, JAK3, IRK, EGFR, or HCK in any of the experiments even at concentrations as high as 100 μg/ml (278 μM). The results from a representative experiment are depicted in FIG. 7.

We claim:

1. A method for treating allergy comprising administering to a patient a therapeutically effective amount of a leflunomide analog of formula I:

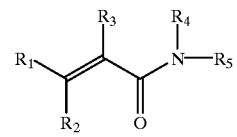

where:
  $R_1$ is $(C_1-C_3)$alkyl, $(C_3-C_6)$cycloalkyl, phenyl, or $NR_aR_b$;
  $R_2$ is hydroxy, $(C_1-C_6)$alkoxy $(C_1-C_6)$alkanoyloxy amino $(C_2-C_5)$alkoxy; hydroxy $(C_2-C_5)$alkoxy amino $(C_2-C_5)$alkanoxy; or hydroxy $(C_2-C_5)$ alkanoxy;
  $R_3$ is cyano or $(C_1-C_3)$alkanoyl;
  $R_4$ is hydrogen, $(C_1-C_3)$alkyl; hydroxy $(C_2-C_5)$alkyl; or amino $(C_2-C_5)$alkyl;
  $R_5$ is aryl, or heteroaryl;
  $R_a$ and $R_b$ are each independently hydrogen, or $(C_1-C_3)$ alkyl; or $R_a$ and $R_b$ together with the nitrogen to which they are attached are pyrrolidino, piperidino, morpholino, or thiomorpholino;
  wherein any aryl, or heteroaryl of $R_1$ and $R_5$ is optionally substituted with one or more substituents independently selected from halo, nitro, cyano, hydroxy, trifluoromethyl, trifluoromethoxy, $(C_1-C_3)$alkoxy, $(C_1-C_3)$alkyl, $(C_1-C_3)$alkanoyl, $-S(O)_2R_c$, or $NR_aR_b$ wherein $R_c$ is $(C_1-C_3)$alkyl, or aryl or a pharmaceutically acceptable salt thereof;

provided that if $R_5$ is phenyl, the phenyl is substituted by —S(O)$_2$R$_c$, or is substituted by halo and at least one other substituent.

2. The method according to claim 1 wherein the leflunomide analog comprises the structure of LFM-A0, LFM-A1, LFM-A2, LFM-A3, LFM-A4, LFM-A5, LFM-A6, LFM-A7, LFM-A8, LFM-A9, LFM-A10, LFM-A11 or LFM-A12, and pharmaceutically acceptable salts thereof.

3. The method according to claim 2 wherein the leflunomide analog comprises the structure of LFM-A8 and pharmaceutically acceptable salts thereof.

4. A method for treating anaphylactic shock comprising administering to a patient a therapeutically effective amount of a leflunomide analog of formula I:

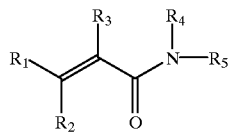

(I)

where:

$R_1$ is (C$_1$–C$_3$)alkyl, (C$_3$–C$_6$)cycloalkyl, phenyl, or NR$_a$R$_b$;

$R_2$ is hydroxy, (C$_1$–C$_6$)alkoxy (C$_1$–C$_6$)alkanoyloxy amino (C$_2$–C$_5$)alkoxy; hydroxy (C$_2$–C$_5$)alkoxy amino (C$_2$–C$_5$)alkanoxy; or hydroxy (C$_2$–C$_5$) alkanoxy;

$R_3$ is cyano or (C$_1$–C$_3$)alkanoyl;

$R_4$ is hydrogen, (C$_1$–C$_3$)alkyl; hydroxy (C$_2$–C$_5$)alkyl; or amino (C$_2$–C$_5$)alkyl;

$R_5$ is aryl, or heteroaryl;

$R_a$ and $R_b$ are each independently hydrogen, or (C$_1$–C$_3$) alkyl; or $R_a$ and $R_b$ together with the nitrogen to which they are attached are pyrrolidino, piperidino, morpholino, or thiomorpholino;

wherein any aryl, or heteroaryl of $R_1$ and $R_5$ is optionally substituted with one or more substituents independently selected from halo, nitro, cyano, hydroxy, trifluoromethyl, trifluoromethoxy, (C$_1$–C$_3$)alkoxy, (C$_{C3}$)alkyl, (C$_1$–C$_3$)alkanoyl, —S(O)$_2$R$_c$, or NR$_a$R$_b$, wherein R$_c$ is (C$_1$–C$_3$)alkyl, or aryl or a pharmaceutically acceptable salt thereof;

provided that if $R_5$ is phenyl, the phenyl is substituted by —S(O)$_2$R$_c$, or is substituted by halo and at least one other substituent.

5. The method according to claim 4 wherein the leflunomide analog comprises the structure of LFM-A0, LFM-A1, LFM-A2, LFM-A3, LFM-A4, LFM-A5, LFM-A6, LFM-A7, LFM-A8, LFM-A9, LFM-A10, LFM-A11 or LFM-A12, and pharmaceutically acceptable salts thereof.

6. The method according to claim 5 wherein the leflunomide analog comprises the structure of LFM-A8 and pharmaceutically acceptable salts thereof.

* * * * *